(12) United States Patent
Dyakonov et al.

(10) Patent No.: US 10,918,617 B2
(45) Date of Patent: *Feb. 16, 2021

(54) FUMARATE ESTER PHARMACEUTICAL COMPOSITIONS

(71) Applicant: BANNER LIFE SCIENCES LLC, High Point, NC (US)

(72) Inventors: Tatyana Dyakonov, Greensboro, NC (US); Sunil Agnihotri, Scarborough, ME (US); Aqeel A. Fatmi, High Point, NC (US)

(73) Assignee: BANNER LIFE SCIENCES LLC, High Point, NC (US)

( * ) Notice: Subject to any disclaimer, the term of this patent is extended or adjusted under 35 U.S.C. 154(b) by 164 days.

This patent is subject to a terminal disclaimer.

(21) Appl. No.: 16/129,908

(22) Filed: Sep. 13, 2018

(65) Prior Publication Data

US 2019/0015374 A1  Jan. 17, 2019

Related U.S. Application Data

(60) Continuation of application No. 15/730,841, filed on Oct. 12, 2017, now Pat. No. 10,105,337, which is a division of application No. 15/358,305, filed on Nov. 22, 2016, now Pat. No. 9,814,691, which is a division of application No. 15/073,714, filed on Mar. 18, 2016, now Pat. No. 9,511,043, which is a division of application No. 14/633,164, filed on Feb. 27, 2015, now Pat. No. 9,326,965.

(60) Provisional application No. 62/061,185, filed on Oct. 8, 2014, provisional application No. 62/011,604, filed on Jun. 13, 2014, provisional application No. 61/950,648, filed on Mar. 10, 2014, provisional application No. 61/946,233, filed on Feb. 28, 2014.

(51) Int. Cl.

| | |
|---|---|
| *A61K 31/225* | (2006.01) |
| *A61P 25/00* | (2006.01) |
| *A61K 9/10* | (2006.01) |
| *A61K 9/00* | (2006.01) |
| *A61K 47/46* | (2006.01) |
| *A61K 47/12* | (2006.01) |
| *A61K 47/44* | (2017.01) |
| *A61K 47/32* | (2006.01) |
| *A61K 47/14* | (2017.01) |
| *A61K 9/48* | (2006.01) |
| *A61K 45/06* | (2006.01) |

(52) U.S. Cl.
CPC .......... *A61K 31/225* (2013.01); *A61K 9/0053* (2013.01); *A61K 9/10* (2013.01); *A61K 9/48* (2013.01); *A61K 9/4808* (2013.01); *A61K 9/4858* (2013.01); *A61K 9/4866* (2013.01); *A61K 9/4875* (2013.01); *A61K 9/4891* (2013.01); *A61K 45/06* (2013.01); *A61K 47/12* (2013.01); *A61K 47/14* (2013.01); *A61K 47/32* (2013.01); *A61K 47/44* (2013.01); *A61K 47/46* (2013.01); *A61P 25/00* (2018.01)

(58) Field of Classification Search
None
See application file for complete search history.

(56) References Cited

U.S. PATENT DOCUMENTS

| | | |
|---|---|---|
| 5,146,730 A | 9/1992 | Dietel |
| 5,424,332 A | 6/1995 | Speiser |
| 5,459,983 A | 10/1995 | Dietel |
| 6,355,676 B1 | 3/2002 | Joshi |
| 6,436,992 B1 | 8/2002 | Joshi |
| 6,482,516 B1 | 11/2002 | Dietel |
| 6,509,376 B1 | 1/2003 | Joshi |
| 7,157,423 B2 | 1/2007 | Joshi |
| 7,320,999 B2 | 1/2008 | Joshi |
| 7,432,240 B2 | 10/2008 | Joshi |
| 7,612,110 B2 | 11/2009 | Joshi |
| 7,619,001 B2 | 11/2009 | Joshi |
| 7,803,840 B2 | 9/2010 | Joshi |
| 7,915,310 B2 | 3/2011 | Joshi |
| 8,293,270 B2 | 10/2012 | Sukuru |
| 8,333,989 B2 | 12/2012 | Sukuru |
| 8,399,514 B2 | 3/2013 | O Neill |
| 8,524,773 B2 | 9/2013 | Joshi |
| 8,669,281 B1 | 3/2014 | Sanrame |
| 8,669,282 B2 | 3/2014 | Zicker |
| 8,685,445 B2 | 4/2014 | Hassan |
| 8,759,393 B2 | 6/2014 | Joshi |

(Continued)

FOREIGN PATENT DOCUMENTS

| | | |
|---|---|---|
| EP | 0312697 A2 | 4/1989 |
| WO | 2000030622 | 6/2000 |

(Continued)

OTHER PUBLICATIONS

Gold et al., "Safety of a novel oral single-agent fumarate, BG00012, in patients with relapsing-remitting multiple sclerosis: results of a phase 2 study," Journal of Neurology 253(Suppl. 2): II144-II145 (2006).

Gullapalli, Journal of Pharmaceutical Science 99(10) 4107-4148 (2010).

Kappos et al., "BG00012, a novel oral fumarate, is effective in patients with relapsing-remitting multiple sclerosis", Multiple Sclerosis 2(Suppl. 1):S85 (2006).

Schilling et al., "Fumaric acid esters are effective in chronic experimental autoimmune encephalomyelitis and suppress macrophage infiltration," Clinical and Experimental Immunology 145(1):101-107 (2006).

(Continued)

*Primary Examiner* — Abigail Vanhorn

(74) *Attorney, Agent, or Firm* — Michael Best & Friedrich LLP

(57) ABSTRACT

Described herein are pharmaceutical compositions comprising fumarate esters, methods for making the same, and methods for treating subjects in need thereof. In particular, oral pharmaceutical compositions comprising fumarate esters are described.

16 Claims, 13 Drawing Sheets

(56) References Cited

U.S. PATENT DOCUMENTS

| | | |
|---|---|---|
| 9,090,558 B2 | 7/2015 | Sanrame |
| 9,302,977 B2 | 4/2016 | Raillard |
| 9,326,947 B1 | 5/2016 | Fatmi |
| 9,326,965 B2 | 5/2016 | Fatmi |
| 9,511,043 B2 | 12/2016 | Fatmi |
| 9,517,209 B2 | 12/2016 | Fatmi |
| 9,526,965 B2 | 12/2016 | Gatherer |
| 9,566,259 B1 | 2/2017 | Hughey |
| 9,636,318 B2 | 5/2017 | Hughey |
| 9,636,319 B1 | 5/2017 | Hughey |
| 9,814,691 B2 * | 11/2017 | Dyakonov ............ A61K 31/225 |
| 9,814,692 B2 * | 11/2017 | Vaughn ................ A61K 31/225 |
| 9,820,960 B2 * | 11/2017 | Dyakonov ............ A61K 9/4875 |
| 9,820,961 B2 * | 11/2017 | Vaughn ................ A61K 31/225 |
| 10,098,863 B2 * | 10/2018 | Vaughn ................ A61K 9/4808 |
| 10,105,335 B2 * | 10/2018 | Vaughn ................ A61K 31/225 |
| 10,105,336 B2 * | 10/2018 | Dyakonov ............ A61K 9/4875 |
| 10,105,337 B2 * | 10/2018 | Dyakonov ............ A61K 31/225 |
| 2003/0018072 A1 | 1/2003 | Joshi |
| 2004/0054001 A1 | 3/2004 | Petzelbauer |
| 2006/0051345 A1 | 3/2006 | Frohna |
| 2006/0115527 A1 | 6/2006 | Hassan |
| 2006/0165778 A1 | 7/2006 | Hassan |
| 2007/0104778 A1 | 5/2007 | Ketsela |
| 2007/0269507 A1 | 11/2007 | Sanchetto et al. |
| 2008/0003282 A1 | 1/2008 | Soll |
| 2008/0004344 A1 | 1/2008 | Nilsson |
| 2008/0233185 A1 | 9/2008 | Joshi |
| 2008/0299196 A1 | 12/2008 | Muller |
| 2008/0300217 A1 | 12/2008 | Nilsson |
| 2009/0304790 A1 | 12/2009 | Nilsson |
| 2010/0034274 A1 | 2/2010 | Li |
| 2010/0130607 A1 | 5/2010 | Gold |
| 2010/0259906 A1 | 10/2010 | Chang |
| 2010/0278879 A1 | 11/2010 | Manku |
| 2010/0324327 A1 | 12/2010 | Lee |
| 2011/0112196 A1 | 5/2011 | Lukashev |
| 2012/0034274 A1 | 2/2012 | Rupp |
| 2012/0165404 A1 | 6/2012 | Lukashev |
| 2012/0259012 A1 | 10/2012 | Lukashev |
| 2013/0115281 A1 | 5/2013 | Draper et al. |
| 2013/0216615 A1 | 8/2013 | Goldman |
| 2013/0259906 A1 | 10/2013 | Rupp |
| 2013/0295169 A1 | 11/2013 | Goldman |
| 2013/0302410 A1 | 11/2013 | Gold |
| 2013/0303613 A1 | 11/2013 | Lukashev |
| 2013/0315993 A1 | 11/2013 | Nilsson |
| 2013/0316003 A1 | 11/2013 | Nilsson |
| 2013/0317103 A1 | 11/2013 | Lukashev |
| 2013/0324539 A1 | 12/2013 | Annamalai |
| 2014/0037720 A1 | 2/2014 | Nilsson |
| 2014/0037740 A1 | 2/2014 | Nilsson |
| 2014/0056973 A1 | 2/2014 | Virsik |
| 2014/0056978 A1 | 2/2014 | Karaborni |
| 2014/0057917 A1 | 2/2014 | Virsik |
| 2014/0057918 A1 | 2/2014 | Shreeniwas |
| 2014/0065211 A1 | 3/2014 | Karaborni |
| 2014/0066505 A1 | 3/2014 | Joshi |
| 2014/0099364 A2 | 4/2014 | Nilsson |
| 2014/0163100 A1 | 6/2014 | Dawson |
| 2014/0179779 A1 | 6/2014 | Chao |
| 2014/0193495 A1 | 7/2014 | Nilsson |
| 2014/0199386 A1 | 7/2014 | Nilsson |
| 2014/0199387 A1 | 7/2014 | Nilsson |
| 2014/0199388 A1 | 7/2014 | Nilsson |
| 2014/0199390 A1 | 7/2014 | Nilsson |
| 2014/0199392 A1 | 7/2014 | Nilsson |
| 2014/0199393 A1 | 7/2014 | Nilsson |
| 2014/0200272 A1 | 7/2014 | Nilsson |
| 2014/0200273 A1 | 7/2014 | Nilsson |
| 2014/0200363 A1 | 7/2014 | Irdam |
| 2014/0205659 A1 | 7/2014 | Nilsson |
| 2014/0275048 A1 | 9/2014 | Sanrame |
| 2014/0275205 A1 | 9/2014 | Sanrame |
| 2014/0275250 A1 | 9/2014 | Cundy |
| 2014/0323570 A1 | 10/2014 | Gold |
| 2014/0348914 A9 | 11/2014 | Karaborni |
| 2014/0348915 A9 | 11/2014 | Karaborni |
| 2014/0350018 A9 | 11/2014 | Virsik |
| 2014/0378542 A1 | 12/2014 | Karaborni |
| 2015/0024049 A1 | 1/2015 | Nilsson |
| 2015/0079180 A1 | 3/2015 | Karaborni |
| 2015/0132747 A1 | 5/2015 | Lukashev |
| 2015/0190360 A1 | 7/2015 | Cundy |
| 2015/0209318 A1 | 7/2015 | Goldman |
| 2015/0246016 A1 | 9/2015 | Fatmi |
| 2015/0252013 A1 | 9/2015 | Annamalai |
| 2015/0307914 A9 | 10/2015 | Virsik |
| 2015/0366803 A1 | 12/2015 | O Neill |
| 2016/0101059 A1 | 4/2016 | Fatmi |
| 2016/0199335 A1 | 7/2016 | Fatmi |
| 2016/0199336 A1 | 7/2016 | Fatmi |
| 2017/0056359 A1 | 3/2017 | Hughey |
| 2017/0056360 A1 | 3/2017 | Hughey |
| 2017/0071891 A1 | 3/2017 | Fatmi |
| 2017/0100360 A1 | 4/2017 | Fatmi |
| 2017/0100361 A1 | 4/2017 | Hughey |
| 2017/0100362 A1 | 4/2017 | Hughey |
| 2017/0231942 A1 | 8/2017 | Vaughn et al. |
| 2019/0008818 A1 * | 1/2019 | Dyakonov ............ A61K 47/14 |
| 2019/0015372 A1 * | 1/2019 | Vaughn ................ A61K 9/4875 |
| 2019/0015373 A1 * | 1/2019 | Vaughn ................ A61K 31/225 |

FOREIGN PATENT DOCUMENTS

| | | |
|---|---|---|
| WO | 2000030622 A2 | 6/2000 |
| WO | 2002055063 A2 | 7/2002 |
| WO | 2002055066 A1 | 7/2002 |
| WO | 2002055067 A2 | 7/2002 |
| WO | 2004030658 A1 | 4/2004 |
| WO | 2005009409 A2 | 2/2005 |
| WO | 2005023241 A1 | 3/2005 |
| WO | 2006023629 A2 | 3/2006 |
| WO | 2006023649 A2 | 3/2006 |
| WO | 2006023651 A2 | 3/2006 |
| WO | 2006036371 A2 | 4/2006 |
| WO | 2006037342 A2 | 4/2006 |
| WO | 2007042034 A1 | 4/2007 |
| WO | 2007042035 A2 | 4/2007 |
| WO | 2008096271 A2 | 8/2008 |
| WO | 2010022177 A2 | 2/2010 |
| WO | 2010079222 A1 | 7/2010 |
| WO | 2010126605 A1 | 11/2010 |
| WO | 2012013331 A2 | 2/2012 |
| WO | 2012162669 A1 | 11/2012 |
| WO | 2012170923 A1 | 12/2012 |
| WO | 2013076216 A1 | 5/2013 |
| WO | 2013090799 A1 | 6/2013 |
| WO | 2013092269 A1 | 6/2013 |
| WO | 2013112859 A1 | 8/2013 |
| WO | 2013119677 A1 | 8/2013 |
| WO | 2013148690 A1 | 10/2013 |
| WO | 2013158969 A1 | 10/2013 |
| WO | 2014028299 A1 | 2/2014 |
| WO | 2014031844 A1 | 2/2014 |
| WO | 2014031892 A1 | 2/2014 |
| WO | 2014031894 A1 | 2/2014 |
| WO | 2014031897 A1 | 2/2014 |
| WO | 2014031901 A1 | 2/2014 |
| WO | 2014143146 A1 | 9/2014 |
| WO | 2014190056 A2 | 11/2014 |
| WO | 2014197860 A1 | 12/2014 |
| WO | 2015017762 A1 | 2/2015 |
| WO | 2015028472 A1 | 3/2015 |
| WO | 2015028473 A1 | 3/2015 |
| WO | 2015042294 A1 | 3/2015 |
| WO | 2015044853 A2 | 4/2015 |
| WO | 2015086467 A1 | 6/2015 |
| WO | 2015089420 A1 | 6/2015 |
| WO | 2015105757 A1 | 7/2015 |
| WO | 2015128492 A1 | 9/2015 |
| WO | 2015130998 A1 | 9/2015 |

(56) References Cited

FOREIGN PATENT DOCUMENTS

WO          2016057133 A1     4/2016
WO          2017040272 A1     3/2017

OTHER PUBLICATIONS

Schimrigk et al., "Oral fumaric acid esters for the treatment of active multiple sclerosis: an open-label, baseline-controlled pilot study," European J. Neurology 13(6): 604-610 (2006).
Sheikh et al., "Tolerability and pharmacokinetics of delayed-release dimethyl fumarate administered with and without aspirin in healthy volunteers," Clinical Therapeutics 35(10): 1582-1594 (2013).
Tecfidera® Prescribing Information Mar. 2013 (Biogen IDEC).
Verma, R.K., et al., "Formulation Aspects in the Development of Osmotically Controlled Oral Drug Delivery Systems," Journal of Controlled Release, 79: 7-27 (2002).
Yeh et al., "Effect of Medium-Chain Glycerides on Physiological Properties of Rabbit Intestinal Epitheliun1 in Vitro," Pharma. Res. 11(8): 1148-1154 (1994).
Canadian Patent Office Action for Application No. 2,962,916 dated Jul. 16, 2020 (4 pages).

\* cited by examiner

FUMARATE ESTER PHARMACEUTICAL COMPOSITIONS

CROSS REFERENCE TO RELATED APPLICATIONS

This application is a continuation of U.S. patent application Ser. No. 15/730,841, filed on Oct. 12, 2017, which is a divisional of U.S. patent application Ser. No. 15/358,305, filed on Nov. 22, 2016, which is a divisional of U.S. patent application Ser. No. 15/073,714, filed on Mar. 18, 2016, which is divisional of U.S. patent application Ser. No. 14/633,164, filed on Feb. 27, 2015, which claims priority to U.S. Provisional Patent Application Nos. 61/946,233, filed on Feb. 28, 2014; 61/950,648, filed on Mar. 10, 2014; 62/011,604, filed on Jun. 13, 2014, and 62/061,185, filed on Oct. 8, 2014, each of which are incorporated by reference herein in their entirety.

TECHNICAL FIELD

Described herein are pharmaceutical compositions comprising fumarate esters, methods for making the same, and methods for treating subjects in need thereof. In particular, oral pharmaceutical compositions comprising fumarate esters are described.

BACKGROUND

Fumaric acid esters (FAE; fumarate esters, e.g., dialkyl fumarate esters such as dimethyl fumarate or monomethyl fumarate) are pharmacologically active substances used for treating hyperproliferative, inflammatory, or autoimmune disorders. They were first used to treat psoriasis and were licensed for this indication in Germany in 1995 as Fumaderm® (Biogen Idec, Inc., Cambridge, Mass., USA). Fumaderm® produces various undesirable side effects, including flushing, headaches, dizziness, eructation, nausea, vomiting, abdominal and intestinal cramps, and diarrhea. High concentrations of the drug released in the stomach are believed to be responsible for such side effects.

After oral intake, the main component of Fumaderm®, dimethyl fumarate (DMF), is hydrolysed by esterases to monomethyl fumarate (MMF), the bioactive metabolite. After absorption in the small intestine, MMF is believed to interact with immunocytes in the bloodstream. The primary plasma metabolites of DMF are monomethyl fumarate, fumaric acid, citric acid, and glucose. Monomethyl fumarate is further metabolized in the tricarboxylic acid cycle to carbon dioxide and water.

An improved oral formulation of the FAE BG-12 active ingredient (i.e., DMF) was developed and approved for the treatment of multiple sclerosis. This formulation, TECFIDERA® (Biogen Idec, Inc.), is available as hard gelatin delayed-release capsules containing 120 mg or 240 mg of granulated dimethyl fumarate enterically coated minitablets. See International Patent Application Publication No. WO 2013/119677 and U.S. Pat. No. 6,509,376, which are incorporated by reference herein for such teachings. TECFIDERA® was intended to reduce the undesirable side effects by preventing release of DMF in the stomach.

The enterically coated DMF granules in TECFIDERA®, however, lack uniformity in shape and size, and the enteric coating may not be evenly distributed over the minitablets. This lack of homogeneity can diminish the enteric properties and affect the acid-resistance, dissolution, and release rates. In addition, the integrity of the acid-resistant coating fails when the coating cracks or flakes off. This leads to DMF release in the stomach and can cause flushing and the negative gastrointestinal side effects.

A subject's stomach content also affects delivery of DMF from TECFIDERA®. A meal was shown to decrease $C_{max}$ by 40% and delay $T_{max}$ from 2.0 hours to 5.5 hours; the AUC was unaffected. See WO 2006/037342, which is incorporated by reference herein for such teachings. This was shown to reduce the incidence of flushing by approximately 25% in the postprandial state. See TECFIDERA® Prescribing Information March 2013 (Biogen Idec Inc.), which is incorporated by reference herein for such teachings.

In addition, DMF sublimes at relatively low temperatures. About 15-20% of the DMF active ingredient is lost owing to sublimation during the wet-granulation processing used for manufacturing TECFIDERA®. See WO 2013/076216, which is incorporated by reference herein for such teachings. Sublimation also causes loss of DMF during storage and unused TECFIDERA® capsules must be discarded 90 days after a bottle of the capsules is opened.

Accordingly, it is desirable to develop oral controlled release formulations of fumarate esters: (1) that prevent flushing and the undesirable GI side effects associated with oral administration of fumarate esters; (2) that reduce or eliminate fumarate ester sublimation during manufacturing and storage; (3) that increase the long-term stability of the pharmaceutical composition; and (4) that provide a variety of different release profiles, dosage forms, and dosing regimens.

SUMMARY

Described herein are controlled release pharmaceutical compositions comprising fumarate esters suspended in a lipid or lipophilic matrix. The pharmaceutical composition is encapsulated in an enteric soft capsule. The oral enteric soft capsules comprising controlled release matrix compositions prevent release of the fumarate ester active ingredient in the gastric environment, but release the active ingredient in the intestine in a controlled manner. The compositions can be tailored to provide immediate release, controlled release, delayed release, or extended release pharmacokinetics by the composition of the matrix fill. The formulations described herein comprise solid micronized particles of fumarate esters suspended in a matrix. The controlled release enteric capsule comprising a matrix of fumarate esters are predicted to reduce, ameliorate, or eliminate the undesirable gastrointestinal side effects observed with prior fumarate ester pharmaceuticals. Further, the formulations preclude or reduce sublimation of the fumarate ester during manufacturing and storage.

One embodiment described herein is an oral pharmaceutical composition comprising a controlled release composition of a fumarate ester, including, but not limited to, dimethyl fumarate (DMF) or monomethyl fumarate (MMF). In one embodiment, the pharmaceutical composition comprises a controlled release enteric soft capsule and matrix comprising a fumarate ester. In one aspect, the matrix comprises a lipid or lipophilic vehicle, a neutralizing agent, and solid particles of fumarate esters. In another aspect, the matrix comprises a lipid or lipophilic vehicle, a neutralizing agent, excipients, and solid particles of a fumarate ester. In another aspect, the matrix comprises a lipid or lipophilic vehicle, a neutralizing agent, surfactants, and solid particles of a fumarate ester. In one aspect, the lipid or lipophilic vehicle comprises polyvinylpyrrolidones, mono- and di-glycerides, and oils. In another aspect, the surfactant can comprise polysorbate 80 or polyoxyl 40 hydrogenated castor oil. In another aspect, the solid particles of fumarate ester comprise milled or micronized particles. In another aspect, the milled or micronized particles of fumarate ester comprise average particle distribution sizes of about 20 µm to about 300 µm, including each integer within the specified range. In another aspect, the solid particles of fumarate esters comprise average particle distribution sizes of about 70 µm to about 260 µm, including each integer within the specified range. In another aspect, the solid microparticles of fumarate esters have average particle distribution sizes of about 68 µm. In another aspect, the solid particles of fumarate esters have average particle distribution sizes of about 260 µm. In another aspect, the neutralizing agent comprises an organic acid, ester, or salt. In another aspect, the neutralizing agent comprises at least one of lactate, fumarate, caprylate, caprate, oleate, maleate, succinate, tartrate, citrate, glutamate, gluconate, or esters or salts thereof, or combinations thereof. In another aspect, the matrix comprises a fumarate ester, a mixture of mono- and di-glycerides, polyvinylpyrrolidone, polyoxyl 40 hydrogenated castor oil, and lactic acid.

In another embodiment, the pharmaceutical composition comprises a matrix fill comprising about 28-32% by weight of fumarate ester (PSD 80 µm); about 50-54% of a mixture of mono- and di-glycerides; at least about 1-10% polyvinylpyrrolidone; at least about 1-10% polyoxyl 40 hydrogenated castor oil, and at least about 1-5% lactic acid. In one aspect, the composition has controlled release, delayed release, or extended release properties. In another aspect, the composition further comprises one or more non-steroidal anti-inflammatory drugs (NSAIDS). In one aspect, the composition prevents sublimation of the fumarate ester during manufacturing. In another aspect, the composition prophylactically reduces the onset or ameliorates the symptoms of any flushing side effects. In another aspect, the composition reduces the onset or ameliorates the severity of any gastrointestinal side effects. In another aspect, the composition is stable for at least 1 year at conditions comprising 25° C., 60% relative humidity. In another aspect, the composition is stable for at least 2 years at conditions comprising 25° C., 60% relative humidity.

In one embodiment, the enteric soft capsule shell comprises one or more enteric, acid-insoluble polymers, a film-forming polymer, a plasticizer, an alkali-neutralizing agent, a solvent, and optionally, a coloring agent, a flavoring, or a pharmaceutical excipient.

In another embodiment, the enteric soft capsule shell comprises about 30% of at least one film-forming polymer; about 10% of at least one enteric, acid-insoluble polymer; about 20% at least one plasticizer; about 1% of at least one alkali-neutralizing agent; about 37% of a solvent; and about 1.5% of an opacifying agent. In one aspect, the enteric soft capsule shell comprises gelatin, acrylic methacrylate copolymers, glycerol, triethyl citrate, ammonia, water, and titanium dioxide.

Another embodiment described herein is a method for manufacturing an oral enteric soft capsule shell and matrix comprising a fumarate ester, the method comprising: (i) providing a matrix fill comprising any of the composition described herein; (ii) providing an enteric soft capsule shell comprising any of the composition described herein; (iii) casting the enteric soft capsule shell into films using heat-controlled drums or surfaces; and (iv) forming an enteric soft capsule comprising the matrix fill composition using rotary die encapsulation technology. In one aspect, an enteric soft capsule comprising a fumarate ester matrix produced by said method.

Another embodiment described herein is an enteric soft capsule comprising a fumarate ester matrix, wherein the matrix comprises: about 28-32% fumarate ester (PSD: 80 µm); about 50-54% mono- and di-glycerides; at least about 1-7% polyvinylpyrrolidone; at least about 2-10% polyoxyl 40 hydrogenated castor oil, and at least about 1-5% lactic acid; and wherein the enteric soft capsule shell comprises: about 30% gelatin; about 10% methylacrylic acid copolymer; about 18% glycerol; about 1% triethyl citrate; about 1.5% ammonia; about 37% water; and about 1.5% titanium dioxide.

In one aspect, the enteric soft capsule comprising a fumarate ester is resistant to dissolution at about pH 1.2 for at least about 2 hours. In another aspect, the enteric soft capsule comprising a fumarate ester begins dissolution at pH of about 6.8 within about 10 min. In one aspect, the enteric soft capsule has immediate release, controlled release, delayed release, or extended release properties. In another aspect, the enteric soft capsule comprising a fumarate ester reduces the onset or ameliorates the severity of any flushing or gastrointestinal side effects.

Another embodiment described herein is a method for treating, retarding the progression of, delaying the onset of, prophylaxis of, amelioration of, or reducing the symptoms of multiple sclerosis or psoriasis, comprising administering to a subject in need thereof an oral pharmaceutical composition comprising a controlled release enteric soft capsule and matrix comprising fumarate ester. In one aspect, the pharmaceutical composition comprises a controlled release enteric soft capsule comprising a formulation of fumarate ester.

Another embodiment described herein is an oral pharmaceutical composition as described herein that is useful for treating neurodegenerative disorders. In one aspect, the pharmaceutical composition is useful for treating multiple sclerosis or psoriasis. In one embodiment described herein, subjects that are administered the oral pharmaceutical composition as described herein exhibit a mean plasma monomethyl fumarate $T_{max}$ of from about 1.5 hours to about 3.5 hours.

Another embodiment described herein is a pharmaceutical composition comprising a controlled release composition comprising a formulation of a fumarate ester useful for treating, retarding the progression of, delaying the onset of, prophylaxis of, amelioration of, or reducing the symptoms of general autoimmune or neurodegenerative disorders, including but not limited to, acute dermatitis, adrenal leukodystrophy, AGE-induced genome damage, Alexander's disease, alopecia areata (totalis and universalis), Alper's disease, Alzheimer's disease, amyotrophic lateral sclerosis, angina pectoris, arthritis, asthma, autoimmune diseases, balo concentric sclerosis, Behçet's syndrome, bullous pemphigoid, Canavan disease, cardiac insufficiency including left ventricular insufficiency, central nervous system vasculitis, Charcot-Marie-Tooth disease, childhood ataxia with central nervous system hypomyelination, chronic active (lupoid) hepatitis, chronic dermatitis, chronic idiopathic peripheral neuropathy, chronic obstructive pulmonary disease, contact dermatitis, Crohn's disease and cutaneous Crohn's disease, cutaneous lupus, cutaneous sarcoidosis, diabetic retinopathy, fibromyalgia, graft versus host disease, granuloma annulare, granulomas including annulare, Grave's disease, Hashimoto's thyroiditis, hepatitis C viral infection, herpes simplex viral infection, human immunodeficiency viral infection, Huntington's disease, inflammatory bowel disease, irritable bowel disorder, ischemia, juvenile-onset diabetes mellitus, Krabbe disease, lichen planus, macular degeneration, mitochondrial encephalomyopathy, monomelic amyotrophy, multiple sclerosis (MS), myocardial infarction, necrobiosis lipoidica, neurodegeneration with brain iron accumulation, neurodermatitis, neuromyelitis optica, neuropathic pain, neurosarcoidosis, NF-κB mediated diseases, optic neuritis, organ transplantation rejection, paraneoplastic syndromes, Parkinson's disease, Pelizaeus-Merzbacher disease, pemphigus, pernicious anemia, primary lateral sclerosis, progressive supranuclear palsy, psoriasis, psoriatic arthritis, pyoderma gangrenosum, radicular pain, radiculopathic pain, reperfusion injury, retinopathic pigmentosa, rheumatoid arthritis (RA), sarcoidosis, sarcoidosis, Schilder's disease, sciatic pain, sciatica, Sjögren's syndrome, subacute necrotizing myelopathy, such as polyarthritis, Susac's syndrome, systemic lupus erythematosus (SLE), tumors, transverse myelitis, ulcerative colitis, or Zellweger syndrome.

Another embodiment described herein is a method for treating, retarding the progression of, delaying the onset of, prophylaxis of, amelioration of, or reducing the symptoms of general autoimmune or neurodegenerative disorders, including but not limited to, acute dermatitis, adrenal leukodystrophy, AGE-induced genome damage, Alexander's disease, alopecia areata (totalis and universalis), Alper's disease, Alzheimer's disease, amyotrophic lateral sclerosis, angina pectoris, arthritis, asthma, autoimmune diseases, balo concentric sclerosis, Behçet's syndrome, bullous pemphigoid, Canavan disease, cardiac insufficiency including left ventricular insufficiency, central nervous system vasculitis, Charcot-Marie-Tooth disease, childhood ataxia with central nervous system hypomyelination, chronic active (lupoid) hepatitis, chronic dermatitis, chronic idiopathic peripheral neuropathy, chronic obstructive pulmonary disease, contact dermatitis, Crohn's disease and cutaneous Crohn's disease, cutaneous lupus, cutaneous sarcoidosis, diabetic retinopathy, fibromyalgia, graft versus host disease, granuloma annulare, granulomas including annulare, Grave's disease, Hashimoto's thyroiditis, hepatitis C viral infection, herpes simplex viral infection, human immunodeficiency viral infection, Huntington's disease, inflammatory bowel disease, irritable bowel disorder, ischemia, juvenile-onset diabetes mellitus, Krabbe disease, lichen planus, macular degeneration, mitochondrial encephalomyopathy, monomelic amyotrophy, multiple sclerosis (MS), myocardial infarction, necrobiosis lipoidica, neurodegeneration with brain iron accumulation, neurodermatitis, neuromyelitis optica, neuropathic pain, neurosarcoidosis, NF-κB mediated diseases, optic neuritis, organ transplantation rejection, paraneoplastic syndromes, Parkinson's disease, Pelizaeus-Merzbacher disease, pemphigus, pernicious anemia, primary lateral sclerosis, progressive supranuclear palsy, psoriasis, psoriatic arthritis, pyoderma gangrenosum, radicular pain, radiculopathic pain, reperfusion injury, retinopathic pigmentosa, rheumatoid arthritis (RA), sarcoidosis, sarcoidosis, Schilder's disease, sciatic pain, sciatica, Sjögren's syndrome, subacute necrotizing myelopathy, such as polyarthritis, Susac's syndrome, systemic lupus erythematosus (SLE), tumors, transverse myelitis, ulcerative colitis, or Zellweger syndrome comprising administering to a subject in need thereof an oral pharmaceutical composition comprising a controlled release formulation comprising a comprising a fumarate ester. In one embodiment described herein, the oral pharmaceutical composition comprises an enteric soft capsule and matrix comprising a fumarate ester.

In one aspect, the pharmaceutical composition comprises a controlled release enteric soft capsule comprising a formulation of a fumarate ester. In another aspect, the pharmaceutical composition is an immediate release, delayed release, controlled release, or extended release formulation of a fumarate ester.

Another embodiment described herein is an oral pharmaceutical composition comprising an immediate release, delayed release, controlled release, or extended release formulation of a fumarate ester. In one aspect, the composition is provided in a dosage form containing a total amount of about 240 mg of a fumarate ester, wherein subjects administered the dosage form twice-daily exhibit one or more pharmacokinetic parameters selected from the group consisting of (a) a mean plasma monomethyl fumarate $C_{max}$ ranging from about 1.03 mg/L to about 2.41 mg/L and (b) a mean plasma monomethyl fumarate $AUC_{overall}$ ranging from about 4.81 h·mg/L to about 11.2 h·mg/L. In another aspect, the composition is provided in a dosage form containing a total amount of about 240 mg of a fumarate ester, wherein subjects administered the dosage form exhibit one or more pharmacokinetic parameters selected from the group consisting of (a) a mean plasma monomethyl fumarate $C_{max}$ ranging from about 1.5 mg/L to about 3.4 mg/L, (b) a mean plasma monomethyl fumarate $AUC_{0\to 12h}$ ranging from about 2.4 h·mg/L to about 5.5 h·mg/L, and (c) a mean $AUC_{0\to\infty}$ ranging from about 2.4 h·mg/L to about 5.6 h·mg/L. In another aspect, the fumarate ester formulation is encapsulated in an enteric soft capsule. In another aspect, the capsule contains a total amount of about 240 mg of a fumarate ester, wherein subjects administered the capsule exhibit one or more pharmacokinetic parameters selected from the group consisting of (a) a mean plasma monomethyl fumarate $T_{max}$ of from about 1.5 hours to about 3.5 hours; (b) a mean plasma monomethyl fumarate $C_{max}$ ranging from about 1.5 mg/L to about 3.4 mg/L; (c) a mean plasma monomethyl fumarate $AUC_{0\to 12h}$ ranging from about 2.4 h·mg/L to about 5.5 h·mg/L; and (d) a mean $AUC_{0\to\infty}$ ranging from about 2.4 h·mg/L to about 5.6 h·mg/L.

Another embodiment described herein is a once daily oral pharmaceutical composition comprising a delayed release, controlled release, or extended release formulation of a fumarate ester. In one aspect, the composition is provided in a dosage form containing a total amount of about 480 mg of a fumarate ester, wherein subjects administered the dosage form once daily exhibit one or more pharmacokinetic parameters selected from the group consisting of (a) a mean plasma monomethyl fumarate $C_{max}$ ranging from about 1.03 mg/L to about 5.2 mg/L and (b) a mean plasma monomethyl fumarate $AUC_{0\to\infty}$ ranging from about 2.4 h·mg/L to about 15.5 h·mg/L. In another aspect, the composition is provided in a dosage form containing a total amount of about 480 mg of a fumarate ester, wherein subjects administered the dosage form once daily exhibit one or more pharmacokinetic parameters selected from the group consisting of (a) a mean plasma monomethyl fumarate $C_{max}$ ranging from about 1.5 mg/L to about 5.2 mg/L, (b) a mean plasma monomethyl fumarate $AUC_{0\to 12h}$ ranging from about 2.4 h·mg/L to about 13.5 h·mg/L, and (c) a mean $AUC_{0\to\infty}$ ranging from about 2.4 h·mg/L to about 15.5 h·mg/L. In another aspect, the fumarate ester formulation is encapsulated in an enteric soft capsule. In another aspect, the capsule contains a total amount of about 480 mg of a fumarate ester, wherein subjects administered the capsule once daily exhibit one or more pharmacokinetic parameters selected from the group consisting of (a) a mean plasma monomethyl fumarate $T_{max}$ of from about 1.5 hours to about 10.5 hours; (b) a mean plasma monomethyl fumarate $C_{max}$ ranging from about 1.5 mg/L to about 5.2 mg/L; (c) a mean plasma monomethyl fumarate $AUC_{0\to 12h}$ ranging from about 2.4 h·mg/L to about 13.5 h·mg/L; and (d) a mean $AUC_{0\to\infty}$ ranging from about 2.4 h·mg/L to about 15.5 h·mg/L.

Another embodiment described herein is a method for treating, retarding the progression of, delaying the onset of, prophylaxis of, amelioration of, or reducing the symptoms of a general autoimmune or neurodegenerative disorder, including but not limited to multiple sclerosis or psoriasis, comprising orally administering to a subject in need thereof a therapeutically effective amount of a fumarate ester comprising any of the compositions described herein and a therapeutically amount of one or more non-steroidal anti-inflammatory drugs effective to reduce flushing. In one aspect, the one or more non-steroidal anti-inflammatory drug is aspirin, ibuprofen, naproxene, diclofenac, ketoprofen, celecoxib, or a combination thereof.

Another embodiment described herein is a method for treating, retarding the progression of, delaying the onset of, prophylaxis of, amelioration of, or reducing the symptoms of a general autoimmune or neurodegenerative disorder, including but not limited to multiple sclerosis or psoriasis, comprising administering to a subject in need thereof any one of the compositions described herein containing a compound, or a pharmaceutically acceptable salt thereof, that metabolizes to monomethyl fumarate wherein said administering the composition provides one or more of the following pharmacokinetic parameters: (a) a mean plasma monomethyl fumarate $T_{max}$ of from about 1.5 hours to about 10.5 hours; (b) a mean plasma monomethyl fumarate $C_{max}$ ranging from about 1.03 mg/L to about 5.2 mg/L; (c) a mean plasma monomethyl fumarate $AUC_{overall}$ ranging from about 4.81 h·mg/L to about 15.2 h·mg/L; (d) a mean plasma monomethyl fumarate $AUC_{0\to 12h}$ ranging from about 2.4 h·mg/L to about 13.5 h·mg/L; and (e) a mean $AUC_{0\to\infty}$ ranging from about 2.4 h·mg/L to about 15.5 h·mg/L.

Another embodiment described herein is a pharmaceutical composition comprising any one of the pharmaceutical compositions described herein for administration to a subject having multiple sclerosis, comprising a therapeutically effective amount of one or more fumarate esters, wherein the administration is sufficient to achieve a reduction of about 0.224 annualized relapse rate relative to baseline in the subject without substantially inducing one or more of flushing, abdominal pain, diarrhea, and nausea in the subject. In one aspect, the subject experiences one or more of flushing, abdominal pain, diarrhea, and nausea at a rate of less than about 10%. In another aspect, the subject is a child. In one aspect, the child is over 9.

Another embodiment described herein is a method for treating, retarding the progression of, delaying the onset of, prophylaxis of, amelioration of, or reducing the symptoms of a general autoimmune or neurodegenerative disorder, including but not limited to multiple sclerosis or psoriasis, the method comprising the administration of a therapeutically effective amount of one or more fumarate esters comprising any of the pharmaceutical compositions described herein to a subject in need thereof, wherein the subject achieves a reduction of annualized relapse rate relative to baseline without substantially experiencing one or more of flushing, abdominal pain, diarrhea, and nausea. In one aspect, the subject experiences one or more of flushing, abdominal pain, diarrhea, and nausea at a rate of less than about 10%. In another aspect, the subject is a child. In one aspect, the child is over 9.

Another embodiment described herein is a method for treating, retarding the progression of, delaying the onset of, prophylaxis of, amelioration of, or reducing the symptoms of multiple sclerosis or psoriasis, the method comprising the administration of a therapeutically effective amount of one or more fumarate esters comprising any of the pharmaceutical compositions described herein to a subject with multiple sclerosis, wherein the administration is sufficient to achieve a reduction of about 0.224 annualized relapse rate relative to baseline in the subject without substantially inducing one or more of flushing, abdominal pain, diarrhea, and nausea in the subject. In one aspect, the subject experiences one or more of flushing, abdominal pain, diarrhea, and nausea at a rate of less than about 10%. In another aspect, the subject is a child. In one aspect, the child is over 9.

Another embodiment described herein is a pharmaceutical composition comprising any of the pharmaceutical compositions described herein for administration to a subject having a general autoimmune or neurodegenerative disorder, including but not limited to multiple sclerosis, comprising a therapeutically effective amount of one or more fumarate esters, wherein the administration is sufficient to achieve a reduction of about 0.224 annualized relapse rate relative to baseline in the subject without substantially inducing one or more of flushing, abdominal pain, diarrhea, and nausea in the subject and wherein the administration does not require titration of the pharmaceutical composition. In one aspect, the subject experiences one or more of flushing, abdominal pain, diarrhea, and nausea at a rate of less than about 10%. In another aspect, the subject is a child. In one aspect, the child is over 9.

Another embodiment described herein is a method for treating, retarding the progression of, delaying the onset of, prophylaxis of, amelioration of, or reducing the symptoms of a general autoimmune or neurodegenerative disorder, including but not limited to multiple sclerosis, the method comprising the administration of a therapeutically effective amount of one or more fumarate esters comprising any of the pharmaceutical compositions described herein to a subject in need thereof, wherein the administration is sufficient to achieve a reduction of about 0.224 annualized relapse rate relative to baseline in the subject without substantially inducing one or more of flushing, abdominal pain, diarrhea, and nausea in the subject and wherein the administration does not require titration of the pharmaceutical composition. In one aspect, the subject experiences one or more of flushing, abdominal pain, diarrhea, and nausea at a rate of less than about 10%. In another aspect, the subject is a child. In one aspect, the child is over 9.

Another embodiment described herein is a pharmaceutical composition comprising any of the compositions described herein for administration to a subject having a general autoimmune or neurodegenerative disorder, including but not limited to multiple sclerosis or psoriasis, comprising a therapeutically effective amount of one or more fumarate esters, wherein the pharmaceutical composition is stable at 25° C. 60% RH for at least 1 year.

Another embodiment described herein is a pharmaceutical composition comprising any of the compositions described herein comprising a therapeutically effective amount of one or more fumarate esters for administration to a subject diagnosed with multiple sclerosis or psoriasis.

Another embodiment described herein is a method for treating, retarding the progression of, delaying the onset of, prophylaxis of, amelioration of, or reducing the symptoms of a general autoimmune or neurodegenerative disorder, including but not limited to multiple sclerosis or psoriasis, comprising orally administering to a subject in need thereof a therapeutically effective amount of a fumarate ester comprising any of the pharmaceutical compositions described herein.

Another embodiment described herein is a method for treating, retarding the progression of, delaying the onset of, prophylaxis of, amelioration of, or reducing the symptoms of a general autoimmune or neurodegenerative disorder, including but not limited to multiple sclerosis or psoriasis, comprising orally administering to a subject in need thereof a therapeutically effective amount of a fumarate ester comprising any of the pharmaceutical compositions described herein and a therapeutically amount of a leukotriene receptor antagonist. In one aspect, the leukotriene receptor antagonist comprises montelukast or zafirlukast.

Another embodiment described herein is a pharmaceutical composition comprising a matrix fill comprising any of the compositions described herein in Tables 1, 2, and 5-23.

Another embodiment described herein is a pharmaceutical composition for treating, retarding the progression of, delaying the onset of, prophylaxis of, amelioration of, or reducing the symptoms of a general autoimmune or neurodegenerative disorder, including but not limited to multiple sclerosis or psoriasis, comprising a fumarate ester, wherein the pharmaceutical composition exhibits an in vitro dissolution rate (% dissolution per minute) at pH 6.8, as shown in any of Drawings 2-12 described herein.

Another embodiment described herein is a method for treating, retarding the progression of, delaying the onset of, prophylaxis of, amelioration of, or reducing the symptoms of a general autoimmune or neurodegenerative disorder, including but not limited to multiple sclerosis or psoriasis, comprising orally administering to a subject in need thereof a therapeutically effective amount of a fumarate ester comprising any of the pharmaceutical compositions described herein, wherein the composition exhibits an in vitro dissolution rate (% dissolution per minute) at pH 6.8, as shown in any of Drawings 2-12 described herein.

Another embodiment described herein is a pharmaceutical composition for treating, retarding the progression of, delaying the onset of, prophylaxis of, amelioration of, or reducing the symptoms of a general autoimmune or neurodegenerative disorder, including but not limited to multiple sclerosis or psoriasis, comprising a fumarate ester, wherein the pharmaceutical composition exhibits an in vitro dissolution rate at pH 6.8 comprising about 10% to about 80% dissolution after about 10 minutes to about 480 minutes.

Another embodiment described herein is a method for treating, retarding the progression of, delaying the onset of, prophylaxis of, amelioration of, or reducing the symptoms of a general autoimmune or neurodegenerative disorder, including but not limited to multiple sclerosis or psoriasis, comprising orally administering to a subject in need thereof a therapeutically effective amount of a fumarate ester comprising any of the compositions described herein, wherein the pharmaceutical composition exhibits an in vitro dissolution rate (% dissolution per minute) at pH 6.8, as shown in any of Drawings 2-12 described herein.

Another embodiment described herein is a method for treating, retarding the progression of, delaying the onset of, prophylaxis of, amelioration of, or reducing the symptoms of general autoimmune or neurodegenerative disorders, including but not limited to multiple sclerosis or psoriasis, comprising orally administering to a subject in need thereof a therapeutically effective amount of a fumarate ester comprising any of the pharmaceutical compositions described herein, wherein the pharmaceutical composition is administered without titration of the pharmaceutical composition and without substantially inducing one or more of flushing, abdominal pain, diarrhea, and nausea in the subject.

Another embodiment described herein is a pharmaceutical composition for treating, retarding the progression of, delaying the onset of, prophylaxis of, amelioration of, or reducing the symptoms of general autoimmune or neurodegenerative disorders, comprising a fumarate ester, wherein the pharmaceutical composition is administered without titration of the pharmaceutical composition and without substantially inducing one or more of flushing, abdominal pain, diarrhea, and nausea in the subject.

DETAILED DESCRIPTION

Figure 1:
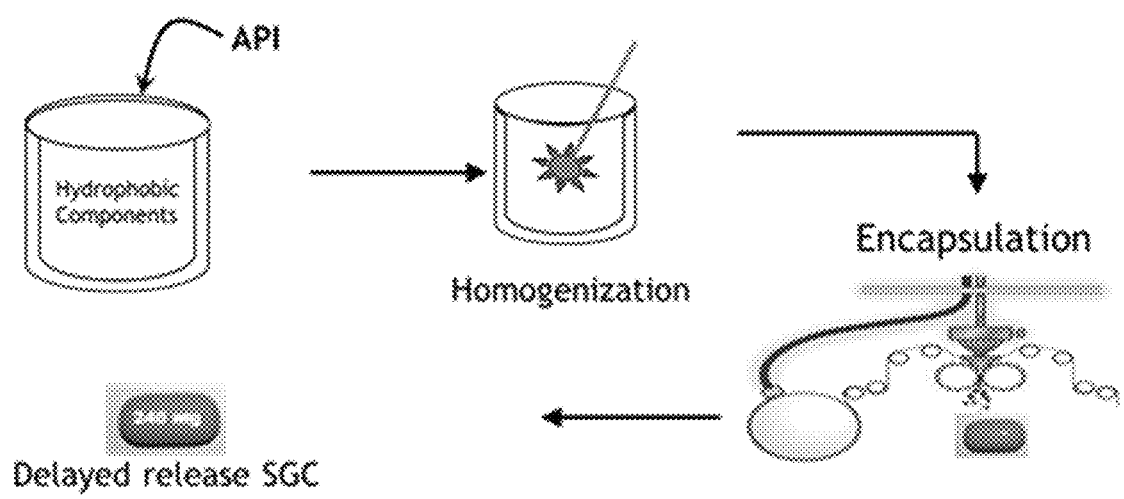
FIG. 1. Scheme for manufacturing enteric soft capsules comprising a DMF matrix.

Described herein are pharmaceutical compositions of fumarate esters such as dimethyl fumarate, monomethyl fumarate, other pharmacologically active fumarate esters, or combinations thereof.

The pharmaceutical compositions described herein provide matrix fills of fumarate esters, such as dimethyl fumarate, monomethyl fumarate, or combinations thereof, and methods for preparation thereof. Also described herein are compositions and methods for manufacturing controlled, delayed, or extended release fumarate esters, dimethyl fumarate, monomethyl fumarate, or combinations thereof as enteric soft capsules. In one embodiment described herein, the fumarate ester pharmaceutical composition is placed within an enteric soft capsule shell. In another embodiment, the fumarate ester is in the form of solid microparticles of defined size within a matrix comprising a lipid or lipophilic vehicle.

As used herein, the term "fumarate ester" or "FAE" refers to any pharmacologically active dialkyl fumarate ester, such as dimethyl fumarate, monomethyl fumarate, or other fumarate esters, acids, salts, or derivatives thereof, and combinations or mixtures of any of the foregoing.

The terms "active ingredient" or "active pharmaceutical ingredient" as used herein refer to a pharmaceutical agent, active ingredient, compound, or substance, compositions, or mixtures thereof, that provide a pharmacological, often beneficial, effect.

The terms "dosage" or "dose" as used herein denote any form of the active ingredient formulation that contains an amount sufficient to produce a therapeutic effect with a single administration. The dosage form used herein is for oral administration. The preferred oral dosage forms are soft capsules, or preferably, enteric soft capsules.

The terms "active pharmaceutical ingredient load" or "drug load" as used herein refers to the quantity (mass) of the active pharmaceutical ingredient comprised in a single soft capsule fill.

The term "formulation" or "composition" as used herein refers to the drug in combination with pharmaceutically acceptable excipients. This term includes orally administrable formulations as well as formulations administrable by other means.

The term "titration" as used herein refers to the incremental increase in drug dosage to a level that provides the optimal therapeutic effect.

The term "controlled release" as used herein refers to a composition that does not immediately releases an active ingredient. "Controlled release" as used herein encompasses the terms "modified release," "sustained release," "extended release," and "delayed release."

The term "delayed release" as used herein refers to a composition that releases an active ingredient according to a desired profile over an extended period under physiological conditions or in an in vitro test. By "extended period" it is meant a continuous period of time of at least about 20 minutes, about 30 minutes, about 1 hour; about 2 hours; about 4 hours; about 6 hours; about 8 hours; about 10 hours; about 12 hours; about 14 hours; about 16 hours; about 18 hours; about 20 hours about 24 hours; or even longer.

The term "modified release" as used herein refers to a composition that releases an active ingredient at a slower rate than does an immediate release formulation under physiological conditions or in an in vitro test.

The term "sustained" release as used herein refers to a composition that releases an active ingredient over an extended period of time, for example minutes, hours, or days, such that less than all the active ingredient is released initially. A sustained release rate may provide, for example, a release of a certain specified amount of a drug or active ingredient from a dosage form, over a certain period, under physiological conditions or in an in vitro test.

The term "extended release" as used herein refers to a composition that releases an active ingredient over an extended period, such as of at least about 20 minutes, about 30 minutes, about 1 hour; about 2 hours; about 4 hours; about 6 hours; about 8 hours; about 10 hours; about 12 hours; about 14 hours; about 16 hours; about 18 hours; about 20 hours about 24 hours; or even longer; specifically, over a period of at least 18 hours under physiological conditions or in an in vitro assay.

The term "$C_{max}$" as used herein refers to the maximum observed blood (plasma, serum, or whole blood) concentration or the maximum blood concentration calculated or estimated from a concentration to time curve, and is expressed in units of mg/L or ng/mL, as applicable.

The term "$C_{min}$" as used herein refers to the minimum observed blood (plasma, serum, or whole blood) concentration or the minimum blood concentration calculated or estimated from a concentration to time curve, and is expressed in units of mg/L or ng/mL, as applicable.

The term "$C_{avg}$" as used herein refers to the blood (plasma, serum, or whole blood) concentration of the drug within the dosing interval, is calculated as AUC/dosing interval, and is expressed in units of mg/L or ng/mL, as applicable.

The term "$T_{max}$" as used herein refers to the time after administration at which $C_{max}$ occurs, and is expressed in units of hours (h) or minutes (min), as applicable.

The term "$AUC_{0 \to \tau}$" as used herein refers to area under the blood (plasma, serum, or whole blood) concentration versus time curve from time zero to time tau ($\tau$) over a dosing interval at steady state, where tau is the length of the dosing interval, and is expressed in units of h·mg/L or h·ng/mL, as applicable. For example, the term $AUC_{0 \to 12}$ as used herein refers to the area under the concentration versus time curve from 0 to 12 hours.

The term "$AUC_{0 \to \infty}$" as used herein refers to the area under the blood (plasma, serum, or whole blood) concentration versus time curve from time 0 hours to infinity, and is expressed in units of h·mg/L or h·ng/mL, as applicable.

The term "$AUC_{overall}$" as used herein refers to the combined area under the blood (plasma, serum, or whole blood) concentration versus time curve, and is expressed in units of h·mg/L (or h·ng/mL) for at least one or more doses of the pharmaceutical compositions described herein. In one aspect, the "$AUC_{overall}$" refers to the combined area under the blood concentration versus time curve for at least two doses of the pharmaceutical compositions described herein.

The term "treating" refers to administering a therapy in an amount, manner, or mode effective to improve a condition, symptom, or parameter associated with a disorder.

The term "prophylaxis" refers to preventing or reducing the progression of a disorder, either to a statistically significant degree or to a degree detectable to one skilled in the art.

The term "substantially" as used herein means to a great or significant extent, but not completely.

The term "about" as used herein refers to any value that is within a variation of up to ±10% of the value modified by the term "about."

As used herein, "a" or "an" means one or more unless otherwise specified.

Terms such as "include," "including," "contain," "containing" and the like mean "comprising."

The term "or" can be conjunctive or disjunctive.

One embodiment described herein, is controlled release pharmaceutical composition comprising an enteric soft capsule comprising a matrix comprising fumarate esters.

In another embodiment, the enteric soft capsule provides controlled release properties.

In another embodiment, the matrix fill provides controlled release properties. Such controlled release matrix fills are described in International Patent Application Publication No. WO 2005/009409; U.S. Patent Application Publication No. US 2006/0115527; U.S. Pat. Nos. 8,293,270; and 8,333,989, each of which are incorporated by reference herein for such teachings. In one aspect, the matrix is configured to provide controlled release, extended release, sustained release, delayed release, or combinations thereof.

In another embodiment, the matrix comprises a lipid or lipophilic vehicle that provides a suspension of fumarate ester microparticles having defined sizes. In one aspect, an enteric soft capsule comprising a suspension of fumarate ester microparticles provides controlled release delivery of the fumarate ester.

In another embodiment, the pharmaceutical composition comprises matrix fills for fumarate esters, such as dimethyl fumarate, monomethyl fumarate, or derivatives thereof, based on lipids or lipophilic vehicles. The described matrices have a hydrophobic (lipophilic) surface in contact with the hydrophilic soft enteric capsule shell to minimize any potential shell-fill interactions, such as when enteric soft capsules are filled with hydrophilic vehicles.

Described herein are methods for manufacturing matrix fills comprising fumarate esters, such as dimethyl fumarate, monomethyl fumarate, or derivatives thereof, in a controlled release enteric soft capsule in the form of a suspension, where part or all of the fumarate ester is suspended within the matrix. Also provided are compositions and formulations where the fumarate ester is incorporated into a one-phase or two-phase matrix.

Also described herein are methods for manufacturing matrix fills comprising fumarate esters or derivatives thereof, in a delayed release enteric soft capsule in the form of a suspension, where part or all of the fumarate ester is suspended within the matrix.

Described herein are methods for manufacturing matrix fills comprising fumarate esters or derivatives thereof, in an extended release enteric soft capsule in the form of a suspension, where part or all of the fumarate ester is suspended within the matrix.

Another embodiment described herein is a controlled, delayed, or extended release enteric soft capsule having a shell and a matrix fill, wherein the matrix fill includes fumarate esters such as dimethyl fumarate, monomethyl fumarate, or derivatives thereof, suspended as solid particles in a lipid or lipophilic vehicle. In another embodiment, the lipid or lipophilic vehicle comprises a vegetable oil, hydrogenated vegetable oil, fatty acid, wax, fatty acid ester, or a combination thereof.

Exemplary lipid or lipophilic vehicles comprise mineral oil; light mineral oil; natural oils (e.g., vegetable, corn, canola, sunflower, soybean, olive, coconut, cocoa, peanut, almond, cottonseed, persic, sesame, squalane, castor, cod liver) hydrogenated vegetable oil; partially hydrogenated oils; beeswax; polyethoxylated beeswax; paraffin; normal waxes; medium chain medium chain monoglycerides, diglycerides and triglycerides; higher aliphatic alcohols; higher aliphatic acids; long chain fatty acids; saturated or unsaturated fatty acids; hydrogenated fatty acids; fatty acid glycerides; polyoxyethylated oleic glycerides; monoglycerides and diglycerides; mono-, bi- or tri-substituted glycerides; glycerol mono-oleate esters; glycerol mono-caprate; glyceryl monocaprylate; propylene glycol dicaprylate; propylene glycol monolaurate; glyceryl palmitostearate; glyceryl behenate; diethyleneglycol palmitostearate; polyethyleneglycol stearate; polyoxyethyleneglycol palmitostearate; glyceryl mono palmitostearate; cetyl palmitate; polyethyleneglycol palmitostearate; dimethylpolysiloxane; mono- or di-glyceryl behenate; fatty alcohols associated with polyethoxylate fatty alcohols; cetyl alcohol; octyl dodecanol; myristyl alcohol; isopropyl myristate, isopropyl palmitate, stearic acid, or stearyl alcohol, inter alia, or combinations thereof.

In one embodiment, the matrix comprises a solvent or solubility enhancing agent. Exemplary solvents or solubility enhancing agents useful for the matrix fills described herein include Capmul® MCM, Captex® 355, Cremophor® RH 40, Croscarmellose, Crospovidone, Crospovidone CL, Crospovidone CL-F, Crospovidone CL-M, Imwitor® 742, Kollidon® CL, Kollidon® CL-F, Kollidon® CL-M, Labrafac™ Lipophile WL 1349, Labrafil® M2125CS, Labrasol®, Lutrol® F 68, Maisine™ 35-1, mannitol, Miglyol® 812, Pearlitol® Flash, Peceol®, polyethylene glycol 400, polyethylene glycol 600, polyethylene glycol 3350, Plurol® Oleique CC 497, Povidone K 17, Povidone K 30, propylene glycol, or combinations thereof.

In one embodiment, the matrix comprises solid particles of fumarate ester suspended in a lipid or lipophilic vehicle of vegetable oil, hydrogenated vegetable oil, fatty acid, fatty acid ester, or a combination thereof. The matrix can also comprise solvents and suspension agents such as polyethylene glycols of molecular weight ranging from about 200 to about 8000, polyvinylpyrrolidone, or combinations thereof.

In another embodiment, the matrix fill comprises a release regulator such as a fatty acid salt, fatty acid ester, or fatty acid polyoxyethylene derivative. The release regulator can also be a surfactant having a hydrophilic/lipophilic balance (HLB) value between about 2 and about 40. The HLB characteristic of surfactants can be determined in accordance with "*Physical Pharmacy: Physical Chemical Principles in the Pharmaceutical Sciences*," Fourth Edition, pp. 371-373, A. Martin, Ed., Lippincott Williams & Wilkins, Philadelphia (1993), which is incorporated by reference herein for such teachings.

In another embodiment, the matrix comprises emulsifying or solubilizing agents such as acacia, cholesterol, diethanolamine, glyceryl monostearate, lanolin alcohols, lecithin, mono- and di-glycerides, monoethanolamines, oleic acids, oleyl alcohols, poloxamer, polyoxyethylene 50 stearate, polyoxyl 35 castor oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, sorbitan monooleate, sorbitan monopalmitate, sorbitan monostearate, stearic acid, trolamine, emulsifying wax, or combinations thereof.

In another embodiment, the matrix comprises a neutralizing agent. Without being bound to any theory, the neutralizing agent stabilizes the fumarate ester in the matrix fill by preventing hydrolysis. In addition, without being bound by any theory, the neutralizing agent stabilizes the enteric soft capsule shell by forming salts with the methylacrylate moieties from the capsule shell. In one aspect, the neutralizing agent comprises an organic acid, ester, or salt. In another aspect, the neutralizing agent comprises at least one of lactate, fumarate, caprylate, caprate, oleate, maleate, succinate, tartrate, citrate, glutamate, gluconate, esters or salts thereof, or combinations thereof. In one aspect, the neutralizing agent is lactic acid.

In another embodiment, the matrix includes a hydrophilic internal phase and a lipid or lipophilic external phase. The hydrophilic internal phase comprises polypropylene glycol or polyethylene glycol of molecular weight ranging from about 200 to about 8000. In another embodiment, the internal phase comprises hydroalcoholic solutions of cellulose derivatives, polyacrylates, polyvinyl polymers, or combinations thereof. In one embodiment, the internal phase comprises polymers such as methylcellulose, hydroxypropylmethylcellulose, polymethylmethacrylate, or polyvinylpyrrolidone (PVP). In one embodiment, the internal phase of the matrix state is "fluid" or "structured." A "fluid" internal phase, as used herein, means a completely flowable liquid whose globules can aggregate to make a larger globule. A "structured" internal phase, as used herein, means a solid, semisolid, or a gel whose shape is relatively stable and does not usually aggregate to form a large globule. A structured internal phase can provide controlled drug release and stabilize the physical state of the matrix. Without being bound to any theory, the structured nature of the matrix impedes solvation or diffusion of the fumarate ester out of the matrix. In another embodiment, the external phase comprises a vegetable oil, hydrogenated vegetable oil, fatty acid, fatty acid ester, wax, or a combination thereof. In another embodiment, fumarate ester is dispersed in the internal phase as a suspension form.

In another embodiment, the matrix fill is of an emulsion type, where the fumarate ester is distributed in one or both of the external (lipophilic and internal phases. The external phase of the emulsion matrix fill comprises lipid or lipophilic vehicles similar to those described herein. The fumarate ester can be dispersed in the internal phase as a solution or as a suspension. For example, one portion of the fumarate ester in the form of a powder is incorporated in the internal phase, while another portion is dispersed in the external phase as solid particles. An emulsion-type matrix may comprise a surfactant or combination of surfactants having HLB values ranging from about 2 to about 40, including all integers within the specified range. In one aspect, the HLB range comprises from about 8 to about 20, including all integers within the specified range.

In one embodiment, the pharmaceutical composition described herein comprises an enteric soft capsule comprising a matrix comprising a lipid or lipophilic vehicle that provides a suspension of a fumarate ester. In one embodiment described herein, the fumarate ester is a dialkyl fumarate of Formula I:

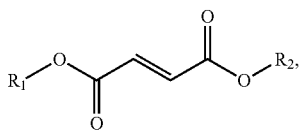

wherein $R_1$ and $R_2$, which may be the same or different, independently represent hydrogen or a linear, branched or cyclic, saturated or unsaturated $C_{1-20}$ alkyl radical, which may be optionally substituted with halogen (Cl, F, I, Br), hydroxy, $C_{1-4}$ alkoxy, nitro, or cyano for preparing a pharmaceutical composition as described herein.

The $C_{1-20}$ alkyl radicals, $C_{1-8}$ alkyl radicals, and $C_{4-5}$ alkyl radicals are, for example, methyl, ethyl, n-propyl, isopropyl, n-butyl, sec-butyl, t-butyl, pentyl, cyclopentyl, 2-ethyl hexyl, hexyl, cyclohexyl, heptyl, cycloheptyl, octyl, vinyl, allyl, 2-hydroxyethyl, 2 or 3-hydroxy propyl, 2-methoxy ethyl, methoxy methyl or 2- or 3-methoxy propyl. In one aspect, at least one of $R_1$ or $R_2$ is a $C_{1-5}$ alkyl, especially methyl or ethyl. In another aspect, $R_1$ and $R_2$ are the same or different $C_{1-5}$ alkyl radicals such as methyl, ethyl, n-propyl, or t-butyl. In one aspect, $R_1$ and $R_2$ are the same or different $C_{1-5}$ alkyl radicals such as methyl and ethyl. In one aspect, $R_1$ and $R_2$ are identical and are methyl or ethyl. In one aspect, the fumarate ester is monomethyl fumarate, dimethyl fumarate, methyl ethyl fumarate, or diethyl fumarate. In one aspect, the fumarate ester is monomethyl fumarate, dimethyl fumarate, or a combination thereof. In one aspect, the fumarate ester is monomethyl fumarate. In another aspect, the fumarate ester is dimethyl fumarate.

In one embodiment, the pharmaceutical compositions described herein may comprise pharmaceutically acceptable salts of the active ingredient. The term "pharmaceutically acceptable salts" of an active ingredient includes alkali metal salts such as, sodium or potassium salts, alkaline earth metal salts such as, for example, calcium and magnesium salts, and salts with organic or inorganic acid such as, for example, hydrochloric acid, hydrobromic acid, nitric acid, sulfuric acid, phosphoric acid, citric acid, formic acid, maleic acid, succinic acid, tartaric acid, methanesulphonic acid, toluenesulphonic acid, inter alia. In another embodiment, the active ingredient may also be in the form of pharmaceutically acceptable uncharged or charged molecules, molecular complexes, solvates, or anhydrates thereof, and, if relevant, single isomers, enantiomers, racemic mixtures, or mixtures thereof. In another embodiment, the active pharmaceutical ingredient may be in any of its crystalline, polymorphous, semi-crystalline, amorphous or polyamorphous forms, or mixtures thereof.

The fumarate esters described herein can be prepared by processes known in the art. See, e.g., EP 0 312 697 and U.S. Patent Application Publication Nos. US 2013/0295169; US 2014/0179779; and US 2014/0200363, each of which is incorporated by reference herein for such teachings.

In one embodiment, the pharmaceutical composition comprises an active ingredient or drug. In one embodiment, the active ingredient or drug is a pharmacologically active fumarate ester. In one embodiment described herein, the active ingredient is a dialkyl fumarate. In one embodiment described herein, the active ingredient is a fumarate ester or combination of fumarate esters. In one embodiment described herein, the active ingredient is dimethyl fumarate. In another embodiment described herein, the active ingredient is monomethyl fumarate. In another embodiment described herein, the active ingredient is a combination of dimethyl fumarate and monomethyl fumarate. In another embodiment described herein, the active ingredient is a combination of dimethyl fumarate, monomethyl fumarate, and other pharmacologically active fumarate esters, acids, salts, or derivatives thereof. In another embodiment, the active ingredient or drug comprises dimethyl fumarate, monomethyl fumarate, other pharmacologically active fumarate esters, acids, or salts, derivatives thereof, or combinations thereof. In another embodiment, the active ingredient comprises dimethyl fumarate, monomethyl fumarate, or derivatives thereof, combined with aspirin, ibuprofen, naproxene, diclofenac, ketoprofen, celecoxib, other non-steroidal anti-inflammatory active drugs (NSAIDs), or combinations thereof. In one embodiment, the pharmaceutical composition comprises a fumarate ester combined with aspirin.

In another embodiment, the pharmaceutical composition comprises a fumarate ester combined with one or more leukotriene receptor antagonists. In another embodiment, the pharmaceutical composition comprises a fumarate ester combined with montelukast (Singulair®) or zafirlukast (Accolate®). In another embodiment, the pharmaceutical composition comprises a fumarate ester combined with montelukast or zafirlukast and an NSAID. In another embodiment, the pharmaceutical composition comprises a fumarate ester combined with montelukast or zafirlukast and aspirin.

In one embodiment, the fumarate ester-to-matrix ratio range comprises from about 1:50 to about 1:1 by weight, including all ratios within the specified range. In another embodiment, the fumarate ester-to-matrix ratio range comprises from about 1:10 to about 1:1 by weight, including all ratios within the specified range. In one aspect, the fumarate ester-to-matrix ratio comprises about 1:9 to about 1:1 by weight, including all ratios within the specified range. In another aspect, the fumarate ester-to-matrix ratio range comprises from about 1:5 to about 1:1 by weight, including all ratios within the specified range. In another aspect, the fumarate ester-to-matrix ratio is about 1:5; about 1:4; about 1:3; about 1:2; about 1:1; or about 0.5:1. In other aspects, the fumarate ester-to-matrix ratio is 1:3.5; 1:3.1; 1:2.9; 1:2.3; or 1:1.5.

In one embodiment, the active ingredient comprises about 1% to about 70% of the matrix, including each integer within the specified range. In another embodiment, the active ingredient comprises about 70%, about 60%, about 50%, about 40% about 30%, about 20%; about 15%; about 10%; about 5%; about 2%, or about 1% of the matrix. In one aspect, the active ingredient comprises about 64% of the matrix. In another embodiment, the active ingredient comprises about 57% of the matrix. In another embodiment, the active ingredient comprises about 50% of the matrix. In another embodiment, the active ingredient comprises about 32% of the matrix. In another embodiment, the active ingredient comprises about 30% of the matrix. In another embodiment, the active ingredient comprises about 25% of the matrix.

In one embodiment, the solid fumarate ester particles are milled or micronized. In one embodiment, the fumarate ester comprises a particle size range of about 1 to about 500 µm, including each integer within the specified range. In one aspect, the micronized solid fumarate ester particles have mean particle distributions of about 1 µm, 2 µm, about 5 µm, about 10 µm, about 15 µm, about 20 µm, about 25 µm, about 30 µm, about 35 µm, about 40 µm, about 45 µm, about 50 µm, about 55 µm, about 60 µm, about 65 µm, about 70 µm, about 75 µm, about 80 µm, about 85 µm, about 90 µm, about 95 µm, about 100 µm, about 105 µm, about 110 µm, about 115 µm, about 120 µm, about 125 µm, about 130 µm, about 135 µm, about 140 µm, about 145 µm, about 150 µm, about 155 µm, about 160 µm, about 165 µm, about 170 µm, about 175 µm, about 180 µm, about 185 µm, about 190 µm, about 195 µm, about 200 µm, about 205 µm, about 210 µm, about 215 µm, about 220 µm, about 225 µm, about 230 µm, about 235 µm, about 240 µm, about 245 µm, about 250 µm, about 255 µm, about 260 µm, about 265 µm, about 270 µm, about 275 µm, about 280 µm, about 285 µm, about 290 µm, about 295 µm, about 300 µm, about 305 µm, about 310 µm, about 315 µm, about 320 µm, about 325 µm, about 330 µm, about 335 µm, about 340 µm, about 345 µm, about 350 µm, about 355 µm, about 360 µm, about 365 µm, about 370 µm, about 375 µm, about 380 µm, about 385 µm, about 390 µm, about 395 µm, about 400 µm, about 405 µm, about 410 µm, about 415 µm, about 420 µm, about 425 µm, about 430 µm, about 435 µm, about 440 µm, about 445 µm, about 450 µm, about 455 µm, about 460 µm, about 465 µm, about 470 µm, about 475 µm, about 480 µm, about 485 µm, about 490 µm, about 495 µm, about 500 µm, or even larger. In another aspect, the solid particles of fumarate ester comprise a distribution of particle sizes, comprising particles of any of the foregoing sizes.

In another embodiment, the solid fumarate ester particles have mean particle size distributions (PSD) of about 20 µm to about 300 µm, including each integer within the specified range. In one aspect, the solid particles of fumarate ester comprise mean particle size distributions of about 20 µm, about 30 µm, about 50 µm, 60 µm, about 70 µm, about 80 µm, about 90 µm, about 100 µm, about 120 µm, about 140 µm, about 160 µm, about 180 µm, about 190 µm, about 200 µm, about 220 µm, about 240 µm, about 260 µm, about 280 µm, or about 300 µm. In one aspect, the solid particles of fumarate ester have a mean particle size distribution of about 260 µm. In one aspect, the solid particles of fumarate ester have a mean particle size distribution of about 170 µm. In one aspect, the solid particles of fumarate ester have a mean particle size distribution of about 140 µm. In one aspect, the solid particles of fumarate ester have a mean particle size distribution of about 90 µm. In one aspect, the solid particles of fumarate ester have a mean particle size distribution of about 80 µm. In one aspect, the solid particles of fumarate ester have a mean particle size distribution of about 25 µm. In another aspect, the plurality of mean particle size distributions can comprise particles of about 261 µm, about 168 µm, about 148 µm, about 90 µm, about 80 µm, or about 26 µm. In another aspect, the solid particles of fumarate ester have a mean particle size distribution of less than or equal to about 90 µm. In one aspect, the solid particles of fumarate ester comprise a d90 of less than or equal to about 90 µm (d90≤90 µm).

In another embodiment, the solid particles of fumarate ester comprise multiple distributions of particle sizes. In one aspect, the solid particles of fumarate ester may comprise a plurality of mean particle size distributions of from about 20 µm to about 300 µm. In another aspect, the plurality of mean particle size distributions can comprise combinations of about 261 µm, about 168 µm, about 150 µm, about 90 µm, about 80 µm, or about 26 µm. In another aspect, the solid particles of fumarate ester comprise a plurality of mean particle size distributions of about 30 µm to about 260 µm in a single matrix fill. Any of the foregoing fumarate ester particle size distributions may be combined to provide the desired controlled release profile.

Another embodiment described herein is a method for manufacturing a matrix fill for a controlled release soft enteric capsule comprising particles of fumarate esters such as dimethyl fumarate or monomethyl fumarate of defined sizes. In one aspect, the particles are of a similar size distribution. In another aspect, the fumarate ester particles comprise varied size distributions. In another aspect, the fumarate ester particles comprise several size distributions. In another aspect, the fumarate ester particles comprise a mixture of smaller and larger size distributions. Without being bound to any theory, smaller particles are generally solubilized and released more rapidly than larger particles. The release rate can be adjusted to achieve a specific therapeutic window over a defined period and produce controlled release, delayed release, or extended release compositions by combining multiple fumarate ester particle distributions.

Another embodiment described herein is a method for manufacturing a pharmaceutical composition comprising fumarate ester(s) where the fumarate ester does not sublime during processing, manufacturing, after production, or during storage. Soft enteric capsules comprising fumarate ester in the matrix fills described herein are stable for months or years. Without being bound to any theory, it is believed that suspending solid fumarate ester in a lipid or lipophilic vehicle comprising an organic acid prevents or retards sublimation and stabilizes the fumarate ester. In one aspect, the pharmaceutical compositions described herein are stable at 25° C. and 60% relative humidity (RH) for about 1 month, about 2 months, about 3 months, about 4 months, about 5 months, about 6 months, about 9 months, about 10 months, about 11 months, about 12 months, or even longer. In another aspect, the pharmaceutical compositions described herein are stable for 1 year or longer at 25° C. and 60% RH. In another aspect, the pharmaceutical compositions described herein are stable for 2 years or longer at 25° C. and 60% RH.

Another embodiment described herein is a method for preparing a pharmaceutical matrix comprising a fumarate ester. An exemplary scheme of a manufacturing process is shown in FIG. 1. The method comprises applying heat to the matrix components during mixing or prior to mixing at about the melting point of the matrix fill composition; and then mixing the fumarate ester with the lipid or lipophilic matrix ingredients using mechanical or ultrasonic forces to form the matrix fill. The matrix fill is flowable such that it can be encapsulated using a rotary die encapsulation machine. In one embodiment, the matrix components are heated to a temperature in the range of from about 25° C. to about 70° C. The matrix components are heated to a temperature in the range of from about 25° C. to about 30° C.

In one embodiment, the matrix comprises a lipid or lipophilic vehicle, a neutralizing agent, excipients, and sold particles of fumarate ester. In another aspect, the matrix comprises polyethylene glycols, polyvinylpyrrolidones, oils, and surfactants. In one aspect, the surfactant comprises polysorbate 80 or polyoxyl 40 hydrogenated castor oil. In another aspect, the matrix comprises dimethyl fumarate, a mixture of mono- and di-glycerides, polyvinylpyrrolidone, polyoxyl 40 hydrogenated castor oil, and lactic acid.

In one embodiment, the matrix comprising fumarate ester comprises the composition shown in Table 1 including all possible iterations of the specified ranges that provide 100% for the total weight percentage of the composition.

TABLE 1

Exemplary Matrix Fill Composition

| Ingredient | mg/capsule | % weight |
| --- | --- | --- |
| Dimethyl Fumarate (PSD 80 µm) | 240 | 32 |
| Capmul ® MCM | 375 | 50 |
| Povidone K 30 | 15-52.5 | 0.01-7 |
| Cremophor ® RH 40 | 15-75 | 2-10 |
| Lactic acid | 7.5-37.5 | 1-5 |
| TOTAL | 750 mg | 100% |

In one embodiment, the matrix comprises about 32% of fumarate ester (PSD: 80 µm); about 50% of a mixture of mono- and di-glycerides; at least about 0.01-7% polyvinylpyrrolidone; at least about 2-10% polyoxyl 40 hydrogenated castor oil, and at least about 1-5% lactic acid, including all iterations of the specified ranges. In one aspect, the composition prevents sublimation of the FAE during processing and manufacturing. In one aspect, the composition reduces the onset of symptoms of gastrointestinal side effects. In another aspect, the composition is stable for at least 6 months at 25° C. at 60% relative humidity. In another aspect, the composition is stable for at least 24 months.

In one embodiment, the matrix comprises the composition shown in Table 2 including all possible iterations of the specified ranges that provide 100% for the total weight percentage.

TABLE 2

Exemplary Matrix Fill Composition

| Ingredient | mg/capsule | % weight |
| --- | --- | --- |
| Monomethyl fumarate PSD: d90 ≤ 90 µm | 480 | 48-60 |
| Capmul ® MCM | 216-470 | 25-48.0 |
| Cremophor ® RH 40 | 7.3-120 | 0.85-12.0 |
| Povidone K 30 | 7.3-50 | 0.85-5.0 |
| Lactic acid | 21.7-50 | 2.55-5.0 |
| TOTAL | 850 mg-1000 mg | 100% |

In another embodiment the matrix fill comprises about 32% of fumarate ester (PSD: ≤90 µm); about 25% to about 47% of a mixture of mono- and di-glycerides; at least about 0.01-7% polyvinylpyrrolidone; at least about 0.85-12% polyoxyl 40 hydrogenated castor oil, and at least about 1-5% lactic acid, including all iterations of the specified ranges. In one aspect, the composition prevents sublimation of the FAE during processing and manufacturing. In another aspect, the composition reduces the onset of symptoms of any gastrointestinal side effects. In another aspect, the composition is stable for at least 6 months at 25° C. at 60% relative humidity. In another aspect, the composition is stable for at least 24 months at 25° C. at 60% relative humidity.

In one embodiment, the fumarate ester pharmaceutical composition comprises a soft gelatin capsule shell comprising a matrix comprising a fumarate ester.

In one embodiment, the fumarate ester pharmaceutical composition comprises an enteric soft capsule shell comprising a matrix comprising a fumarate ester. Enteric soft capsules are described in International Patent Application Publication No. WO 2004/030658; U.S. Patent Application Publication No. US 2006/0165778; and U.S. Pat. No. 8,685,445, each of which is incorporated by reference herein for such teachings. The enteric soft capsule shell may comprise one or more film forming polymers, one or more enteric acid-insoluble polymers, one or more plasticizers, one or more alkali-neutralizing agents, one or more solvents, optionally one or more colorants, and optionally one or more flavorings or other conventionally accepted pharmaceutical excipients or additives.

Film-former polymers that are useful for creating enteric soft capsules are gelatin or hydroxypropylmethylcellulose (HPMC). In one aspect of the enteric soft capsule shell described herein, the film-forming polymer is gelatin.

Examples of enteric, acid-insoluble polymers are acrylic and methacrylate acid copolymers, cellulose acetate phthalate (CAP), cellulose acetate butyrate, hydroxypropylmethylcellulose phthalate (HPMCP), algenic acid salts such as sodium or potassium alginate, or shellac. Poly(methacylic acid-co-methyl methacrylate) anionic copolymers based on methacrylic acid and methyl methacrylate are particularly stable and are preferred in some embodiments. Poly(meth)acrylates (methacrylic acid copolymer), available under the trade name EUDRAGIT® (Evonik Industries AG, Essen, Germany), are provided as powder or aqueous dispersions. In another aspect, the methacrylic acid copolymer comprises EUDRAGIT® L 30 D-55; EUDRAGIT® L 100-55; EUDRAGIT® L 100; EUDRAGIT® L 12.5; EUDRAGIT® S 100; EUDRAGIT® S 12.5; EUDRAGIT® FS 30 D; EUDRAGIT® E 100; EUDRAGIT® E 12.5; EUDRAGIT® E PO; EUDRAGIT® RL 100; EUDRAGIT® RL PO; EUDRAGIT® RL 30 D; EUDRAGIT® RL 12.5; EUDRAGIT® RS 100; EUDRAGIT® RS PO; EUDRAGIT® RS 30 D; EUDRAGIT® RS 12.5; EUDRAGIT® NE 30 D; EUDRAGIT® NE 40 D; EUDRAGIT® NM 30 D; other poly(meth)acrylate polymers; or a mixture thereof. In one aspect, the enteric polymer is EUDRAGIT® L 100, a methacrylic acid copolymer, Type A. Acid-insoluble polymer specifications are detailed in the United States Pharmacopoeia and in various monographs.

In another embodiment described herein, the enteric polymer in the enteric soft capsule shell comprises poly(methacylic acid-co-ethyl acrylate) 1:1 (e.g., EUDRAGIT® L 100-55). In one embodiment described herein, the enteric polymer comprises poly(ethyl acrylate-co-methyl methacrylate) 2:1 (e.g., EUDRAGIT® NE 40 D). In another embodiment described herein, the enteric polymer comprises poly (methyl acrylate-co-methyl methacrylate-co-methacrylic acid) 7:3:1 (e.g., EUDRAGIT® FS 30 D). In another embodiment described herein, the enteric polymer comprises a combination of poly(methacylic acid-co-ethyl acrylate) 1:1 and poly(methyl acrylate-co-methyl methacrylate-co-methacrylic acid) 7:3:1. In another embodiment, the enteric polymer comprises a combination of poly(methacylic acid-co-ethyl acrylate) 1:1 and poly(ethyl acrylate-co-methyl methacrylate) 2:1. In another embodiment, the enteric polymer comprises a combination of poly(methacylic acid-co-ethyl acrylate) 1:1, poly(ethyl acrylate-co-methyl methacrylate) 2:1, and poly(methyl acrylate-co-methyl methacrylate-co-methacrylic acid) 7:3:1.

In another embodiment, plasticizers that are useful for creating enteric soft capsules as described herein are glycerol, sorbitol, polyethylene glycol, citric acid, citric acid esters, such as tri-ethyl citrate, or combinations thereof. The weight ratio between the film-forming polymer, the enteric acid-insoluble polymer, and plasticizer is adjusted so that the gel mass is flowable and not too viscous, and can be made into soft capsules using rotary die encapsulation methods.

In one embodiment, enteric soft capsule shell compositions are made by dissolving the enteric acid-insoluble polymer in an aqueous solution of an alkali-neutralizing agent such as ammonia, sodium hydroxide, potassium hydroxide, or liquid amines such as tri-ethanol amine or ethylene diamine. The amount of alkali is adjusted to give a final pH value of the gel mass less than or equal to about pH 9.0. In one embodiment, the final pH does not exceed 8.5. The volatile alkali-neutralizing agent, ammonia is preferred. The film-forming polymer can then be combined with the plasticizer and solvent and then blended with the acid-insoluble gel to make a final homogeneous mix in a heat-controlled vessel with degassing by vacuum. The fugitive ammonia evaporates during degassing. Using the foregoing process, the alkali concentrations do not require heating or neutralizing with acid in order to neutralize the gel mass.

In another embodiment described herein, the enteric soft capsule shell is made using an aqueous dispersion of the acid-insoluble polymer by adding an alkali-neutralizing agent such as ammonium, sodium, or potassium hydroxides, other alkalis, or a combination thereof that will cause the enteric acid-insoluble polymer to dissolve. The plasticizer-wetted, film-forming polymer can then be mixed with the solution of the acid-insoluble polymer. In one embodiment, enteric acid-insoluble polymers in the form of salts of the bases or alkalis as described herein are dissolved directly in water and mixed with the plasticizer-wetted, film-forming polymer.

In one embodiment described herein, enteric acid-insoluble polymers in the form of salts of the bases or alkalis described herein are dissolved directly in water and mixed with the plasticizer-wetted, film-forming polymer. In another embodiment described herein, an aqueous dispersion of the acid-insoluble polymer or polymers is used, which obviates the need for the addition of the alkali-neutralizing agent described herein.

In one embodiment, the enteric soft capsule shell has the composition of Table 3, including all possible iterations of the specified ranges that provide 100% for the total weight percentage, including or excluding the optional, excipients, opacifiers, colorants, and flavorings.

TABLE 3

Enteric Soft Capsule Shell Composition

| Component | Exemplary Component | Composition Range (%) |
| --- | --- | --- |
| Film-forming polymer | Gelatin | 20-36 |
| Enteric, acid-insoluble polymer | Methacrylic Acid Copolymer | 8-20 |
| Plasticizer | Glycerol, Triethyl citrate | 15-22 |
| Alkali-neutralizing agents | NH$_4$OH (30%), NaOH | 1-5 |
| Solvent | Water | 20-40 |
| Opacifier | Titanium Dioxide | 1-7.5 |
| Colorant (optional) | Various | 0.05-1 |
| Flavoring (optional) | Various | 0.05-2 |
| Excipients (optional) | Various | 1-5 |

In one embodiment, the enteric soft capsule shell comprises a composition of about 30% film forming polymer; about 10% enteric, acid-insoluble polymer; about 20% plasticizer; about 1% alkali-neutralizing agent; and about 37% solvent.

In another embodiment, the weight percentage range of total polymer content (i.e., film forming polymer and enteric acid-insoluble polymer) of the enteric soft capsule described herein is about 30% to about 45%, including all integers within the specified range. In one aspect, the total polymer weight percentage is about 40%. In another aspect, the total polymer weight percentage is about 42%. In another aspect, the total polymer weight percentage is about 45%. In another aspect, the total polymer weight percentage is about 38%.

In one embodiment, the weight percentage range of total plasticizer is about 15% to about 22%, including all iterations of integers with the specified range. In one aspect, the total plasticizer weight percentage is about 19%. In another aspect, the total plasticizer weight percentage is about 17.7%. In another aspect, the total plasticizer weight percentage is about 18.9%. In another aspect, the total plasticizer weight percentage is about 19.3%.

In one embodiment, the alkali-neutralizing agent is ammonia (ammonium hydroxide; 30% w/v) that is added to comprise a weight percentage of about 1 to about 5% of the total enteric soft capsule composition. In one aspect, 30% w/v ammonia is added to comprise a weight percentage of about 2%. In another aspect, 30% w/v ammonia is added to a weight percentage of about 1.7%. In one aspect, ammonia is added to provide a final pH of about 9 in the enteric soft capsule composition. In another aspect, ammonia is added to provide a final pH of about 8.5 in the enteric soft capsule composition. In another aspect, after the capsules are filled and dried, the ammonia concentration is substantially reduced, owing to the fugitive nature of the volatile alkali-neutralizing agent. In another aspect, practically all of the ammonia is evaporated except for ammonium ions comprising salts with other moieties in the composition.

In one embodiment, the weight ratio range of film forming polymer to enteric acid-insoluble polymer (i.e., film forming:enteric) is about 25:75 (≈0.33) to about 40:60 (≈0.67) (i.e., ≈0.33-0.67), including all ratios within the specified range. In one aspect, the ratio of film forming polymer to enteric acid-insoluble polymer is about 30:70 (≈0.43). In another aspect, the ratio of film forming polymer to enteric acid-insoluble polymer is about 28:72 (≈0.38).

In one embodiment, the weight ratio of total plasticizer to film forming polymer is about 20:40 to 21:30 (i.e., ≈0.5-0.7), including all ratios within the specified range. In one aspect, the weight ratio of total plasticizer to film forming polymer is about 20:40 (≈0.5). In another aspect, the weight ratio of total plasticizer to film forming polymer is about 21:30 (≈0.7). In another aspect, the weight ratio of total plasticizer to film forming polymer is about 19:29 (≈0.65). In another aspect, the weight ratio of total plasticizer to film forming polymer is about 19.3:29.2 (≈0.66).

In one embodiment, the weight ratio of total plasticizer to enteric acid-insoluble polymer is about 1:1 to about 2:1 (≈1-2), including all ratios within the specified range. In one aspect, the weight ratio of total plasticizer to enteric acid-insoluble polymer is about 11:10 (≈1.1). In another aspect, the weight ratio of total plasticizer to enteric acid-insoluble polymer is about 14:10 (≈1.4). In another aspect, the weight ratio of total plasticizer to enteric acid-insoluble polymer is about 17:10 (≈1.7). In another aspect, the weight ratio of total plasticizer to enteric acid-insoluble polymer is about 20:10 (≈2). In another aspect, the weight ratio of total plasticizer to enteric acid-insoluble polymer is about 19.3: 11.2 (≈1.73).

In one embodiment, the weight ratio range of total plasticizer to total polymer (film forming and enteric acid-insoluble polymer) is about 18:45 to about 20:40 (i.e., ≈0.40-0.5), including all ratios within the specified range. In one aspect, the weight ratio range of total plasticizer to total polymer is about 18:45 (≈0.40). In another aspect, the weight ratio range of total plasticizer to total polymer is about 19:40 (≈0.475). In another aspect, the weight ratio range of total plasticizer to total polymer is about 20:40 (≈0.5). In another aspect, the weight ratio range of total plasticizer to total polymer is about 19.3:40.4 (≈0.477).

In one embodiment, the solvent comprises about 20% to about 40% of the enteric soft capsule composition, including all integers within the specified range. In one embodiment, the solvent is water. The quantity of water in the composition varies depending on the quantities of the other ingredients. For example, the quantity of opacifier, colorant, flavoring, or other excipients can change the percentage of water present the composition. In one embodiment, the weight percentage of water is as much as suffices to bring the total weight percentage to 100% (i.e., quantum sufficiat; q.s.). In another embodiment, the water comprises about 20%, about 25%, about 30%, about 35%, or about 40% of the enteric soft capsule composition. In another embodiment, water comprises about 35% to about 40% of the enteric soft capsule composition. In one embodiment, water comprises about 37% of the composition.

In one embodiment, the final moisture (water) content of the enteric soft capsule is from about 8% to about 15%, including all integers within the specified range. In another embodiment, the moisture content is about 8% to about 12%, including all integers within the specified range. In one aspect, the final moisture content is about 8%. In one aspect, the final moisture content is about 9%. In one aspect, the final moisture content is about 10%. In one aspect, the final moisture content is about 11%. In another aspect, the final moisture content is about 12%.

In one embodiment, the enteric soft capsule shell has the exemplary composition shown in Table 4.

TABLE 4

Exemplary Enteric Soft Capsule Shell Composition

| Component | Percent weight |
|---|---|
| Gelatin | 29.2 |
| Methacrylic Acid Copolymer (EUDRAGIT ® L 100) | 11.2 |
| Glycerol | 18.0 |
| Triethyl citrate | 1.3 |
| Ammonium hydroxide | 1.7 |

TABLE 4-continued

Exemplary Enteric Soft Capsule Shell Composition

| Component | Percent weight |
|---|---|
| Titanium dioxide | 1.5 |
| Water | 37.1 |
| TOTAL | 100% |
| Final pH | 8.5-9.0 |
| Total polymer % weight (gelatin + enteric) | 40.4% |
| Gelatin % wt of total polymer (gelatin + enteric) | 72.4% |
| Enteric % wt of total polymer (gelatin + enteric) | 27.6% |
| Ratio of Enteric to Gelatin | 11.2:29.2 (0.38) |
| Total plasticizer % weight (glycerol + triethyl citrate) | 19.3% |
| Ratio of total plasticizer to total polymer | 19.3:40.4 (0.48) |
| Ratio total plasticizer to gelatin | 19.3:29.2 (0.66) |
| Ratio total plasticizer to enteric | 19.3:11.2 (1.73) |
| Water content in dried enteric soft capsule: | 8-15% |

In one embodiment, the enteric soft capsule shell comprises about 30% gelatin; about 10% poly(methyl) acrylate copolymer; about 18% glycerol; about 1% triethyl citrate; about 1.5% ammonia; about 37% water; and about 1.5% titanium dioxide.

In another embodiment, the enteric soft capsule is described in U.S. Provisional Patent Application No. 62/015,063, which is incorporated by reference herein for such teachings.

One embodiment described herein provides an enteric acid-insoluble polymer dispersed within the film-forming polymer gel mass that provides the total soft gel composition with enteric acid-insoluble properties, at relatively low concentrations of the enteric acid-insoluble polymer (e.g., from about 8% to about 20% of the total wet gel mass composition) and without the need of excessive amounts of alkali, thus avoiding denaturation or degradation of the film-forming polymer that can weaken the integrity of the enteric soft capsule shell.

Films of the enteric soft capsule shell do not dissolve or disintegrate in acids, such as 0.1 N hydrochloric acid or simulated gastric fluid (ca. pH 1.2), despite the fact that the majority of the shell ingredients (i.e., greater than 50%) normally dissolve in, or are miscible with, acids. Enteric soft capsules made using the compositions described herein remain intact in hydrochloric acid or simulated gastric fluid for at least two hours. The capsules readily release the contents upon shifting the pH of the solution to ca. 6.8, such as that of simulated intestinal fluid.

In another embodiment, the final enteric capsule composition provides films of increased strength without substantially compromising film elasticity. Moreover, films made from the enteric soft capsule compositions as described herein are sealed at normal temperature range typically used for making traditional soft gel capsules. In one aspect, enteric soft capsules are made using a rotary die apparatus as described in U.S. Pat. Nos. 5,459,983; 5,146,730; and 6,482,516, each of which are incorporated by reference herein for such teachings.

Another embodiment described herein includes a process of manufacturing enteric soft capsules comprising the pharmaceutical composition as described herein. The process includes preparing a gel mass composition comprising a film-forming, water-soluble polymer and an enteric acid-insoluble polymer and mixing with appropriate plasticizers and solvent; casting the gel mass into films or ribbons using heat-controlled drums or surfaces; and manufacturing a soft capsule comprising a matrix fill using rotary die technology. The thickness of the films or ribbons that form the enteric capsule shell is from about 0.010 inches (≈0.254 mm) to about 0.050 inches (≈1.27 mm), including all integers within the specified range. The shell thickness comprises about 0.010 inch (≈0.254 mm), about 0.015 inch (≈0.381 mm), about 0.02 in (≈0.508 mm), about 0.03 in (≈0.762 mm), about 0.04 in (≈1.02 mm), or about 0.05 in (≈1.27 mm). In one embodiment, the thickness is about 0.02 inches (≈0.508 mm) to about 0.040 inches (≈1.02 mm). In one embodiment, the shell thickness is about 0.028 inches (≈0.711 mm). In another embodiment, the shell thickness is about 0.033 inches (≈0.838 mm). In another embodiment, the shell thickness is about 0.038 inches (≈0.965 mm).

In one embodiment described herein, the enteric soft capsule shell described herein, encapsulates a matrix fill as described herein. In another embodiment described herein, the enteric soft capsule shell and encapsulated matrix fill comprises an outer dimension from about 2 oval to about 30 oval including all iterations of capsule size within the specified range (e.g., 2 oval, 3 oval, 4 oval, 5 oval, 6 oval, 7 oval, 8 oval, 10 oval, 12 oval, 16 oval, 20, or 30 oval). In another embodiment described herein, the enteric soft capsule shell and encapsulated matrix fill comprises a outer dimension from about 2 round to about 28 round including all iterations of capsule size within the specified range (e.g., 2 round, 3 round, 4 round, 5 round, 6 round, 7 round, 8 round, 10 round, 12 round, 16 round, 20 round or 28 round). In another embodiment described herein, the enteric soft capsule shell and encapsulated matrix fill comprises an outer dimension from about 2 oblong to about 22 oblong including all iterations of capsule size within the specified range (e.g., 2 oblong, 3 oblong, 4 oblong, 5 oblong, 6 oblong, 7 oblong, 8 oblong, 10 oblong, 11, oblong, 12 oblong, 14 oblong, 16 oblong, 20 oblong, or 22 oblong). Dimension specifications of soft capsules and tablets are known to those skilled in the art. See *Remington's Essentials of Pharmaceutics*, Pharmaceutical Press Publishing Company, London, UK, 1$^{st}$ Edition, 2013, which is incorporated by reference herein for such teachings.

The enteric soft capsules described herein can contain a matrix fill that is liquid, semi-solid, or solid. Capsules prepared as described herein can contain a hydrophobic solution or suspension, such as vegetable oils or shortening, or waxes, or combinations thereof. The matrix fill can be formulated to prevent interaction with the capsule shell components and release the pharmaceutical composition at a specified rate.

One embodiment described herein, is a pharmaceutical composition comprising a matrix fill formulation comprising any of the formulations shown in the Tables or Examples described herein. Any of the components of the formulations shown in the Tables or Examples can be increased, decreased, combined, recombined, switched, or removed to provide for a formulation comprising about 100% by weight.

In one embodiment, the pharmaceutical composition described herein provides a dosage of fumarate ester for administration to a subject. The dosage form can be administered, for example, to a subject, or a subject in need thereof. In one aspect, the subject is a mammal, or a mammal in need thereof. In one aspect, the subject is a human, or human in need thereof. In one aspect, the human or human in need thereof is a medical patient. In one aspect, the human subject is a child (~0-9 years old) or an adolescent (~10-17 years old). In one aspect, the subject is from 0 to 9 years of age. In another aspect, the human subject is from 10 to 17 years of age. In another aspect, the human subject is over 17 years of age. In another aspect, the human subject is an adult (≥18 years of age).

The dosage form can be administered, for example, 1×, 2×, 3×, 4×, 5×, 6×, or even more times per day. One or more dosage form can be administered, for example, for 1, 2, 3, 4, 5, 6, 7 days, or even longer. One or more dosage forms can be administered, for example, for 1, 2, 3, 4 weeks, or even longer. One or more dosage forms can be administered, for example, for 1, 2, 3, 4, 5, 6, 7, 8, 9, 10, 11, 12 months, 1 year, 2, years, 3 years, 4 years, 5 years, over 5 years, a decade, multiple decades, or even longer. One or more dosage forms can be administered at a regular interval until the subject or subject in need thereof, does not require treatment, prophylaxis, or amelioration of any disease or condition including but not limited to, general autoimmune or neurodegenerative disorders.

In one embodiment, the pharmaceutical composition described herein is administered in multiple dosages simultaneously. For example, two or more identical dosages are administered at one time. In another embodiment, two or more different dosages are administered at one time. Such dual or different simultaneous doses can be used to provide an effective amount of the pharmaceutical composition to a subject in need thereof.

In another embodiment, the pharmaceutical composition described herein may be used to treat, prevent, retard the progression of, delay the onset, ameliorate, reduce the symptoms of, or prophylaxis of general autoimmune or neurodegenerative disorders. Neurodegenerative disorders, as used herein, include multiple sclerosis (MS), which includes relapsing remitting multiple sclerosis (RRMS), secondary progressive multiple sclerosis (SPMS), primary progressive multiple sclerosis (PPMS), progressive relapsing multiple sclerosis (PPvMS), amyotrophic lateral sclerosis (ALS), psoriasis, psoriatic arthritis, Alzheimer's disease, Parkinson's disease, or any combination thereof.

In one embodiment described herein, other conditions, disorders, or diseases are controlled by administration of fumarate esters. The administration of pharmaceutical compositions comprising fumarate esters, as described herein, may be used for treating, preventing, retarding the progression of, delaying the onset, ameliorating, reducing the symptoms of, or prophylaxis of general autoimmune or neurodegenerative disorders, including but not limited to, acute dermatitis, adrenal leukodystrophy, AGE-induced genome damage, Alexander's disease, alopecia areata (totalis and universalis), Alper's disease, Alzheimer's disease, amyotrophic lateral sclerosis, angina pectoris, arthritis, asthma, autoimmune diseases, balo concentric sclerosis, Behçet's syndrome, bullous pemphigoid, Canavan disease, cardiac insufficiency including left ventricular insufficiency, central nervous system vasculitis, Charcot-Marie-Tooth disease, childhood ataxia with central nervous system hypomyelination, chronic active (lupoid) hepatitis, chronic dermatitis, chronic idiopathic peripheral neuropathy, chronic obstructive pulmonary disease, contact dermatitis, Crohn's disease and cutaneous Crohn's disease, cutaneous lupus, cutaneous sarcoidosis, diabetic retinopathy, fibromyalgia, graft versus host disease, granuloma annulare, granulomas including annulare, Grave's disease, Hashimoto's thyroiditis, hepatitis C viral infection, herpes simplex viral infection, human immunodeficiency viral infection, Huntington's disease, inflammatory bowel disease, irritable bowel disorder, ischemia, juvenile-onset diabetes mellitus, Krabbe disease, lichen planus, macular degeneration, mitochondrial encephalomyopathy, monomelic amyotrophy, multiple sclerosis (MS), myocardial infarction, necrobiosis lipoidica, neurodegeneration with brain iron accumulation, neurodermatitis, neuromyelitis optica, neuropathic pain, neurosarcoidosis, NF-κB mediated diseases, optic neuritis, organ transplantation rejection, paraneoplastic syndromes, Parkinson's disease, Pelizaeus-Merzbacher disease, pemphigus, pernicious anemia, primary lateral sclerosis, progressive supranuclear palsy, psoriasis, psoriatic arthritis, pyoderma gangrenosum, radicular pain, radiculopathic pain, reperfusion injury, retinopathic pigmentosa, rheumatoid arthritis (RA), sarcoidosis, sarcoidosis, Schilder's disease, sciatic pain, sciatica, Sjögren's syndrome, subacute necrotizing myelopathy, such as polyarthritis, Susac's syndrome, systemic lupus erythematosus (SLE), tumors, transverse myelitis, ulcerative colitis, or Zellweger syndrome.

One embodiment described herein comprises a method for orally administering a dosage form that provides a total amount of about 20 mg to about 1000 mg (e.g., ~20-1000 mg) of fumarate ester, including each integer within the specified mass range.

In one embodiment, the fumarate ester (FAE) dosage form can comprise, but is not limited to, a total amount of FAE of about 60 mg FAE, about 80 mg FAE, about 100 mg FAE, about 120 mg FAE, about 140 mg FAE, about 160 mg FAE, about 180 mg FAE, about 200 mg FAE, about 220 mg FAE, about 240 mg FAE, about 260 mg FAE, about 280 mg FAE, about 300 mg FAE, about 320 mg FAE, about 340 mg FAE, about 360 mg FAE, about 380 mg FAE, about 400 mg FAE, about 420 mg FAE, about 430 mg FAE, about 440 mg FAE, about 450 mg FAE, about 460 mg FAE, about 470 mg FAE, about 480 mg FAE, about 490 mg FAE, about 500 mg FAE, about 510 mg FAE, about 520 mg FAE, about 530 mg FAE, about 540 mg FAE, about 550 mg FAE, about 560 mg FAE, about 570 mg FAE, about 580 mg FAE, about 590 mg FAE, about 600 mg FAE, or even more.

In one embodiment, the daily dosage is about 100 mg to about 720 mg FAE including each integer within the specified range. In one aspect, the daily dosage is about 120-720 mg FAE, including each integer within the specified range. In one aspect, the daily dosage is about 120 mg FAE. In one aspect, the daily dosage is about 240 mg FAE. In another embodiment, the daily dosage is about 480 mg FAE. In another embodiment, the daily dosage is about 600 mg FAE. In another embodiment, the dosage is about 720 mg FAE.

In another embodiment, the daily dosage form can comprise, but is not limited to, a total amount of FAE of about 120 mg, about 140 mg, about 180 mg, about 200 mg, about 220 mg, about 240 mg, about 260 mg, about 280 mg, about 300 mg, about 320 mg, about 340 mg, about 360 mg, about 380 mg, about 400 mg FAE, about 420 mg FAE, about 440 mg FAE, about 460 mg FAE, about 480 mg FAE, about 500 mg FAE, about 520 mg FAE, about 540 mg FAE, about 560 mg FAE, about 580 mg FAE, about 600 mg FAE, about 620 mg FAE, about 640 mg FAE, about 660 mg FAE, about 680 mg FAE, about 700 mg FAE, about 720 mg FAE, about 740 mg FAE, about 760 mg FAE, about 780 mg FAE, about 800 mg FAE, about 820 mg FAE, or about 840 mg FAE.

The daily dosage form can contain a total amount of fumarate ester effective for treatment of retarding the progression of, prophylaxis of delaying the onset of, amelioration of, or reducing symptoms of multiple sclerosis or psoriasis or other neurodegenerative disorders.

In one embodiment, the effective amount of fumarate ester can comprise about 20 mg to about 1000 mg (e.g., 20-1000 mg) of fumarate ester, including each integer within the specified range. In one embodiment, the effective amount can comprise, but is not limited to, about 120-840 mg FAE. The effective amount can comprise, but is not limited to, a total amount of about 120 mg to about 840 mg FAE, about 120 mg to about 820 mg FAE, about 120 mg to about 720 mg FAE, about 120 mg to about 700 mg FAE, about 120 mg to about 680 mg FAE, about 120 mg to about 660 mg FAE, about 120 mg to about 640 mg FAE, about 120 mg to about 600 mg FAE, about 120 mg to about 580 mg FAE, about 120 mg to about 540 mg FAE, about 120 mg to about 520 mg FAE, about 120 mg to about 500 mg FAE, about 120 mg to about 480 mg FAE, about 120 mg to about 460 mg FAE, about 120 mg to about 440 mg FAE, about 120 mg to about 420 mg FAE, about 120 mg to about 400 mg FAE, about 120 mg to about 380 mg FAE, about 120 mg to about 360 mg FAE, about 120 mg to about 340 mg FAE, about 120 mg to about 320 mg FAE, about 120 mg to about 300 mg FAE, about 120 mg to about 280 mg FAE, about 120 mg to about 260 mg FAE, about 120 mg to about 240 mg FAE, about 120 mg to about 220 mg FAE, about 120 mg to about 200 mg FAE, about 120 mg to about 180 mg FAE, about 120 mg to about 160 mg FAE, or about 120 mg to about 140 mg FAE.

In another embodiment, the effective amount of fumarate ester can comprise, but is not limited to, about 60 mg FAE to about 840 mg FAE (e.g., 60-840 mg FAE), including each integer within the specified range. In one aspect, the effective amount can comprise, but is not limited to, an effective amount of about 60 mg to about 120 mg FAE, about 60 mg to about 140 mg FAE, about 60 mg to about 160 mg FAE, about 60 mg to about 180 mg FAE, about 60 mg to about 200 mg FAE, about 60 mg to about 220 mg FAE, about 60 mg to about 240 mg FAE; about 120 mg to about 140 mg FAE, about 120 mg to about 160 mg FAE, about 120 mg to about 180 mg FAE, about 120 mg to about 200 mg FAE, about 120 mg to about 220 mg FAE, about 120 mg to about 240 mg FAE; about 240 mg to about 260 mg FAE, about 240 mg to about 280 mg FAE, about 240 mg to about 300 mg FAE, about 240 mg to about 320 mg FAE, about 240 mg to about 340 mg FAE, about 240 mg to about 360 mg FAE, about 240 mg to about 380 mg FAE, about 240 mg to about 400 mg FAE, about 240 mg to about 420 mg FAE, about 240 mg to about 440 mg FAE, about 240 mg to about 460 mg FAE, about 240 mg to about 480 mg FAE; about 480 mg to about 500 mg FAE, about 480 mg to about 520 mg FAE, about 48 mg to about 540 mg FAE, about 480 mg to about 560 mg FAE, about 480 mg to about 580 mg FAE, about 480 mg to about 600 mg FAE, about 480 mg to about 620 mg FAE, about 480 mg to about 640 mg FAE, about 480 mg to about 660 mg FAE, about 480 mg to about 680 mg FAE, about 480 mg to about 700 mg FAE, about 480 mg to about 720 mg FAE, about 480 mg to about 740 mg FAE, about 480 mg to about 760 mg FAE, about 480 mg to about 780 mg FAE, about 480 mg to about 800 mg FAE, about 480 mg to about 820 mg FAE, or about 480 mg to about 840 mg FAE.

In one embodiment described herein, the FAE may comprise a suspension having an active pharmaceutical ingredient load (e.g., drug load) of about 1% to about 60%, including each integer within the specified range. In one embodiment, the drug load can comprise about 1%, about 2%, about 2.5%, about 5%, about 10%, about 15%, about 20%, about 25%, about 30%, about 35%, about 40%, about 45%, about 40%, about 50%, about 60%, or even higher. In one aspect, the drug load is about 20%. In one aspect, the drug load is about 30%. In one aspect, the drug load is about 40%. In one aspect, the drug load is about 50%. In one aspect, the drug load is about 60%. In one aspect, the drug load is about 28%. In one aspect, the drug load is about 32%.

In one aspect, the drug load is about 44%. In one embodiment, the drug load is about 48%. In one embodiment, the drug load is about 56%.

One embodiment described herein is a pharmaceutical composition comprising any one of the pharmaceutical compositions described herein for administration to a subject having a general autoimmune or neurodegenerative disorder, including but not limited to multiple sclerosis, comprising a therapeutically effective amount of one or more fumarate esters, wherein the administration is sufficient to achieve a reduction of about 0.224 annualized relapse rate relative to baseline in the subject without substantially inducing one or more of flushing, abdominal pain, diarrhea, and nausea in the subject; and wherein the administration does not require titration of the pharmaceutical composition.

Another embodiment described herein is a method for treating, retarding the progression of, prophylaxis of, delaying the onset of, ameliorating, or reducing the symptoms of multiple sclerosis or psoriasis comprising the administration of a therapeutically effective amount of one or more fumarate esters comprising any one of the pharmaceutical compositions described herein to a subject with multiple sclerosis, wherein the administration is sufficient to achieve a reduction of about 0.224 annualized relapse rate relative to baseline in the subject without substantially inducing one or more of flushing, abdominal pain, diarrhea, and nausea in the subject. In one aspect, after administration of ay one the pharmaceutical compositions described herein, the subject experiences one or more of flushing, abdominal pain, diarrhea, and nausea at a rate of less than about 10%. In another aspect, the endpoint may be less than about 2%, about 5%, about 10%, about 15%, about 20%, about 25%, about 30%, about 35%, about 45%, about 50%, or greater than about 50%.

Another embodiment described herein is a pharmaceutical composition and a method for treating, retarding the progression of, delaying the onset of, prophylaxis of, amelioration of, or reducing the symptoms of a general autoimmune or neurodegenerative disorder, including but not limited to multiple sclerosis or psoriasis, the method comprising the administration of a therapeutically effective amount of one or more fumarate esters comprising any one of the pharmaceutical compositions described herein to a subject in need thereof, wherein the subject achieves a reduction of annualized relapse rate relative to baseline without substantially experiencing one or more of flushing, abdominal pain, diarrhea, and nausea. In another aspect, the endpoint may be less than about 2%, about 5%, about 10%, about 15%, about 20%, about 25%, about 30%, about 35%, about 45%, about 50%, or greater than about 50%, relative to baseline.

Endpoints for treating multiple sclerosis using fumarate esters are described in the TECFIDERA® Prescribing Information (Biogen Idec Inc.), and U.S. Patent Application Publication No. US 2014/0163100, each of which is incorporated by reference herein for such teachings. Other pharmaceutical compositions and methods for treating multiple sclerosis are described in U.S. Pat. Nos. 6,509,376; 7,320,999; 7,619,001; 7,803,840; 8,399,514; 8,524,773; and 8,759,393, and International Patent Application Publication No. WO 2013/119677, each of which is incorporated by reference herein for such teachings.

Another embodiment described herein is a pharmaceutical composition for administration to a subject with multiple sclerosis or psoriasis comprising a therapeutically effective amount of one or more fumarate esters, wherein the subject achieves a reduction of annualized relapse rate relative to baseline without substantially experiencing one or more of flushing, abdominal pain, diarrhea, and nausea. In one aspect the reduction may be about 1%, about 2%, about 5%, about 10%, about 15%, about 20%, about 25%, about 30%, about 35%, about 45%, about 50%, or greater than about 50%.

For the treatment of multiple sclerosis (e.g., relapsing forms of MS such as RRMS), the dosage form administered to the subject or subject in need thereof comprises an enteric soft capsule comprising micronized solid particles of a fumarate ester as the only active ingredient or in combination with one or more NSAIDS (e.g., aspirin) or leukotriene receptor antagonists (e.g., montelukast or zafirlukast). In one aspect, the effective amount of fumarate ester (FAE) is about 480 mg per day and the subjects can receive the effective amount, i.e., 240 mg FAE bis in die (BID), in the form of two capsules a day, to be taken orally. In another aspect, the effective amount of FAE is about 480 mg FAE per day and the subjects can receive the effective amount, i.e., 480 mg FAE quaque die (QD), in the form of one capsule a day, to be taken orally. In another aspect, the effective amount of FAE is about 600 mg FAE per day and the subjects can receive the effective amount, i.e., 600 mg FAE quaque die (QD), in the form of one or more capsules a day, to be taken orally. In another aspect, the effective amount of FAE is about 720 mg FAE per day and the subjects can receive the effective amount, i.e., 720 mg FAE quaque die (QD), in the form of one or more capsules a day, to be taken orally.

For the treatment of psoriasis, the dosage form administered to the subject or subject in need thereof comprises an enteric soft capsule comprising micronized solid particles of a fumarate ester as the only active ingredient or in combination with one or more NSAIDS (e.g., aspirin) or leukotriene receptor antagonists (e.g., montelukast or zafirlukast). In one aspect, the effective amount of fumarate ester (FAE) is about 480 mg per day and the subjects can receive the effective amount, i.e., 240 mg FAE bis in die (BID), in the form of two capsules a day, to be taken orally. In another aspect, the effective amount of FAE is about 480 mg FAE per day and the subjects can receive the effective amount, i.e., 480 mg FAE quaque die (QD), in the form of one capsule a day, to be taken orally. In another aspect, the effective amount of FAE is about 600 mg FAE per day and the subjects can receive the effective amount, i.e., 600 mg FAE quaque die (QD), in the form of one or more capsules a day, to be taken orally. In another aspect, the effective amount of FAE is about 720 mg FAE per day and the subjects can receive the effective amount, i.e., 720 mg FAE quaque die (QD), in the form of one or more capsules a day, to be taken orally.

FAE can cause flushing and gastrointestinal (GI) side effects in some subjects. While the side effects generally subside soon after subjects start on the treatment, in one aspect the starting dose is 120 mg FAE BID orally for the first 7 days. The dose is increased to the effective dose of 240 mg FAE BID (i.e., about 480 mg FAE per day). In another aspect, the starting dose is 240 mg FAE BID orally for the first 7 days. The dose is increased to the effective dose of 480 mg FAE QD (i.e., about 480 mg FAE per day). For those subjects who experience GI or flushing side effects, taking FAE with food can improve tolerability. In one aspect described herein, FAE is administered after a meal. In another aspect described herein, FAE is administered after a high-fat meal to reduce or ameliorate the one or more symptoms of flushing, abdominal pain, diarrhea, and nausea in the subject.

In one embodiment, the pharmaceutical compositions described herein can be administered without titration of the pharmaceutical composition. In one aspect, the pharmaceutical compositions can be administered without titration and without substantially inducing one or more of flushing, abdominal pain, diarrhea, and nausea in the subject.

In one embodiment, the pharmaceutical composition described herein does not elicit the flushing and gastrointestinal side effects when the dose is about 240 mg FAE quaque die (QD) (i.e., 240 mg FAE per day). In one embodiment, the pharmaceutical composition described herein does not elicit the flushing and gastrointestinal side effects when the dose is about 480 mg FAE quaque die (QD) (i.e., 480 mg FAE per day). In one embodiment, the pharmaceutical composition described herein does not elicit the flushing and gastrointestinal side effects when the dose is about 600 mg FAE quaque die (QD) (i.e., 600 mg FAE per day). In one embodiment, the pharmaceutical composition described herein does not elicit the flushing and gastrointestinal side effects when the dose is about 720 mg FAE quaque die (QD) (i.e., 720 mg FAE per day).

In one embodiment, the pharmaceutical composition described herein does not elicit the flushing and gastrointestinal side effects when the effective amount is about 480 mg FAE quaque die (QD) (i.e., 480 mg FAE per day). In another embodiment, the pharmaceutical composition described herein does not elicit flushing and gastrointestinal side effects when the effective amount is about 600 mg FAE quaque die (QD) (i.e., 600 mg FAE per day). In another embodiment, the pharmaceutical composition described herein does not elicit flushing and gastrointestinal side effects when the effective amount is about 720 mg FAE quaque die (QD) (i.e., 720 mg FAE per day).

In another aspect, the administration of about 325 mg of non-enteric coated aspirin 30-minutes prior to FAE dosing can reduce the occurrence and severity of flushing. In one aspect, subjects who experience flushing with gastrointestinal side effects may reduce the dose to 120 mg FAE BID temporarily. Within a month, the effective dose of 240 mg FAE BID should be resumed. In another aspect, subjects who experience flushing with gastrointestinal side effects may reduce the dose to 240 mg FAE BID temporarily. Within a month, the effective dose of 480 mg FAE QD should be resumed.

In one embodiment, a subject administered a FAE pharmaceutical composition described herein may take one or more non-steroidal anti-inflammatory drugs (NSAID) before (for example, about 10 minutes to an hour, e.g., about 30 minutes before) taking a FAE pharmaceutical composition described herein. In one embodiment, the subject administered a dosage form takes the one or more non-steroidal anti-inflammatory drugs to reduce flushing. In one embodiment, the one or more non-steroidal anti-inflammatory drugs comprise aspirin, ibuprofen, naproxen, ketoprofen, celecoxib, or combinations thereof. The one or more non-steroidal anti-inflammatory drugs can be administered in an amount of about 50 mg to about 500 mg before taking the dosage form described herein. In one embodiment, a subject takes 325 mg aspirin about 30-minutes before taking the dosage forms described herein.

In another embodiment, a subject administered a FAE pharmaceutical composition described herein may take one or more leukotriene receptor antagonists. In another embodiment, a subject administered a FAE pharmaceutical composition described herein may take 10 to 20 mg of montelukast (Singulair®) or zafirlukast (Accolate®).

In another embodiment described herein, subjects are orally administered one or more non-steroidal anti-inflammatory drugs before taking the dosage form described herein exhibit the same pharmacokinetic properties (e.g., $C_{max}$ and AUC) as subjects orally administered the dosage form described herein without administering one or more non-steroidal anti-inflammatory drugs (e.g., aspirin, ibuprofen, naproxen, ketoprofen, celecoxib, or combinations thereof). The NSAID can be administered about 30-minutes before taking the dosage form described herein.

In one embodiment, subjects with multiple sclerosis or psoriasis are administered an enteric soft capsule containing 240 mg FAE, twice-daily for a total daily dose of 480 mg, wherein the enteric soft capsule comprises solid microparticles of FAE in a matrix. In one embodiment, the matrix is a controlled release matrix. In another embodiment, the matrix is a delayed release matrix. In another embodiment, the matrix is an extended release matrix.

In one embodiment, subjects having a general autoimmune or neurodegenerative disorder, including but not limited to multiple sclerosis or psoriasis, are administered an enteric soft capsule containing about 480 mg FAE, one daily for a total daily dose of about 480 mg, wherein the enteric soft capsule comprises solid microparticles of FAE in a matrix. In one embodiment, the matrix is a controlled release matrix. In another embodiment, the matrix is a delayed release matrix. In another embodiment, the matrix is an extended release matrix.

Pharmacokinetics of fumarate esters, particularly DMF, are described by Sheikh et al., *Clinical Therapeutics* 35(10): 1582-1594 (2013), which is incorporated by reference herein for such teachings.

In one embodiment described herein, a subject is administered a capsule containing 240 mg FAE, twice daily for a total daily dose of 480 mg. In one aspect, the pharmaceutical composition comprises an immediate release, delayed release, controlled release, or extended release formulation of a fumarate ester. In another aspect, the pharmaceutical composition comprises an enteric soft capsule. In another aspect, the composition is provided in a dosage form containing a total amount of about 240 mg of a fumarate ester, wherein subjects administered the dosage form twice-daily exhibit a mean plasma monomethyl fumarate $C_{max}$ ranging from about 0.4 mg/L to about 2.41 mg/L, including all iterations of integers within the specified range. In another aspect, the composition is provided in a dosage form containing a total amount of about 240 mg of a fumarate ester, wherein subjects administered the dosage form twice-daily exhibit a mean plasma monomethyl fumarate $C_{max}$ ranging from about 1.5 mg/L to about 3.4 mg/L, including all iterations of integers within the specified range. In another aspect, the composition is provided in a dosage form containing a total amount of about 240 mg of a fumarate ester, wherein subjects administered the dosage form twice-daily exhibit a mean plasma monomethyl fumarate $C_{max}$ ranging from about 1.03 mg/L to about 2.41 mg/L, including all iterations of integers within the specified range. In another aspect, the composition is provided in a dosage form containing a total amount of about 240 mg of a fumarate ester, wherein subjects administered the dosage form twice-daily exhibit a mean plasma monomethyl fumarate $C_{max}$ ranging from about 0.4 mg/L to about 0.75 mg/L, including all iterations of integers within the specified range. In another aspect, the composition is provided in a dosage form containing a total amount of about 240 mg of a fumarate ester, wherein subjects administered the dosage form twice-daily exhibit a mean plasma monomethyl fumarate $C_{max}$ ranging from about 0.76 mg/L to about 1.03 mg/L, including all iterations of integers within the specified range. In another aspect, the composition is provided in a dosage form containing a total amount of about 240 mg of a fumarate ester, wherein subjects administered the dosage form twice-daily exhibit a mean plasma monomethyl fumarate $C_{max}$ ranging from about 1.04 mg/L to about 1.75 mg/L, including all iterations of integers within the specified range. In another aspect, the composition is provided in a dosage form containing a total amount of about 240 mg of a fumarate ester, wherein subjects administered the dosage form twice-daily exhibit a mean plasma monomethyl fumarate $C_{max}$ ranging from about 1.75 mg/L to about 2.41 mg/L, including all iterations of integers within the specified range. In another aspect, the composition is provided in a dosage form containing a total amount of about 240 mg of a fumarate ester, wherein subjects administered the dosage form twice-daily exhibit a mean plasma monomethyl fumarate $C_{max}$ of at least 0.4 mg/L, at least 0.5 mg/L, at least 0.6 mg/L, at least 0.7 mg/L, at least 0.8 mg/L, at least 0.9 mg/L, at least 1 mg/L, at least 1.1 mg/L, at least 1.2 mg/L, at least 1.3 mg/L, at least 1.4 mg/L, at least 1.5 mg/L, at least 1.6 mg/L, at least 1.7 mg/L, at least 1.8 mg/L, at least 1.9 mg/L, at least 2 mg/L, at least 2.1 mg/L, at least 2.2 mg/L, at least 2.3 mg/L, at least 2.4 mg/L, at least 2.5 mg/L, at least 2.6 mg/L, at least 2.7 mg/L, at least 2.8 mg/L, at least 2.9 mg/L, at least 3 mg/L, at least 3.1 mg/L, at least 3.2 mg/L, at least 3.3 mg/L, or at least 3.4 mg/L.

In another aspect, the composition is provided in a dosage form containing a total amount of about 240 mg of a fumarate ester, wherein subjects administered the dosage form twice-daily exhibit a mean plasma monomethyl fumarate $AUC_{overall}$ ranging from about 2.01 h·mg/L to about 15.2 h·mg/L, including all iterations of integers within the specified range. In another aspect, the composition is provided in a dosage form containing a total amount of about 240 mg of a fumarate ester, wherein subjects administered the dosage form twice-daily exhibit a mean plasma monomethyl fumarate $AUC_{overall}$ ranging from about 2.01 h·mg/L to about 5.2 h·mg/L, including all iterations of integers within the specified range. In another aspect, the composition is provided in a dosage form containing a total amount of about 240 mg of a fumarate ester, wherein subjects administered the dosage form twice-daily exhibit a mean plasma monomethyl fumarate $AUC_{overall}$ ranging from about 11.3 h·mg/L to about 15.2 h·mg/L, including all iterations of integers within the specified range. In another aspect, the composition is provided in a dosage form containing a total amount of about 240 mg of a fumarate ester, wherein subjects administered the dosage form twice-daily exhibit a mean plasma monomethyl fumarate $AUC_{overall}$ ranging from about 5.2 h·mg/L to about 11.2 h·mg/L, including all iterations of integers within the specified range. In another aspect, the composition is provided in a dosage form containing a total amount of about 240 mg of a fumarate ester, wherein subjects administered the dosage form twice-daily exhibit a mean plasma monomethyl fumarate $AUC_{overall}$ at least about 2.0 h·mg/L, at least about 2.3 h·mg/L, at least about 2.6 h·mg/L, at least about 2.9 h·mg/L, at least 3.2 h·mg/L, at least 3.5 h·mg/L, at least 3.8 h·mg/L, at least 4.1 h·mg/L, at least 4.4 h·mg/L, at least 4.7 h·mg/L, at least 5.0 h·mg/L, at least 5.3 h·mg/L, at least 5.6 h·mg/L, at least 5.9 h·mg/L, at least 6.2 h·mg/L, at least 6.5 h·mg/L, at least 6.8 h·mg/L, at least 7.1 h·mg/L, at least 7.4 h·mg/L, at least 7.7 h·mg/L, at least 8.0 h·mg/L, at least 8.3 h·mg/L, at least 8.6 h·mg/L, at least 8.9 h·mg/L, at least 9.2 h·mg/L, at least 9.5 h·mg/L, at least 9.8 h·mg/L, at least 10.1 h·mg/L, at least 10.4 h·mg/L, at least 10.7 h·mg/L, at least 11.0 h·mg/L, at least 11.3 h·mg/L, at least 11.6 h·mg/L, at least 11.9 h·mg/L, at least 12.2 h·mg/L, at least 12.5 h·mg/L, at least 12.8 h·mg/L, at least 13.1 h·mg/L, at least 13.3 h·mg/L, at least 13.6 h·mg/L, at least 13.9 h·mg/L, at least 14.2 h·mg/L, at least 14.5 h·mg/L, at least 14.8 h·mg/L, or at least 15.2 h·mg/L.

In another aspect, the composition is provided in a dosage form containing a total amount of about 240 mg of a fumarate ester, wherein subjects administered the dosage form exhibit a mean plasma monomethyl fumarate $AUC_{0 \to 12h}$ ranging from about 1.5 h·mg/L to about 5.6 h·mg/L, including all iterations of integers within the specified range. In another aspect, the composition is provided in a dosage form containing a total amount of about 240 mg of a fumarate ester, wherein subjects administered the dosage form exhibit a mean plasma monomethyl fumarate $AUC_{0 \to 12h}$ ranging from about 1.5 h·mg/L to about 2.5 h·mg/L, including all iterations of integers within the specified range. In another aspect, the composition is provided in a dosage form containing a total amount of about 240 mg of a fumarate ester, wherein subjects administered the dosage form exhibit a mean plasma monomethyl fumarate $AUC_{0 \to 12h}$ ranging from about 2.6 h·mg/L to about 5.5 h·mg/L, including all iterations of integers within the specified range. In another aspect, the composition is provided in a dosage form containing a total amount of about 240 mg of a fumarate ester, wherein subjects administered the dosage form exhibit a mean plasma monomethyl fumarate $AUC_{0 \to 12h}$ of at least 2 h·mg/L, of at least 2.1 h·mg/L, at least 2.2 h·mg/L, at least 2.3 h·mg/L, at least 2.4 h·mg/L, at least 2.5 h·mg/L, at least 2.6 h·mg/L, at least 2.7 h·mg/L, at least 2.8 h·mg/L, at least 2.9 h·mg/L, at least 3 h·mg/L, at least 3.1 h·mg/L, at least 3.2 h·mg/L, at least 3.3 h·mg/L, at least 3.4 h·mg/L, at least 3.5 h·mg/L, at least 3.6 h·mg/L, at least 3.7 h·mg/L, at least 3.8 h·mg/L, at least 3.9 h·mg/L, at least 4 h·mg/L, at least 4.1 h·mg/L, at least 4.2 h·mg/L, at least 4.3 h·mg/L, at least 4.4 h·mg/L, at least 4.5 h·mg/L, at least 4.6 h·mg/L, at least 4.7 h·mg/L, at least 4.8 h·mg/L, at least 4.9 h·mg/L, at least 5 h·mg/L, at least 5.1 h·mg/L, at least 5.2 h·mg/L, at least 5.3 h·mg/L, at least 5.4 h·mg/L, or at least 5.5 h·mg/L.

In another aspect, the composition is provided in a dosage form containing a total amount of about 240 mg of a fumarate ester, wherein subjects administered the dosage form exhibit a mean plasma monomethyl fumarate $AUC_{0 \to \infty}$ ranging from about 1.5 h·mg/L to about 5.6 h·mg/L, including all iterations of integers within the specified range. In another aspect, the composition is provided in a dosage form containing a total amount of about 240 mg of a fumarate ester, wherein subjects administered the dosage form exhibit a mean plasma monomethyl fumarate $AUC_{0 \to \infty}$ ranging from about 1.5 h·mg/L to about 2.5 h·mg/L, including all iterations of integers within the specified range. In another aspect, the composition is provided in a dosage form containing a total amount of about 240 mg of a fumarate ester, wherein subjects administered the dosage form exhibit a mean plasma monomethyl fumarate $AUC_{0 \to \infty}$ ranging from about 2.6 h·mg/L to about 5.5 h·mg/L, including all iterations of integers within the specified range. In another aspect, the composition is provided in a dosage form containing a total amount of about 240 mg of a fumarate ester, wherein subjects administered the dosage form exhibit a mean plasma monomethyl fumarate $AUC_{0 \to \infty}$ of at least 2 h·mg/L, of at least 2.1 h·mg/L, at least 2.2 h·mg/L, at least 2.3 h·mg/L, at least 2.4 h·mg/L, at least 2.5 h·mg/L, at least 2.6 h·mg/L, at least 2.7 h·mg/L, at least 2.8 h·mg/L, at least 2.9 h·mg/L, at least 3 h·mg/L, at least 3.1 h·mg/L, at least 3.2 h·mg/L, at least 3.3 h·mg/L, at least 3.4 h·mg/L, at least 3.5 h·mg/L, at least 3.6 h·mg/L, at least 3.7 h·mg/L, at least 3.8 h·mg/L, at least 3.9 h·mg/L, at least 4 h·mg/L, at least 4.1 h·mg/L, at least 4.2 h·mg/L, at least 4.3 h·mg/L, at least 4.4 h·mg/L, at least 4.5 h·mg/L, at least 4.6 h·mg/L, at least 4.7 h·mg/L, at least 4.8 h·mg/L, at least 4.9 h·mg/L, at least 5 h·mg/L, at least 5.1 h·mg/L, at least 5.2 h·mg/L, at least 5.3 h·mg/L, at least 5.4 h·mg/L, or at least 5.5 h·mg/L.

In another aspect, the composition is provided in a dosage form containing a total amount of about 240 mg of a fumarate ester, wherein subjects administered the dosage form exhibit a mean plasma monomethyl fumarate $T_{max}$ ranging from about 1.5 hours to about 8.5 hours including all iterations of integers within the specified range. In another aspect, the composition is provided in a dosage form containing a total amount of about 240 mg of a fumarate ester, wherein subjects administered the dosage form exhibit a mean plasma monomethyl fumarate $T_{max}$ ranging from about 1.6 hours to about 2.5 hours, including all iterations of integers within the specified range. In another aspect, the composition is provided in a dosage form containing a total amount of about 240 mg of a fumarate ester, wherein subjects administered the dosage form exhibit a mean plasma monomethyl fumarate $T_{max}$ ranging from about 2.6 hours to about 5 hours, including all iterations of integers within the specified range. In another aspect, the composition is provided in a dosage form containing a total amount of about 240 mg of a fumarate ester, wherein subjects administered the dosage form exhibit a mean plasma monomethyl fumarate $T_{max}$ ranging from about 5.1 hours to about 7.5 hours, including all iterations of integers within the specified range. In another aspect, the composition is provided in a dosage form containing a total amount of about 240 mg of a fumarate ester, wherein subjects administered the dosage form exhibit a mean plasma monomethyl fumarate $T_{max}$ ranging from about 7.6 hours to about 8.5 hours, including all iterations of integers within the specified range. In another aspect, the composition is provided in a dosage form containing a total amount of about 240 mg of a fumarate ester, wherein subjects administered the dosage form exhibit a mean plasma monomethyl fumarate $T_{max}$ of at least 1.6 hours, at least 1.8 hours, at least 2 hours, at least 2.2 hours, at least 2.4 hours, at least 2.6 hours, at least 2.8 hours, at least 3 hours, at least 3.2 hours, at least 3.4 hours, at least 3.6 hours, at least 3.8 hours, at least 4 hours, at least 4.2 hours, at least 4.4 hours, at least 4.6 hours, at least 4.8 hours, at least 5 hours, at least 5.2 hours, at least 5.4 hours, at least 5.6 hours, at least 5.8 hours, at least 6 hours, at least 6.2 hours, at least 6.4 hours, at least 6.6 hours, at least 6.8 hours, at least 7 hours, at least 7.2 hours, at least 7.4 hours, at least 7.6 hours, at least 7.8 hours, at least 8 hours, at least 8.2 hours, or at least 8.4 hours.

In one embodiment described herein, a subject is administered a capsule containing 480 mg FAE, once daily for a total daily dose of 480 mg. In one aspect, the pharmaceutical composition comprises an immediate release, delayed release, controlled release, or extended release formulation of a fumarate ester. In another aspect, the pharmaceutical composition comprises an enteric soft capsule. In another aspect, the composition is provided in a dosage form containing a total amount of about 480 mg of a fumarate ester, wherein subjects administered the dosage form once daily exhibit a mean plasma monomethyl fumarate $C_{max}$ ranging from about 0.4 mg/L to about 5.2 mg/L, including all iterations of integers within the specified range. In another aspect, the composition is provided in a dosage form containing a total amount of about 480 mg of a fumarate ester, wherein subjects administered the dosage form once daily exhibit a mean plasma monomethyl fumarate $C_{max}$ ranging from about 1.5 mg/L to about 5.2 mg/L, including all iterations of integers within the specified range. In another aspect, the composition is provided in a dosage form containing a total amount of about 480 mg of a fumarate ester, wherein subjects administered the dosage form once daily exhibit a mean plasma monomethyl fumarate $C_{max}$ ranging from about 0.4 mg/L to about 0.75 mg/L, including all iterations of integers within the specified range. In another aspect, the composition is provided in a dosage form containing a total amount of about 480 mg of a fumarate ester, wherein subjects administered the dosage form once daily exhibit a mean plasma monomethyl fumarate $C_{max}$ ranging from about 0.76 mg/L to about 1.03 mg/L, including all iterations of integers within the specified range. In another aspect, the composition is provided in a dosage form containing a total amount of about 480 mg of a fumarate ester, wherein subjects administered the dosage form once daily exhibit a mean plasma monomethyl fumarate $C_{max}$ ranging from about 1.04 mg/L to about 1.75 mg/L, including all iterations of integers within the specified range. In another aspect, the composition is provided in a dosage form containing a total amount of about 480 mg of a fumarate ester, wherein subjects administered the dosage form once daily exhibit a mean plasma monomethyl fumarate $C_{max}$ ranging from about 1.75 mg/L to about 2.41 mg/L, including all iterations of integers within the specified range. In another aspect, the composition is provided in a dosage form containing a total amount of about 480 mg of a fumarate ester, wherein subjects administered the dosage form once daily exhibit a mean plasma monomethyl fumarate $C_{max}$ ranging from about 2.42 mg/L to about 3.5 mg/L, including all iterations of integers within the specified range. In another aspect, the composition is provided in a dosage form containing a total amount of about 480 mg of a fumarate ester, wherein subjects administered the dosage form once daily exhibit a mean plasma monomethyl fumarate $C_{max}$ ranging from about 3.6 mg/L to about 5.2 mg/L, including all iterations of integers within the specified range. In another aspect, the composition is provided in a dosage form containing a total amount of about 480 mg of a fumarate ester, wherein subjects administered the dosage form once daily exhibit a mean plasma monomethyl fumarate $C_{max}$ of at least 1.6 mg/L, at least 1.7 mg/L, at least 1.8 mg/L, at least 1.9 mg/L, at least 2.0 mg/L, at least 2.1 mg/L, at least 2.2 mg/L, at least 2.3 mg/L, at least 2.4 mg/L, at least 2.5 mg/L, at least 2.6 mg/L, at least 2.7 mg/L, at least 2.8 mg/L, at least 2.9 mg/L, at least 3.0 mg/L, at least 3.1 mg/L, at least 3.2 mg/L, at least 3.3 mg/L, at least 3.4 mg/L, at least 3.5 mg/L, at least 3.6 mg/L, at least 3.7 mg/L, at least 3.8 mg/L, at least 3.9 mg/L, at least 4.0 mg/L, at least 4.1 mg/L, at least 4.2 mg/L, at least 4.3 mg/L, at least 4.4 mg/L, at least 4.5 mg/L, at least 4.6 mg/L, at least 4.7 mg/L, at least 4.8 mg/L, at least 4.9 mg/L, at least 5.0 mg/L, or at least 5.1 mg/L In another aspect, the composition is provided in a dosage form containing a total amount of about 480 mg of a fumarate ester, wherein subjects administered the dosage form once daily exhibit a mean plasma monomethyl fumarate $AUC_{0 \to 12h}$ ranging from about 1.5 h·mg/L to about 15.5 h·mg/L, including all iterations of integers within the specified range. In another aspect, the composition is provided in a dosage form containing a total amount of about 480 mg of a fumarate ester, wherein subjects administered the dosage form once daily exhibit a mean plasma monomethyl fumarate $AUC_{0 \to 12h}$ ranging from about 1.5 h·mg/L to about 2.5 h·mg/L, including all iterations of integers within the specified range. In another aspect, the composition is provided in a dosage form containing a total amount of about 480 mg of a fumarate ester, wherein subjects administered the dosage form once daily exhibit a mean plasma monomethyl fumarate $AUC_{0\to 12h}$ ranging from about 2.6 h·mg/L to about 5.5 h·mg/L, including all iterations of integers within the specified range. In another aspect, the composition is provided in a dosage form containing a total amount of about 480 mg of a fumarate ester, wherein subjects administered the dosage form once daily exhibit a mean plasma monomethyl fumarate $AUC_{0\to 12h}$ ranging from about 5.6 h·mg/L to about 7.5 h·mg/L, including all iterations of integers within the specified range. In another aspect, the composition is provided in a dosage form containing a total amount of about 480 mg of a fumarate ester, wherein subjects administered the dosage form once daily exhibit a mean plasma monomethyl fumarate $AUC_{0\to 12h}$ ranging from about 7.6 h·mg/L to about 10.5 h·mg/L, including all iterations of integers within the specified range. In another aspect, the composition is provided in a dosage form containing a total amount of about 480 mg of a fumarate ester, wherein subjects administered the dosage form once daily exhibit a mean plasma monomethyl fumarate $AUC_{0\to 12h}$ ranging from about 10.5 h·mg/L to about 15.5 h·mg/L, including all iterations of integers within the specified range. In another aspect, the composition is provided in a dosage form containing a total amount of about 480 mg of a fumarate ester, wherein subjects administered the dosage form once daily exhibit a mean plasma monomethyl fumarate $AUC_{0\to 12h}$ of at least 2.0 h·mg/L, at least 2.3 h·mg/L, at least 2.6 h·mg/L, at least 2.9 h·mg/L, at least 3.2 h·mg/L, at least 3.5 h·mg/L, at least 3.8 h·mg/L, at least 4.1 h·mg/L, at least 4.4 h·mg/L, at least 4.7 h·mg/L, at least 5 h·mg/L, at least 5.3 h·mg/L, at least 5.6 h·mg/L, at least 5.9 h·mg/L, at least 6.2 h·mg/L, at least 6.5 h·mg/L, at least 6.8 h·mg/L, at least 7.1 h·mg/L, at least 7.4 h·mg/L, at least 7.7 h·mg/L, at least 8.0 h·mg/L, at least 8.3 h·mg/L, at least 8.6 h·mg/L, at least 8.9 h·mg/L, at least 9.2 h·mg/L, at least 9.5 h·mg/L, at least 9.8 h·mg/L, at least 10.1 h·mg/L, at least 10.4 h·mg/L, at least 10.7 h·mg/L, at least 11.0 h·mg/L, at least 11.3 h·mg/L, at least 11.6 h·mg/L, at least 11.9 h·mg/L, at least 12.2 h·mg/L, at least 12.5 h·mg/L, at least 12.8 h·mg/L, at least 13.1 h·mg/L, at least 13.4 h·mg/L, at least 13.7 h·mg/L, at least 14 h·mg/L, at least 14.3 h·mg/L, at least 14.6 h·mg/L, at least 14.9 h·mg/L, at least 15.2 h·mg/L, or at least 15.5 h·mg/L.

In another aspect, the composition is provided in a dosage form containing a total amount of about 480 mg of a fumarate ester, wherein subjects administered the dosage form once daily exhibit a mean plasma monomethyl fumarate $AUC_{0\to\infty}$ ranging from about 1.5 h·mg/L to about 15.5 h·mg/L, including all iterations of integers within the specified range. In another aspect, the composition is provided in a dosage form containing a total amount of about 480 mg of a fumarate ester, wherein subjects administered the dosage form once daily exhibit a mean plasma monomethyl fumarate $AUC_{0\to\infty}$ ranging from about 1.5 h·mg/L to about 2.5 h·mg/L, including all iterations of integers within the specified range. In another aspect, the composition is provided in a dosage form containing a total amount of about 480 mg of a fumarate ester, wherein subjects administered the dosage form once daily exhibit a mean plasma monomethyl fumarate $AUC_{0\to\infty}$ ranging from about 2.6 h·mg/L to about 5.5 h·mg/L, including all iterations of integers within the specified range. In another aspect, the composition is provided in a dosage form containing a total amount of about 480 mg of a fumarate ester, wherein subjects administered the dosage form once daily exhibit a mean plasma monomethyl fumarate $AUC_{0\to\infty}$ ranging from about 5.6 h·mg/L to about 7.5 h·mg/L, including all iterations of integers within the specified range. In another aspect, the composition is provided in a dosage form containing a total amount of about 480 mg of a fumarate ester, wherein subjects administered the dosage form once daily exhibit a mean plasma monomethyl fumarate $AUC_{0\to\infty}$ ranging from about 7.6 h·mg/L to about 11.5 h·mg/L, including all iterations of integers within the specified range. In another aspect, the composition is provided in a dosage form containing a total amount of about 480 mg of a fumarate ester, wherein subjects administered the dosage form once daily exhibit a mean plasma monomethyl fumarate $AUC_{0\to\infty}$ ranging from about 10.5 h·mg/L to about 15.5 h·mg/L, including all iterations of integers within the specified range. In another aspect, the composition is provided in a dosage form containing a total amount of about 480 mg of a fumarate ester, wherein subjects administered the dosage form once daily exhibit a mean plasma monomethyl fumarate $AUC_{0\to\infty}$ of at least 2.0 h·mg/L, at least 2.3 h·mg/L, at least 2.6 h·mg/L, at least 2.9 h·mg/L, at least 3.2 h·mg/L, at least 3.5 h·mg/L, at least 3.8 h·mg/L, at least 4.1 h·mg/L, at least 4.4 h·mg/L, at least 4.7 h·mg/L, at least 5 h·mg/L, at least 5.3 h·mg/L, at least 5.6 h·mg/L, at least 5.9 h·mg/L, at least 6.2 h·mg/L, at least 6.5 h·mg/L, at least 6.8 h·mg/L, at least 7.1 h·mg/L, at least 7.4 h·mg/L, at least 7.7 h·mg/L, at least 8.0 h·mg/L, at least 8.3 h·mg/L, at least 8.6 h·mg/L, at least 8.9 h·mg/L, at least 9.2 h·mg/L, at least 9.5 h·mg/L, at least 9.8 h·mg/L, at least 10.1 h·mg/L, at least 10.4 h·mg/L, at least 10.7 h·mg/L, at least 11.0 h·mg/L, at least 11.3 h·mg/L, at least 11.6 h·mg/L, at least 11.9 h·mg/L, at least 12.2 h·mg/L, at least 12.5 h·mg/L, at least 12.8 h·mg/L, at least 13.1 h·mg/L, at least 13.4 h·mg/L, at least 13.7 h·mg/L, at least 14 h·mg/L, at least 14.3 h·mg/L, at least 14.6 h·mg/L, at least 14.9 h·mg/L, at least 15.2 h·mg/L, or at least 15.5 h·mg/L.

In another aspect, the composition is provided in a dosage form containing a total amount of about 480 mg of a fumarate ester, wherein subjects administered the dosage form once daily exhibit a mean plasma monomethyl fumarate $T_{max}$ ranging from about 1.5 hours to about 10.5 hours including all iterations of integers within the specified range. In another aspect, the composition is provided in a dosage form containing a total amount of about 480 mg of a fumarate ester, wherein subjects administered the dosage form once daily exhibit a mean plasma monomethyl fumarate $T_{max}$ ranging from about 1.6 hours to about 2.5 hours, including all iterations of integers within the specified range. In another aspect, the composition is provided in a dosage form containing a total amount of about 480 mg of a fumarate ester, wherein subjects administered the dosage form once daily exhibit a mean plasma monomethyl fumarate $T_{max}$ ranging from about 2.6 hours to about 5 hours, including all iterations of integers within the specified range. In another aspect, the composition is provided in a dosage form containing a total amount of about 480 mg of a fumarate ester, wherein subjects administered the dosage form once daily exhibit a mean plasma monomethyl fumarate $T_{max}$ ranging from about 5.1 hours to about 7.5 hours, including all iterations of integers within the specified range. In another aspect, the composition is provided in a dosage form containing a total amount of about 480 mg of a fumarate ester, wherein subjects administered the dosage form once daily exhibit a mean plasma monomethyl fumarate $T_{max}$ ranging from about 7.6 hours to about 8.5 hours, including all iterations of integers within the specified range. In another aspect, the composition is provided in a dosage form containing a total amount of about 480 mg of a fumarate ester, wherein subjects administered the dosage form once daily exhibit a mean plasma monomethyl fumarate $T_{max}$ ranging from about 8.6 hours to about 10.6 hours, including all iterations of integers within the specified range. In another aspect, the composition is provided in a dosage form containing a total amount of about 480 mg of a fumarate ester, wherein subjects administered the dosage form once daily exhibit a mean plasma monomethyl fumarate $T_{max}$ of at least 1.6 hours, at least 1.8 hours, at least 2 hours, at least 2.2 hours, at least 2.4 hours, at least 2.6 hours, at least 2.8 hours, at least 3 hours, at least 3.2 hours, at least 3.4 hours, at least 3.6 hours, at least 3.8 hours, at least 4 hours, at least 4.2 hours, at least 4.4 hours, at least 4.6 hours, at least 4.8 hours, at least 5 hours, at least 5.2 hours, at least 5.4 hours, at least 5.6 hours, at least 5.8 hours, at least 6 hours, at least 6.2 hours, at least 6.4 hours, at least 6.6 hours, at least 6.8 hours, at least 7 hours, at least 7.2 hours, at least 7.4 hours, at least 7.6 hours, at least 7.8 hours, at least 8 hours, at least 8.2 hours, at least 8.4 hours, at least 8.6 hours, at least 8.8 hours, at least 9.0 hours, at least 9.2 hours, at least 9.4 hours, at least 9.6 hours, at least 9.8 hours, at least 10 hours, at least 10.2 hours, at least 10.4 hours, or at least 10.6 hours.

Another embodiment described herein is a pharmaceutical composition for treating, prophylaxis, or amelioration of general autoimmune or neurodegenerative disorders, comprising a fumarate ester, wherein the composition exhibits an in vitro dissolution rate (% dissolution per minute) at pH 6.8, as described herein in any one of Drawings 2-12.

Another embodiment described herein is a pharmaceutical composition for treating, prophylaxis, or amelioration of general autoimmune or neurodegenerative disorders, including but not limited to multiple sclerosis or psoriasis, comprising a fumarate ester, wherein the composition exhibits an in vitro dissolution rate comprising about 10% to about 80% dissolution after about 5 minutes to about 480 minutes at pH 6.8, including each integer within the specified rages of dissolution and time. In another aspect, the in vitro dissolution rate at pH 6.8 is about 50% after about 20 minutes to about 1080 minutes, including each integer with in the specified time range. In one aspect, the in vitro dissolution rate at pH 6.8 is about 50% after about 5 min, is about 50% after about 10 min, about 50% after about 20 min, about 50% after about 30 min, about 50% after about 40 min, about 50% after about 50 min, about 50% after about 60 min, about 50% after about 70 min, about 50% after about 80 min, about 50% after about 90 min, about 50% after about 120 min, about 50% after about 150 min, about 50% after about 180 min, about 50% after about 210 min, about 50% after about 240 min, about 50% after about 300 min, is about 50% after about 330 min, about 50% after about 360 min, is about 50% after about 390 min, about 50% after about 420 min, about 50% after about 480 min, about 50% after about 540 min, about 50% after about 600 min, about 50% after about 660 min, about 50% after about 720 min, about 50% after about 780 min, about 50% after about 840 min, about 50% after about 900 min, about 50% after about 960 min, or about 50% after 1080 min. In another aspect, the in vitro dissolution rate at pH 6.8 is about 50% after about 0.5 hour, about 50% after about 1 hour, about 50% after about 2 hours, about 50% after about 3 hours, about 50% after about 4 hours, about 50% after about 5 hours, about 50% after about 6 hours, about 50% after about 7 hours, about 50% after about 8 hours, about 50% after about 9 hours, about 50% after about 10 hours, about 50% after about 11 hours, about 50% after about 12 hours, about 50% after about 13 hours, about 50% after about 14 hours, about 50% after about 15 hours, about 50% after about 16 hours, about 50% after about 17 hours, or about 50% after about 18 hours. In one aspect, the in vitro dissolution rate at pH 6.8 is about 50% after about 10 minutes. In another aspect, the in vitro dissolution rate at pH 6.8 is about 50% after about 20 minutes. In another aspect, the in vitro dissolution rate at pH 6.8 is about 50% after about 45 minutes. In another aspect, the in vitro dissolution rate at pH 6.8 is about 50% after about 60 minutes. In one aspect, the in vitro dissolution rate at pH 6.8 is about 50% after about 120 minutes. In another aspect, the in vitro dissolution rate at pH 6.8 is about 50% after about 180 minutes. In another aspect, the in vitro dissolution rate at pH 6.8 is about 50% after about 240 minutes. In one aspect, the in vitro dissolution rate at pH 6.8 is about 50% after about 480 minutes.

It will be readily apparent to one of ordinary skill in the relevant arts that suitable modifications and adaptations to the compositions, methods, and applications described herein can be made without departing from the scope of any embodiments or aspects thereof. The compositions and methods provided are exemplary and are not intended to limit the scope of any of the specified embodiments. All of the various embodiments, aspects, and options disclosed herein can be combined in any and all variations or iterations. The scope of the compositions, formulations, methods, and processes described herein include all actual or potential combinations of embodiments, aspects, options, examples, and preferences herein described. The ratios of the mass of any component of any of the formulations disclosed herein to the mass of any other component in the formulation or to the total mass of the other components in the formulation are hereby disclosed as if they were expressly disclosed. All patents and publications cited herein are incorporated by reference herein for the specific teachings thereof.

EXAMPLES

Example 1

DMF Enteric Soft Capsule Fills

Based on results of dimethyl fumarate (DMF) solubility testing in various lipid or lipophilic vehicles (data not shown), two formulations were selected for further studies and encapsulated in enteric soft gelatin capsules: one having polyethylene glycol and one with medium chain mono- and diglycerides. Organic acids such as caprylic acid, lactic acid, or oleic acid, were incorporated into the matrix fill to prevent the hydrolysis of dimethyl fumarate and to retain enteric properties of the shell. Application batches of enteric soft capsules were prepared by rotary die encapsulation using the fill compositions shown in Table 5.

TABLE 5

DMF Fill Compositions

| Ingredient | Capmul ® MCM Matrix (A413-A) | | PEG Matrix (A413-B) | |
| --- | --- | --- | --- | --- |
| | mg/capsule | % wt | mg/capsule | % wt |
| Dimethyl Fumarate (PSD: 80 µm) | 240 | 32.0 | 240 | 32.0 |
| Capmul ® MCM | 367.5 | 49.0 | — | — |
| PEG 400 | — | — | 382.5 | 51.0 |
| Povidone K30 | 52.5 | 7.0 | 37.5 | 5.0 |
| Tween ® 80 | 75 | 10.0 | 75 | 10.0 |
| Lactic acid | 15 | 2.0 | 15 | 2.0 |
| TOTAL | 750 | 100% | 750 | 100% |

Figure 2:
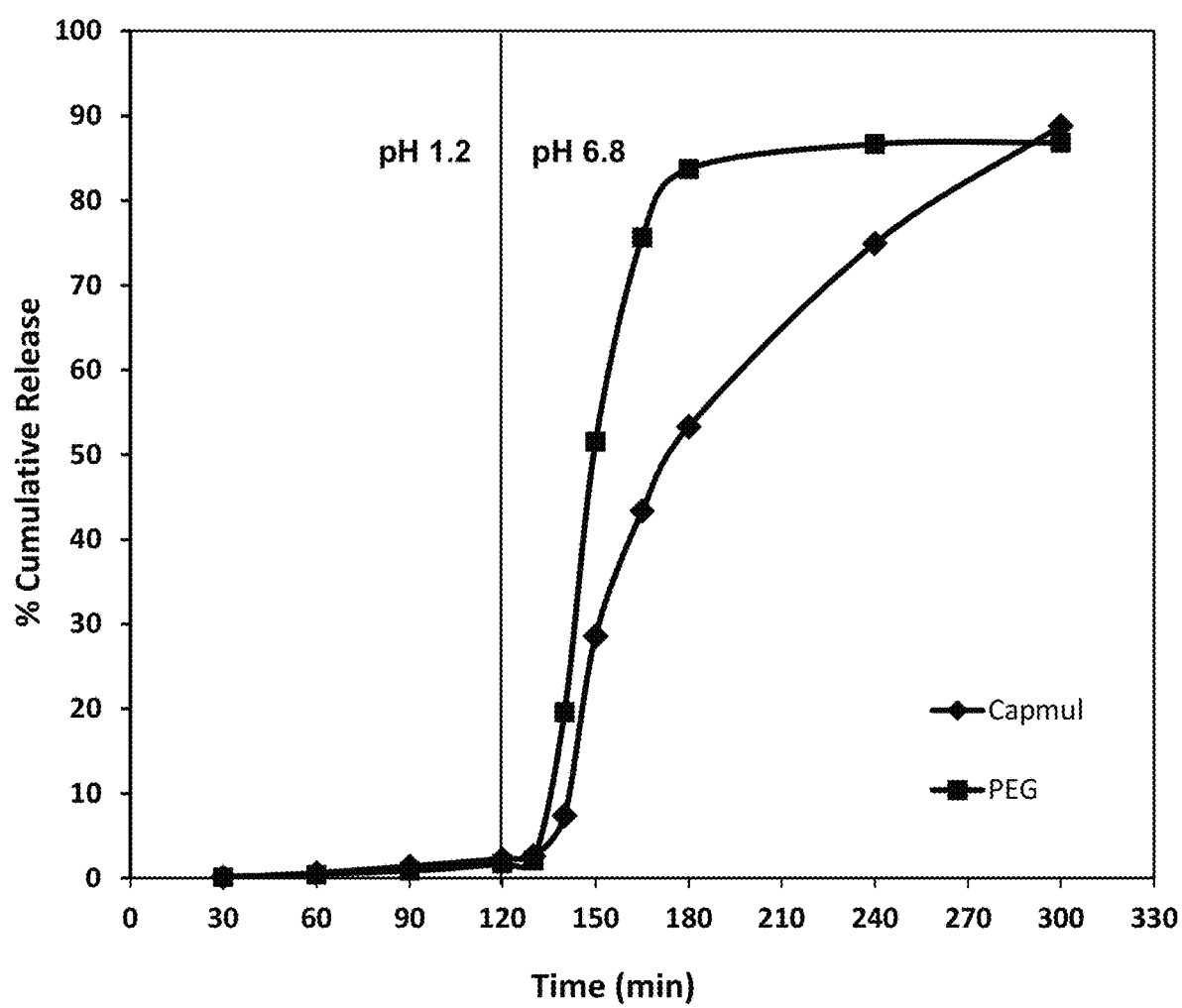
FIG. 2. Dissolution of enteric soft capsules comprising two DMF formulations.

The enteric soft capsules comprising the matrix formulations shown in Table 5 were subject to two-stage dissolution experiments in a USP Apparatus II (e.g., paddle method at 100 rpm). For these experiments, the capsule in introduced in to simulated gastric fluid, 0.1 N HCl, pH 1.2, for 2 hours. After 2 hours, the capsule is transferred to simulated intestinal fluid, phosphate buffer, pH 6.8. The results are shown in FIG. 2. The results show that the capsules retain their enteric properties for at least 2 hours in simulated gastric fluid at pH 1.2. Both types of capsules released DMF shortly after being transferred to simulated intestinal fluid, pH 6.8. The enteric soft capsules comprising matrices comprising PEG 400 released DMF more rapidly than those comprising Capmul® MCM (ABITEC Corp.; medium chain mono- and di-glycerides).

Example 2

Stability of the Enteric Soft Capsules over Time

Figure 3:
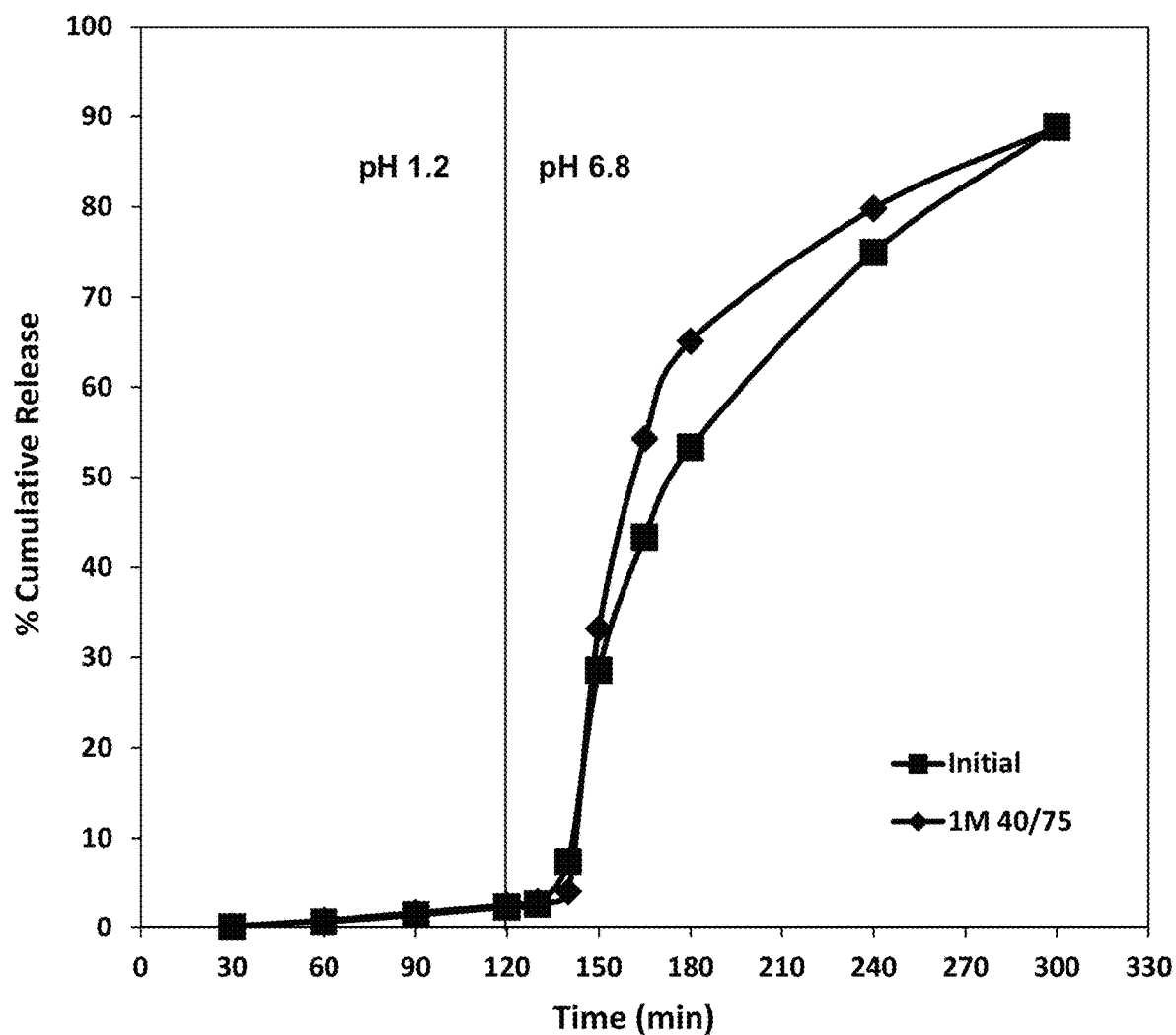
FIG. 3. DMF enteric soft capsule stability.

The temporal stability of the dimethyl fumarate enteric soft capsule fill formulation shown in Table 6 was assessed. A sample of DMF enteric soft capsules was subjected to accelerated aging by a 1 month of exposure to 40° C. and 75% relative humidity conditions and then evaluated in two-stage dissolution experiment. A second sample of DMF enteric soft capsules was subject to two-stage dissolution shortly after manufacturing. Both sets of enteric capsules remained intact in the acidic conditions for at least 2 hours. FIG. 3. The freshly manufactured capsules released DMF slightly faster than the age-accelerated capsules when the pH was shifted to 6.8 (phosphate buffer).

TABLE 6

DMF Fill Composition

| Ingredient | mg/capsule | % weight |
|---|---|---|
| Dimethyl fumarate (PSD: 80 μm) | 240 | 32.0 |
| Capmul ® MCM | 367.5 | 49.0 |
| Povidone K 30 | 52.5 | 7.0 |
| Tween ® 80 | 75 | 10.0 |
| Lactic acid | 15 | 2.0 |
| TOTAL | 750 mg | 100% |

Example 3

DMF Release in Enteric Soft Capsules

Figure 4:
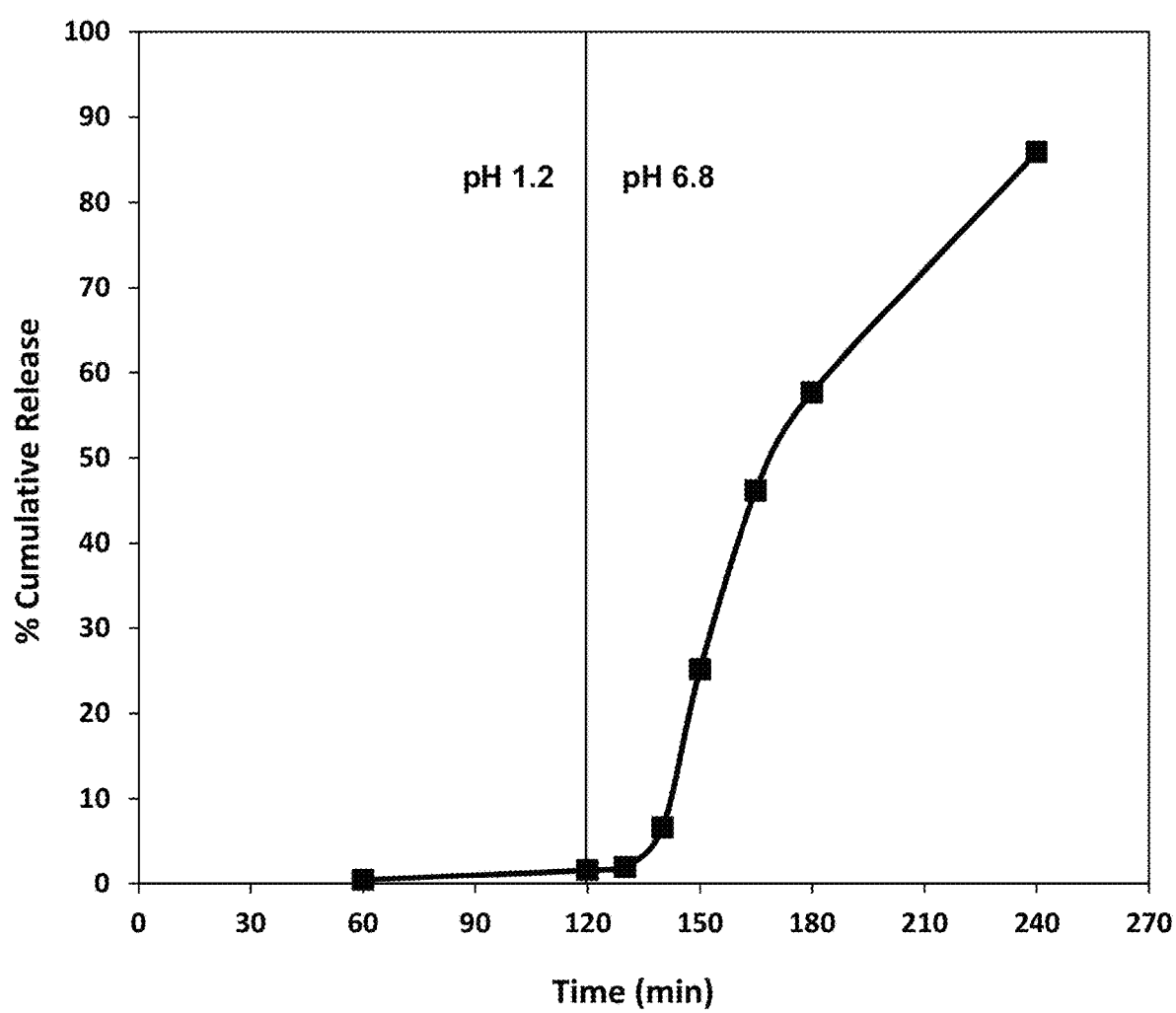
FIG. 4. DMF release in enteric soft capsules.

A developmental batch of enteric soft capsules comprising a Capmul® MCM matrix containing particles of dimethyl fumarate (Table 6) was subject to two-stage dissolution at pH 1.2 in simulated gastric fluid for 2 hours, then the buffer was changed to phosphate buffer, pH 6.8, containing 2% Cremophor® RH 40. FIG. 4. The enteric capsules remained intact in the acidic condition, and then began releasing DMF within 20 minutes of the pH-shift to simulated intestinal fluid.

Example 4

Surfactants Affect DMF Release Rate

Figure 5:
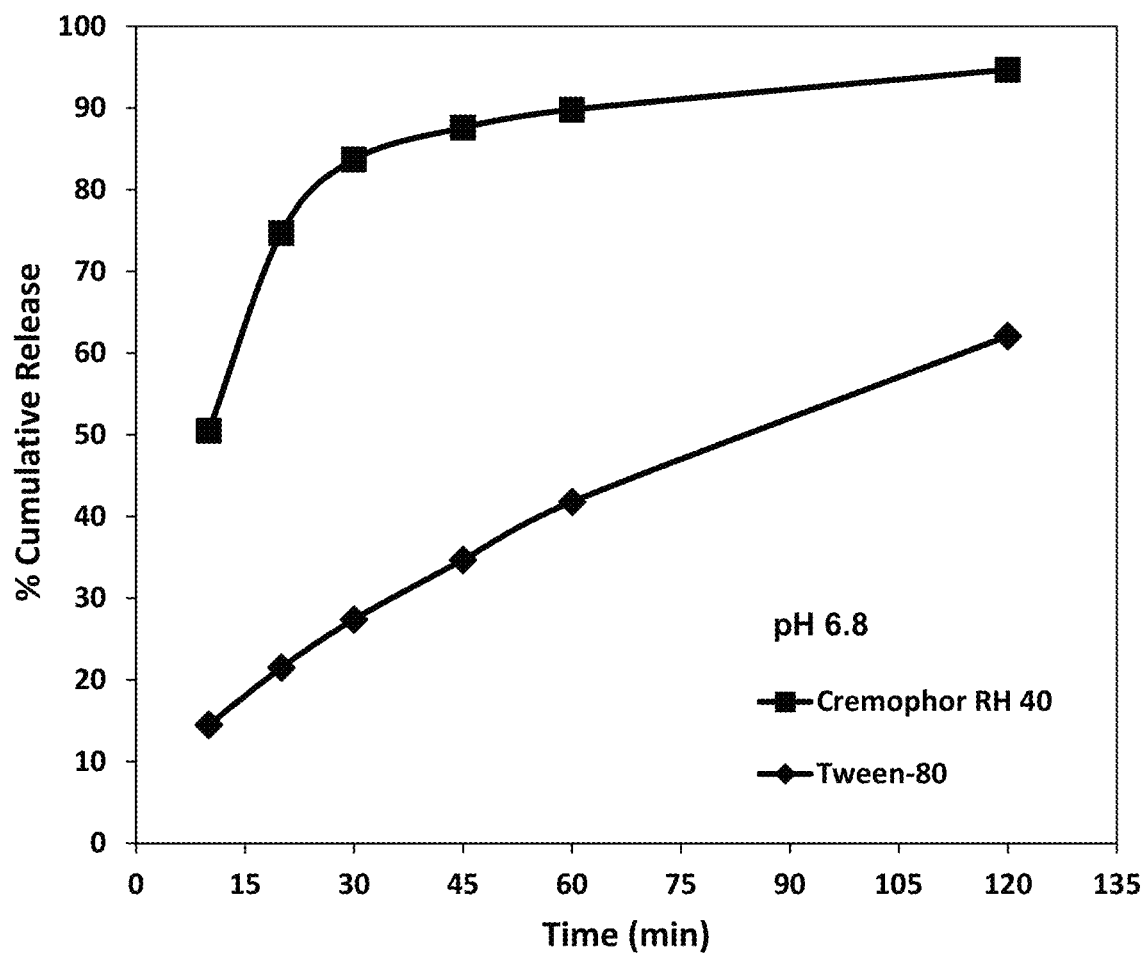
FIG. 5. Surfactants affect DMF release rate.

Enteric soft capsules were prepared with matrices comprising 10% Tween® 80 (Uniqema, ICI Americas Inc; polyoxyethylene (80) sorbitan monooleate; e.g., polysorbate 80) or 10% Cremophor® RH 40 (BASF SE; polyoxyl 40 hydrogenated castor oil) (Table 7) and then tested in dissolution experiments at pH 6.8. FIG. 5. The enteric soft capsules with fills containing Cremophor® released DMF much more rapidly than those containing Tween® 80.

TABLE 7

DMF Fill Compositions

| | Tween ® 80 Matrix | | Cremophor ® RH 40 Matrix | |
|---|---|---|---|---|
| Ingredient | mg/capsule | % wt | mg/capsule | % wt |
| Dimethyl Fumarate (PSD: 80 μm) | 240 | 32.0 | 240 | 32.0 |
| Capmul ® MCM | 367.5 | 49.0 | 367.5 | 49.0 |
| Povidone K 30 | 52.5 | 7.0 | 52.5 | 7.0 |
| Tween ® 80 | 75 | 10.0 | — | — |
| Cremophor ® RH 40 | — | — | 75 | 10.0 |
| Lactic acid | 15 | 2.0 | 15 | 2.0 |
| TOTAL | 750 | 100% | 750 | 100% |

Example 5

Polyvinylpyrrolidone Concentration Affects DMF Release Rate

Figure 6:
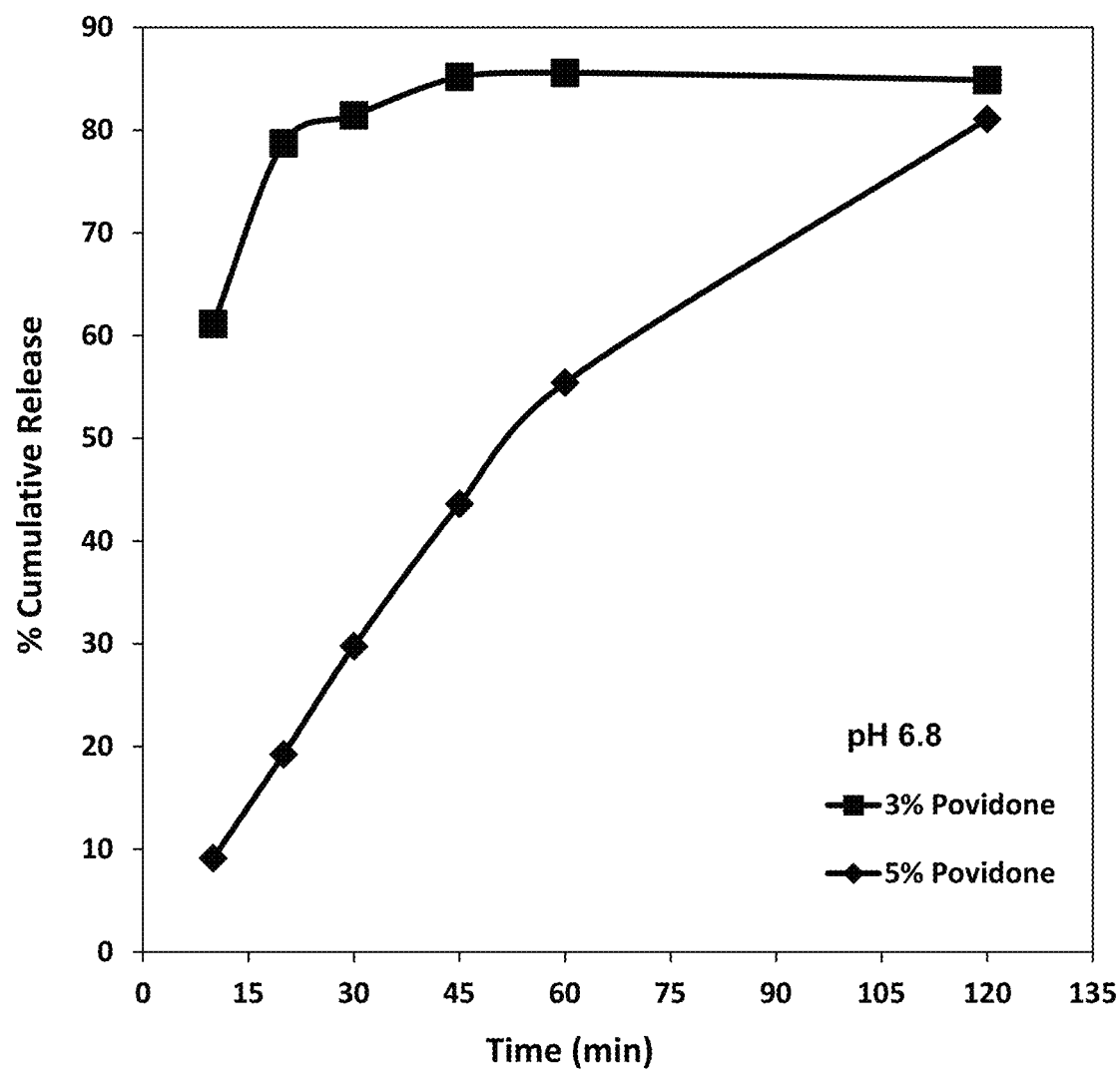
FIG. 6. Polyvinylpyrrolidone concentration affects DMF release rate.

Enteric soft capsules prepared containing fills with of 3% or 5% concentrations of Povidone K30 (e.g., PVP; 30,000 MW) (Table 8) were tested in dissolution experiments at pH 6.8. FIG. 6. The enteric soft capsules with matrices containing 5% Povidone K30 released DMF more rapidly at pH 6.8 than those with fills containing 3% Povidone K30.

TABLE 8

DMF Fill Compositions

| | 3% PVP | | 5% PVP | |
|---|---|---|---|---|
| Ingredient | mg/capsule | % wt | mg/capsule | % wt |
| Dimethyl Fumarate (PSD: 80 μm) | 240 | 32.0 | 240 | 32.0 |
| Capmul ® MCM | 397.5 | 53 | 382.5 | 51 |
| Cremophor ® RH 40 | 75 | 10.0 | 75 | 10.0 |
| Povidone K 30 | 22.5 | 3.0 | 37.5 | 5.0 |
| Lactic acid | 15 | 2.0 | 15 | 2.0 |
| TOTAL | 750 | 100% | 750 | 100% |
| Viscosity: | 43191 Cp | | 122000 Cp | |

Based on the foregoing formulation studies, the Capmul® MCM-based formulation was selected for further analysis. A batch was manufactured using the formulation below (Table 9).

TABLE 9

DMF Fill Composition

| Ingredient | mg/capsule | % weight |
|---|---|---|
| Dimethyl Fumarate (PSD: 80 μm) | 240 | 32 |
| Capmul ® MCM | 375 | 50 |
| Cremophor ® RH 40 | 75 | 10 |
| Povidone K 30 | 52.5 | 7 |
| Lactic acid | 15 | 2 |
| TOTAL | 750 mg | 100% |

Example 6

DMF Enteric Soft Capsules Are Amenable to Controlled or Extended Release

Figure 7:
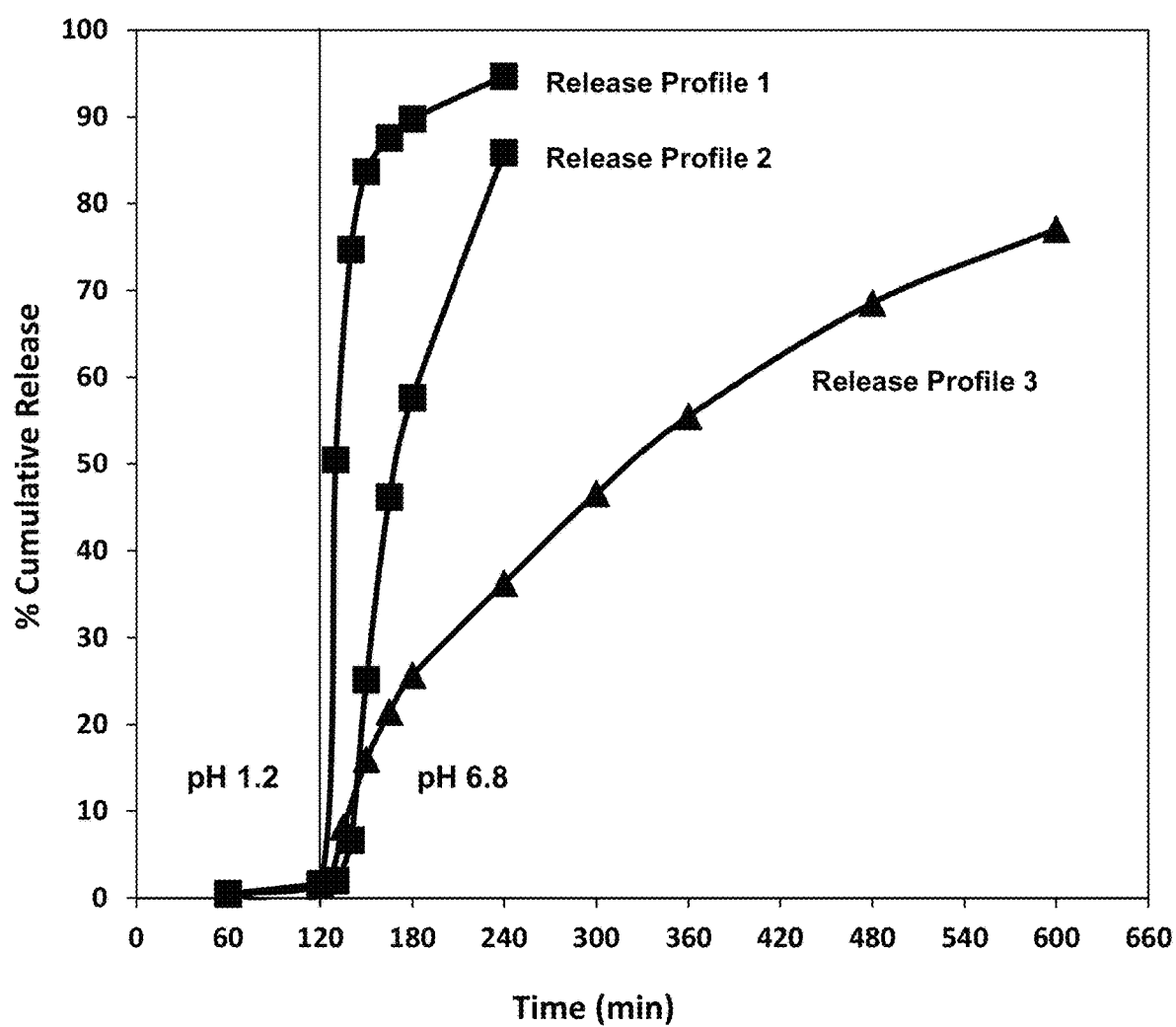
FIG. 7. DMF enteric soft capsules are amenable to controlled or extended release.

The release profile of DMF is modified by varying the enteric soft capsule shell composition or by altering the fill composition or particle size of the active ingredient. Three different release profiles were observed under two-stage dissolution experiments. All enteric soft capsules were resistant to acid for at least 2 hours, and begin releasing DMF upon transition to pH 6.8. FIG. 7. A release profile was observed in an enteric soft capsule comprising a matrix of Capmul® MCM and Cremophor® RH 40 (Table 10; Release Profile 1). A different release profile was observed with an enteric soft capsule shell comprising a Capmul® MCM and Tween® 80 matrix (Table 6; Release Profile 2). Another release profile was observed with an enteric soft capsule shell comprising a matrix of soybean oil, Tween® 80, and solid particles of DMF having an average particle distribution size of 148 μm (Table 11; Release Profile 3).

TABLE 10

| MF Fill Composition (P31) | | |
| --- | --- | --- |
| Ingredient | mg/capsule | % weight |
| Dimethyl fumarate (PSD: 80 μm) | 240 | 32.0 |
| Capmul ® MCM | 367.5 | 49.0 |
| Cremophor ® RH 40 | 75 | 10.0 |
| Povidone K 30 | 52.5 | 7.0 |
| Lactic acid | 15 | 2.0 |
| TOTAL | 750 mg | 100% |

TABLE 11

| DMF Fill Composition (P6) | | |
| --- | --- | --- |
| Ingredient | mg/capsule | % weight |
| Dimethyl fumarate (PSD 148 μm) | 240 | 43.6 |
| Soybean oil | 285.25 | 51.9 |
| Aerosil 200 | 75 | 10.0 |
| Tween ® 80 | 11 | 2.0 |
| Caprylic acid | 11 | 2.0 |
| TOTAL | 550 mg | 100% |

Example 7

DMF Particle Size Affects Release Rate

Figure 8:
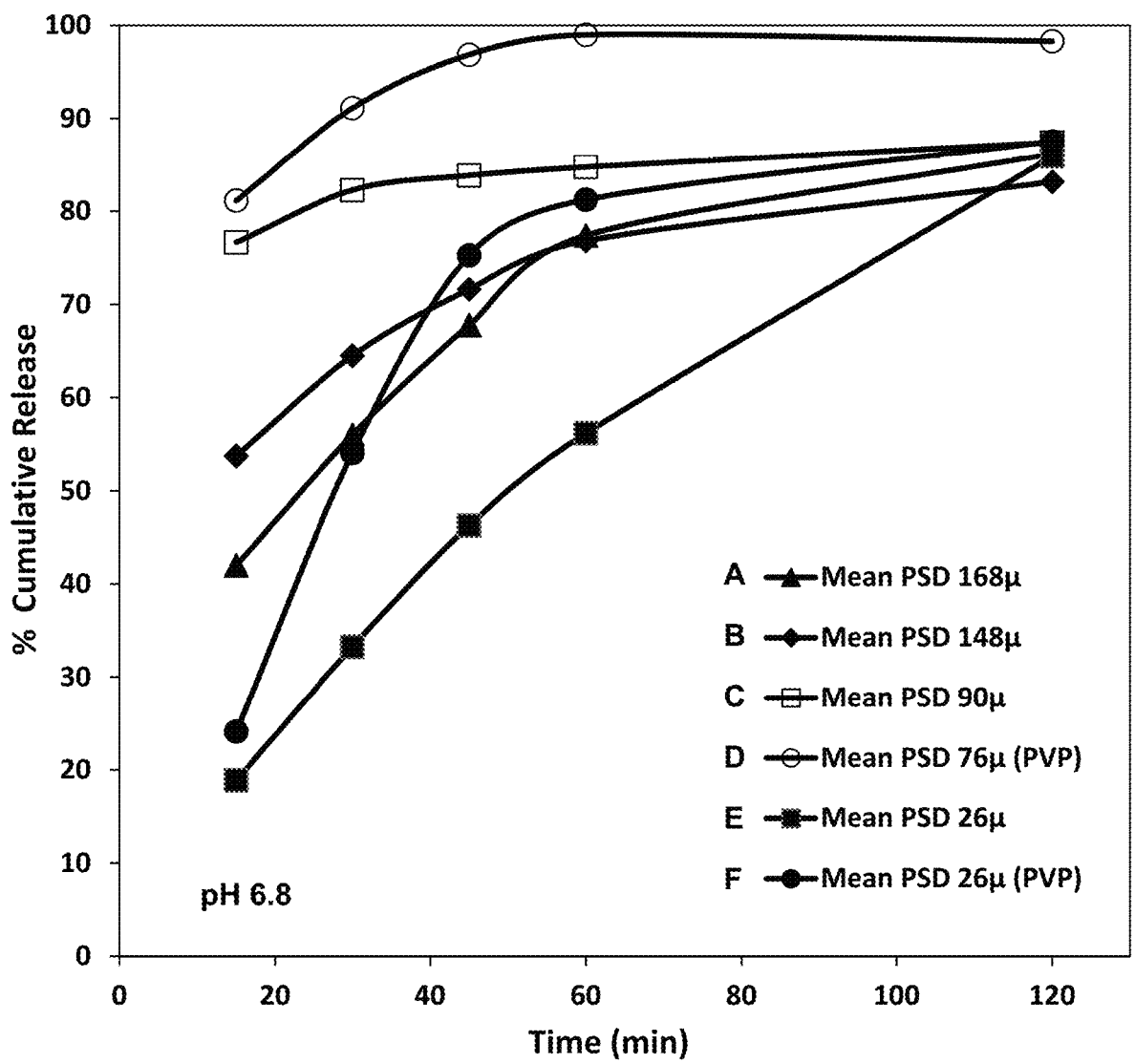
FIG. 8. DMF particle size affects release rate.

Enteric soft capsules comprising matrices with DMF particles of differing sizes were subject to dissolution at pH 6.8. FIG. 8.

TABLE 12

| Matrices with Varying DMF Particle Sizes | | | | | | |
| --- | --- | --- | --- | --- | --- | --- |
| | Formulation | | | | | |
| | A (P7) | | B (P8) | | C (P9) | |
| Ingredient | mg/capsule | % weight | mg/capsule | % weight | mg/capsule | % weight |
| DMF PSD: 168 μm | 240 | 43.6 | — | — | — | — |
| DMF PSD: 148 μm | — | — | 240 | 43.6 | — | — |
| DMF PSD: 90 μm | — | — | — | — | 240 | 43.6 |
| PEG 400 | 244 | 44.4 | 244 | 44.4 | 244 | 44.4 |
| Povidone K30 | — | — | — | — | — | — |
| Tween ® 80 | 55 | 10 | 55 | 10 | 55 | 10 |
| Caprylic acid | 11 | 2 | 11 | 2 | 11 | 2 |
| Lactic acid | — | — | — | — | — | — |
| TOTAL | 550 | 100 | 550 | 100 | 550 | 100 |
| | Formulation | | | | | |
| | D (P25) | | E (P15) | | F (P23) | |
| Ingredient | mg/capsule | % weight | mg/capsule | % weight | mg/capsule | % weight |
| DMF PSD: 76 μm | 240 | 34.3 | — | — | — | — |
| DMF PSD: 26 μm | — | — | 240 | 28.2 | 240 | 28.2 |
| PEG 400 | 355 | 50.7 | 508 | 59.8 | 482 | 56.8 |
| Povidone K30 | 21 | 3 | — | — | 26 | 3 |
| Tween ® 80 | 70 | 10 | 85 | 10 | 85 | 10 |
| Caprylic acid | — | — | 17 | 2 | 17 | 2 |
| Lactic acid | 14 | 2 | — | — | — | — |
| TOTAL | 700 | 100 | 850 | 100 | 850 | 100 |

Example 8

Enteric soft capsules comprising various matrices comprising DMF particles having particle size distribution of d90≤90 μm were prepared and analyzed in two stage (pH 1.2 and pH 6.8) or single stage (pH 6.8) dissolution experiments (data not shown). (Tables 13-15).

TABLE 13

Various DMF Fill Compositions

| | Formulation | | | | | |
|---|---|---|---|---|---|---|
| | A (P32) | | B (P33) | | C (P34) | |
| Ingredient | mg/capsule | % weight | mg/capsule | % weight | mg/capsule | % weight |
| DMF PSD: d90 ≤ 90 μm | 240 | 32.0 | 240 | 32.0 | 240 | 32.0 |
| Capmul ® MCM | 360 | 48.0 | 322.5 | 43.0 | 352.5 | 47.0 |
| Cremophor ® RH 40 | 112.5 | 15.0 | 150 | 20.0 | 112.5 | 15.0 |
| Lactic acid | 37.5 | 5.0 | 37.5 | 5.0 | 37.5 | 5.0 |
| TOTAL | 750 | 100 | 750 | 100 | 750 | 100 |

| | D (P35) | | E (P37) | | F (P38) | |
|---|---|---|---|---|---|---|
| Ingredient | mg/capsule | % weight | mg/capsule | % weight | mg/capsule | % weight |
| DMF PSD: d90 ≤ 90 μm | 240 | 32.0 | 240 | 32.0 | 240 | 32.0 |
| Capmul ® MCM | 315 | 42.0 | 360 | 48.0 | 360 | 48.0 |
| Cremophor ® RH 40 | 150 | 20.0 | 75 | 10.0 | 75 | 10.0 |
| Lactic acid | 37.5 | 5.0 | 37.5 | 5.0 | 37.5 | 5.0 |
| Povidone K 30 | 7.5 | 1.0 | — | — | — | — |
| PEG 400 | — | — | 37.5 | 5.0 | — | — |
| Polypropylene glycol | — | — | — | — | 37.5 | 5.0 |
| TOTAL | 750 | 100 | 750 | 100 | 750 | 100 |

| | G (P39) | | H (P41) | | I (P43) | |
|---|---|---|---|---|---|---|
| Ingredient | mg/capsule | % weight | mg/capsule | % weight | mg/capsule | % weight |
| DMF PSD: d90 ≤ 90 μm | 240 | 28.2 | 240 | 28.2 | 240 | 28.2 |
| Capmul ® MCM | 482.5 | 56.8 | 397.5 | 46.8 | 397.5 | 46.8 |
| Cremophor ® RH 40 | 85 | 10.0 | 85 | 10.0 | — | — |
| Lactic acid | 42.5 | 5.0 | 42.5 | 5.0 | 42.5 | 5.0 |
| Labrasol ® | — | — | 85 | 10.0 | 170 | 20.0 |
| TOTAL | 850 | 100 | 850 | 100 | 850 | 100 |

TABLE 14

Various DMF Fill Compositions

| | Formulation | | | | | |
|---|---|---|---|---|---|---|
| | A (P44) | | B (P45) | | C (P46) | |
| Ingredient | mg/capsule | % weight | mg/capsule | % weight | mg/capsule | % weight |
| DMF PSD: d90 ≤ 90 μm | 240 | 28.2 | 240 | 28.2 | 240 | 28.2 |
| Capmul ® MCM | 372 | 43.8 | 355 | 41.8 | 329.5 | 38.8 |
| Cremophor ® RH 40 | 85 | 10.0 | 85 | 10.0 | 85 | 10.0 |
| Lactic acid | 42.5 | 5.0 | 42.5 | 5.0 | 42.5 | 5.0 |
| Labrasol ® | 85 | 10.0 | 85 | 10.0 | 85 | 10.0 |
| Povidone K 30 | 25.5 | 3.0 | — | — | 25.5 | 3.0 |
| Mannitol | — | — | 42.5 | 5.0 | 42.5 | 5.0 |
| TOTAL | 850 | 100 | 850 | 100 | 850 | 100 |

TABLE 14-continued

Various DMF Fill Compositions

| | Formulation | | | | | |
|---|---|---|---|---|---|---|
| | D (P47) | | E (P48) | | F (P49) | |
| Ingredient | mg/capsule | % weight | mg/capsule | % weight | mg/capsule | % weight |
| DMF PSD: d90 ≤ 90 μm | 240 | 28.2 | 240 | 28.2 | 240 | 28.2 |
| Capmul ® MCM | 384.75 | 45.3 | 284.195 | 33.43 | 312.5 | 36.76 |
| Cremophor ® RH 40 | 85 | 10.0 | 85 | 10.0 | 85 | 10.0 |
| Lactic acid | 42.5 | 5.0 | 42.5 | 5.0 | 42.5 | 5.0 |
| Povidone K 30 | 12.75 | 1.5 | — | — | — | — |
| Labrasol ® | — | — | 85 | 10.0 | 85 | 10.0 |
| PEG 3350 | 85 | 10.0 | 113.305 | 13.33 | 85 | 10.00 |
| TOTAL | 850 | 100 | 850 | 100 | 850 | 100 |

| | G (P50) | | H (P51) | | I (P52) | |
|---|---|---|---|---|---|---|
| Ingredient | mg/capsule | % weight | mg/capsule | % weight | mg/capsule | % weight |
| DMF PSD: d90 ≤ 90 μm | 240 | 28.2 | 240 | 28.2 | 240 | 28.2 |
| Capmul ® MCM | 333.75 | 39.26 | 287 | 33.76 | 333.75 | 39.26 |
| Cremophor ® RH 40 | 85 | 10.0 | 85 | 10.00 | 85 | 10.00 |
| Lactic acid | 42.5 | 5.0 | 42.5 | 5.0 | 42.5 | 5.0 |
| Labrasol ® | 85 | 10.0 | 85 | 10.0 | 85 | 10.00 |
| PEG 3350 | 63.75 | 7.50 | — | — | — | — |
| Povidone K 17 | — | — | 25.5 | 3.00 | — | — |
| Mannitol | — | — | 85 | 10.00 | — | — |
| Crospovidone-CL | — | — | — | — | 63.75 | 7.50 |
| TOTAL | 850 | 100 | 850 | 100 | 850 | 100 |

TABLE 15

Various DMF Fill Compositions

| | Formulation | | | | | |
|---|---|---|---|---|---|---|
| | A (P53) | | B (P54) | | C (P55) | |
| Ingredient | mg/capsule | % weight | mg/capsule | % weight | mg/capsule | % weight |
| DMF PSD: d90 ≤ 90 μm | 240 | 28.24 | 240 | 28.24 | 240 | 28.24 |
| Capmul ® MCM | 397.5 | 46.76 | 397.5 | 46.76 | 390.7 | 45.96 |
| Cremophor ® RH 40 | 85 | 10.00 | 85 | 10.00 | 85 | 10.00 |
| Lactic acid | 42.5 | 5.00 | 42.5 | 5.00 | 42.5 | 5.00 |
| PEG 3350 | 85 | 10.00 | — | — | — | — |
| PEG 400 | — | — | — | — | 42.5 | 5.00 |
| Lutrol ® F 68 | — | — | 85 | 10.00 | — | — |
| Sodium lauryl sulfate | — | — | — | — | 49.3 | 5.80 |
| TOTAL | 850 | 100 | 850 | 100 | 850 | 100 |

| | D (P56) | | E (P57) | | F (P58) | |
|---|---|---|---|---|---|---|
| Ingredient | mg/capsule | % weight | mg/capsule | % weight | mg/capsule | % weight |
| DMF PSD: d90 ≤ 90 μm | 240 | 28.24 | 240 | 28.24 | 240 | 28.24 |
| Capmul ® MCM | 355 | 41.76 | 363.5 | 42.76 | 355 | 41.76 |
| Cremophor ® RH 40 | 85 | 10.00 | 85 | 10.00 | 85 | 10.00 |
| Lactic acid | 42.5 | 5.00 | 42.5 | 5.00 | 42.5 | 5.00 |
| PEG 400 | 85 | 10.00 | 85 | 10.00 | 85 | 10.00 |
| Crospovidone CL | 42.5 | 5.00 | — | — | — | — |
| Crospovidone CL-F | — | — | 34 | 4.00 | — | — |
| Crospovidone CL-M | — | — | — | — | 42.5 | 5.00 |
| TOTAL | 850 | 100 | 850 | 100 | 850 | 100 |

TABLE 15-continued

Various DMF Fill Compositions

| | Formulation | | | | | |
|---|---|---|---|---|---|---|
| | G (P59) | | H (P60) | | I (P61) | |
| Ingredient | mg/capsule | % weight | mg/capsule | % weight | mg/capsule | % weight |
| DMF PSD: d90 ≤ 90 μm | 240 | 28.24 | 240 | 28.24 | 240 | 28.24 |
| Capmul ® MCM | 312.5 | 36.76 | 355 | 41.76 | 329.5 | 38.76 |
| Cremophor ® RH 40 | 85 | 10.00 | 85 | 10.00 | 85 | 10.00 |
| Lactic acid | 42.5 | 5.00 | 42.5 | 5.00 | 42.5 | 5.00 |
| Labrasol ® | 85 | 10.00 | 85 | 10.00 | 85 | 10.00 |
| Pearlitol ® Flash | 85 | 10.00 | — | — | 42.5 | 5.00 |
| Croscarmellose Sodium | — | — | 42.5 | 5.00 | 25.5 | 3.00 |
| TOTAL | 850 | 100 | 850 | 100 | 850 | 100 |

Example 9

Capsule Shell Thickness Affects Release Rate

Figure 9:
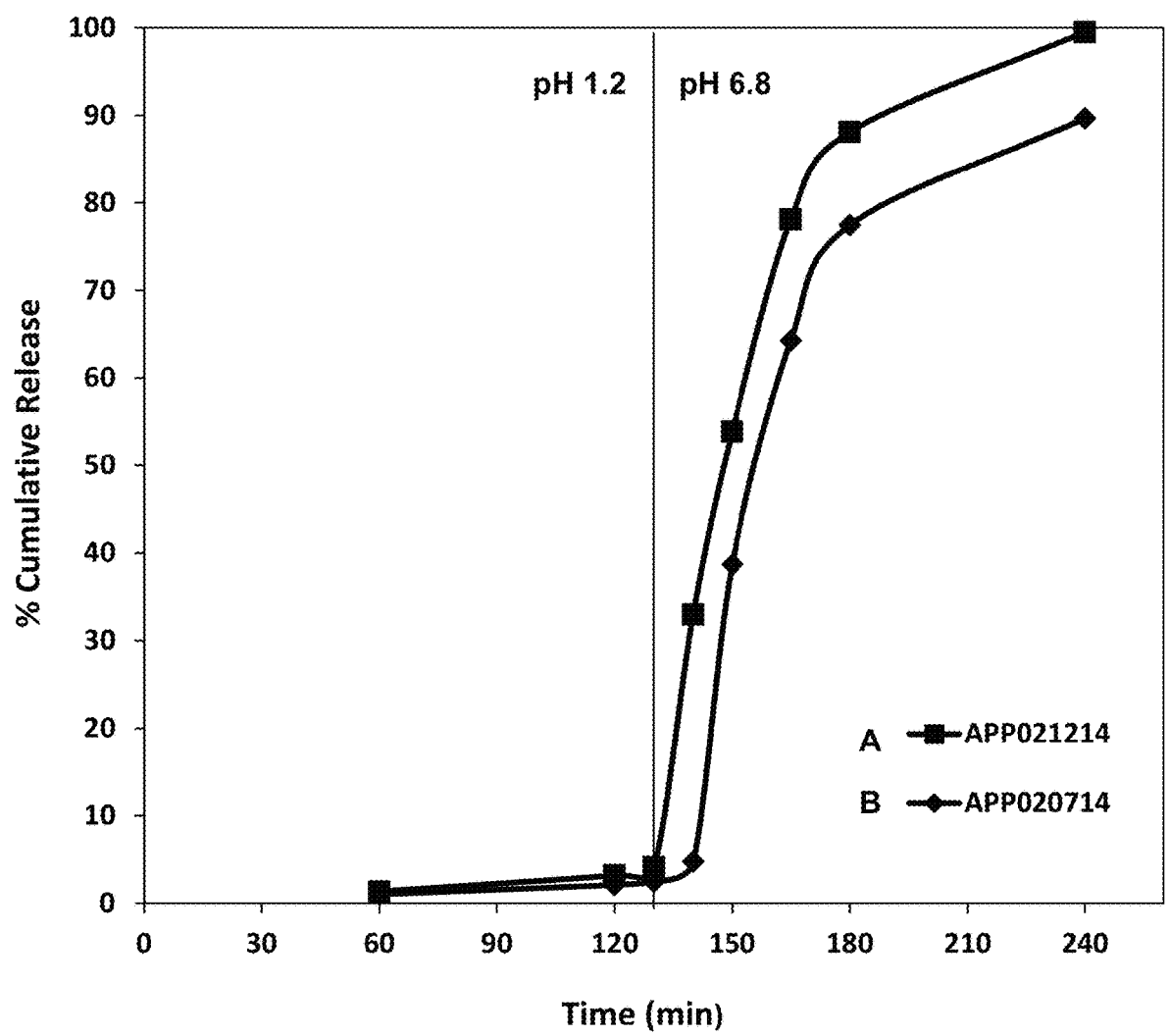
FIG. 9. Two-stage dissolution of application batches.

Application batches of enteric soft capsules with shell thicknesses of 0.028 inches or 0.033 inches were prepared comprising DMF particles having particle size distribution of d90≤90 μm in various matrices (Table 16) and analyzed in two stage (pH 1.2 and pH 6.8) dissolution experiments (FIG. 9).

TABLE 16

DMF Fill Compositions

| | A (APP021214) (0.028 inch ribbon) | | B (APP020714) (0.033 inch ribbon) | |
|---|---|---|---|---|
| Ingredient | mg/capsule | % wt | mg/capsule | % wt |
| Dimethyl Fumarate PSD: d90 ≤90 μm | 240 | 28.2 | 240 | 28.2 |
| Capmul ® MCM | 440 | 51.8 | 465.5 | 54.8 |
| Cremophor ® RH 40 | 85 | 10.0 | 85 | 10.0 |
| Povidone K30 | 42.5 | 5.0 | 42.5 | 5.0 |
| PEG 400 | — | — | 42.5 | 5.0 |
| Crospovidone-CL | 17 | 2.0 | — | — |
| TOTAL | 850 | 100% | 850 | 100% |

| | C (APP022414-A) (0.028 inch ribbon) | | D (APP022414-B) (0.028 inch ribbon) | |
|---|---|---|---|---|
| Ingredient | mg/capsule | % wt | mg/capsule | % wt |
| Dimethyl Fumarate PSD: d90 ≤90 μm | 240 | 28.24 | 240 | 28.24 |
| Capmul ® MCM | 312.5 | 36.76 | 312.5 | 36.76 |
| Cremophor ® RH 40 | 85 | 10.0 | 85 | 10.0 |
| Povidone K30 | 42.5 | 5.0 | 42.5 | 5.0 |
| PEG 600 | 127.5 | 15.0 | — | — |
| Crospovidone-CL | 42.5 | 5.0 | — | — |
| Labrasol ® | — | — | 85 | 10.0 |
| Pearlitol ® Flash | — | — | 85 | 10.0 |
| TOTAL | 850 | 100% | 850 | 100% |

Example 10

Figure 10:
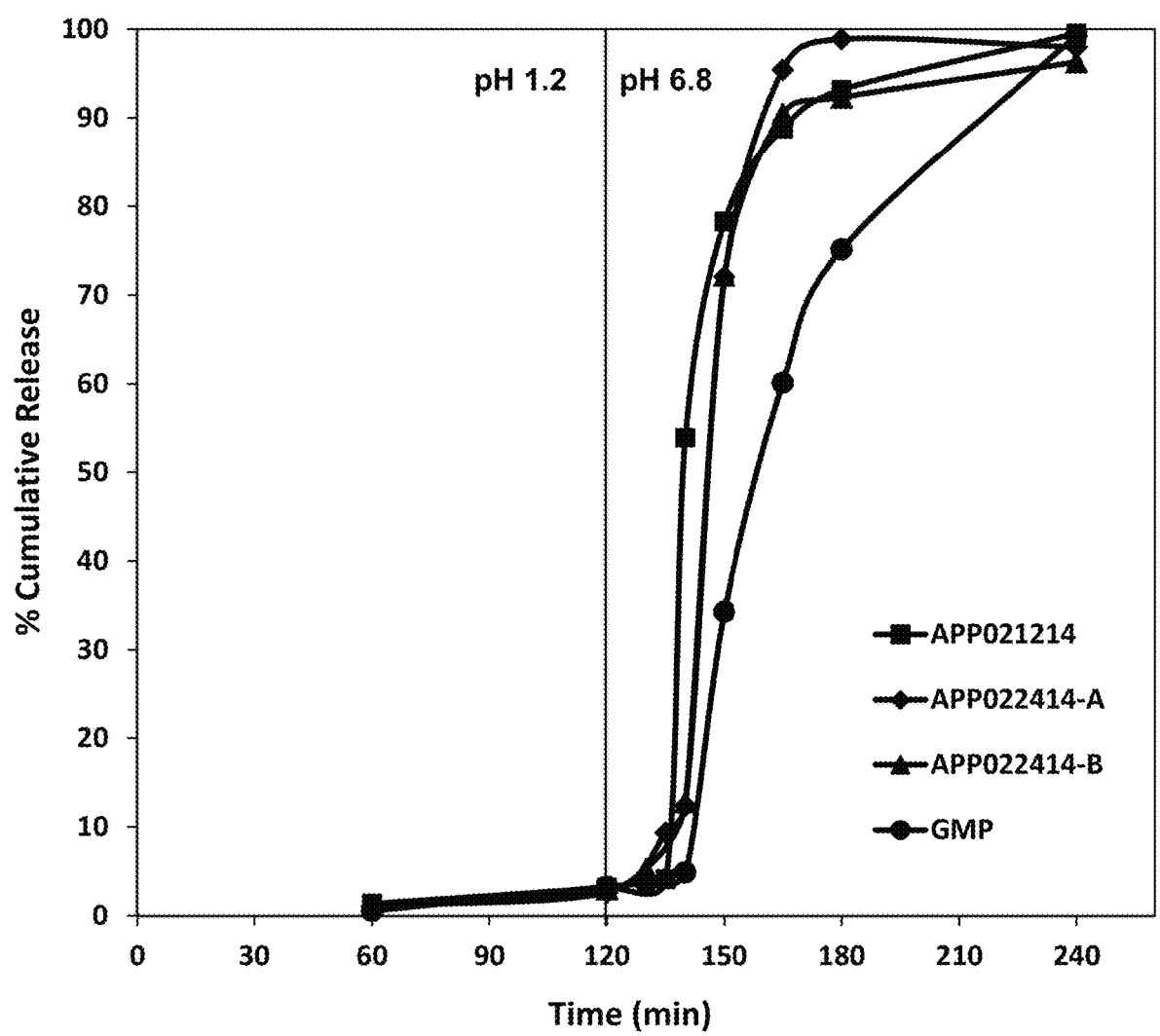
FIG. 10. Two-stage dissolution of GMP batch compared to application batches.

A GMP batch of enteric soft capsules (0.038-inch shell thickness) comprising DMF particles having particle size distribution of PSD: d90≤90 μm was prepared with the matrix composition shown in Table 17 and analyzed in two stage (pH 1.2 and pH 6.8) dissolution experiments (FIG. 10) and compared to application batches (Table 15).

TABLE 17

GMP DMF Fill Composition

| Ingredient | mg/capsule | % weight |
|---|---|---|
| Dimethyl fumarate PSD: d90 ≤90 μm | 240 | 32.0 |
| Capmul ® MCM | 375 | 50.0 |
| Cremophor ® RH 40 | 75 | 10.0 |
| Povidone K 30 | 22.5 | 3.0 |
| Lactic acid | 37.5 | 5.0 |
| TOTAL | 750 mg | 100% |

Example 11

Povidone K30 and PEG 600 Affect DMF Release Rate

Figure 11:
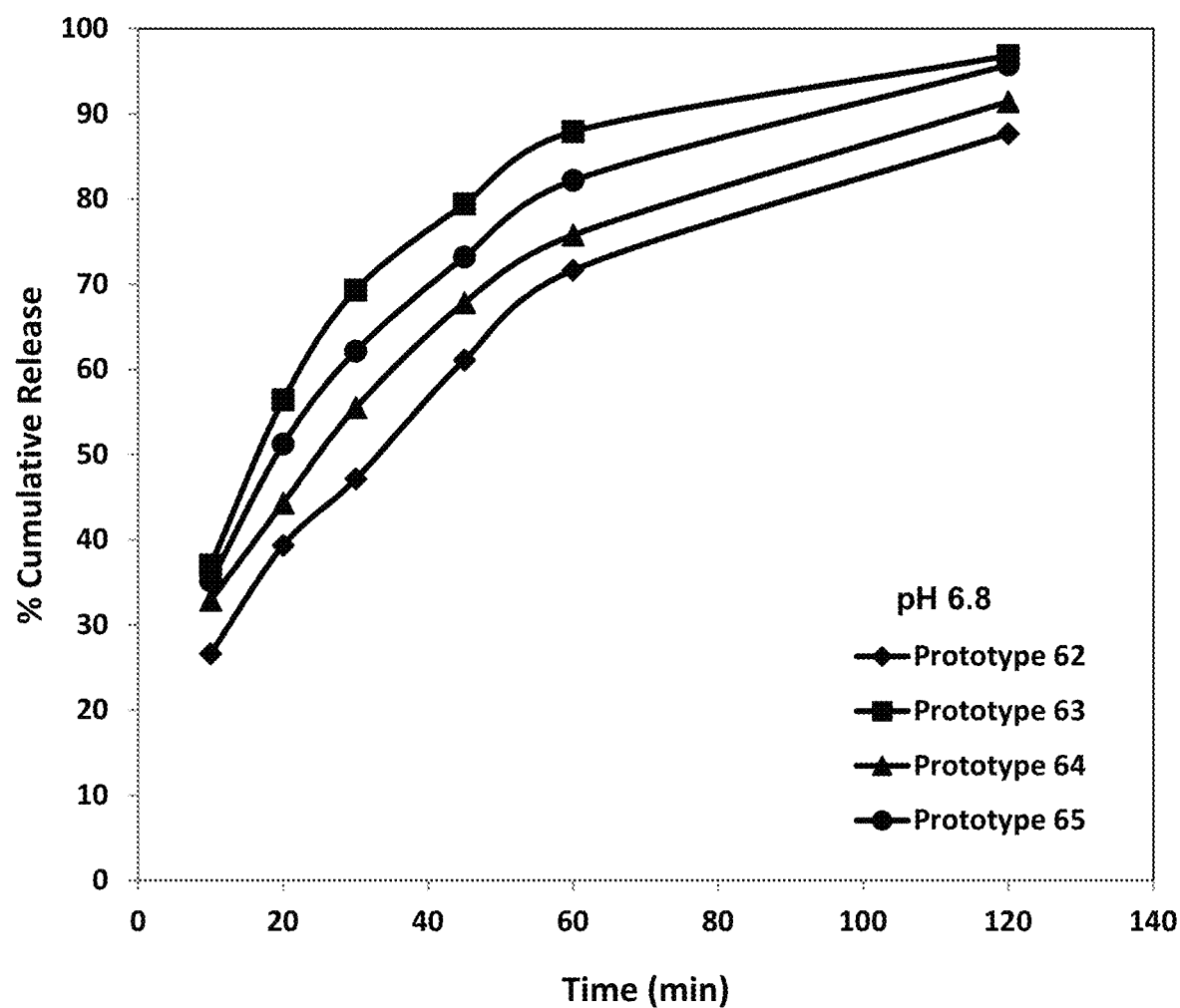
FIG. 11. Effects of Povidone K30 and PEG 600 on DMF release rate.

DMF matrices were prepared with and without Povidone K30 or PEG 600 (Table 18) and analyzed in single stage (pH 6.8) dissolution experiments (FIG. 11).

TABLE 18

DMF Fill Compositions

| | A (P62) | | B (P63) | |
|---|---|---|---|---|
| Ingredient | mg/capsule | % weight | mg/capsule | % weight |
| Dimethyl fumarate PSD: d90 ≤90 μm | 240 | 28.2 | 240 | 28.24 |
| Capmul ® MCM | 482.5 | 56.8 | 384.75 | 45.26 |
| Cremophor ® RH 40 | 85 | 10.0 | 85 | 10.00 |
| Povidone K 30 | — | — | 12.75 | 1.50 |
| PEG 600 | — | — | 85 | 10.00 |
| Lactic acid | 42.5 | 5.0 | 42.5 | 5.0 |
| TOTAL | 850 mg | 100% | 850 mg | 100% |

| | C (P64) | | D (P65) | |
|---|---|---|---|---|
| Ingredient | mg/capsule | % weight | mg/capsule | % weight |
| Dimethyl fumarate PSD: d90 ≤90 μm | 240 | 28.24 | 240 | 28.24 |
| Capmul ® MCM | 457 | 53.76 | 372 | 43.76 |
| Cremophor ® RH 40 | 85 | 10.00 | 85 | 10.00 |

TABLE 18-continued

| DMF Fill Compositions | | | | |
|---|---|---|---|---|
| Povidone K 30 | 25.5 | 3.00 | 25.5 | 3.00 |
| PEG 600 | — | — | 85 | 10.00 |
| Lactic acid | 42.5 | 5.00 | 42.5 | 5.00 |
| TOTAL | 850 mg | 100% | 850 mg | 100% |

Example 12

Figure 12:
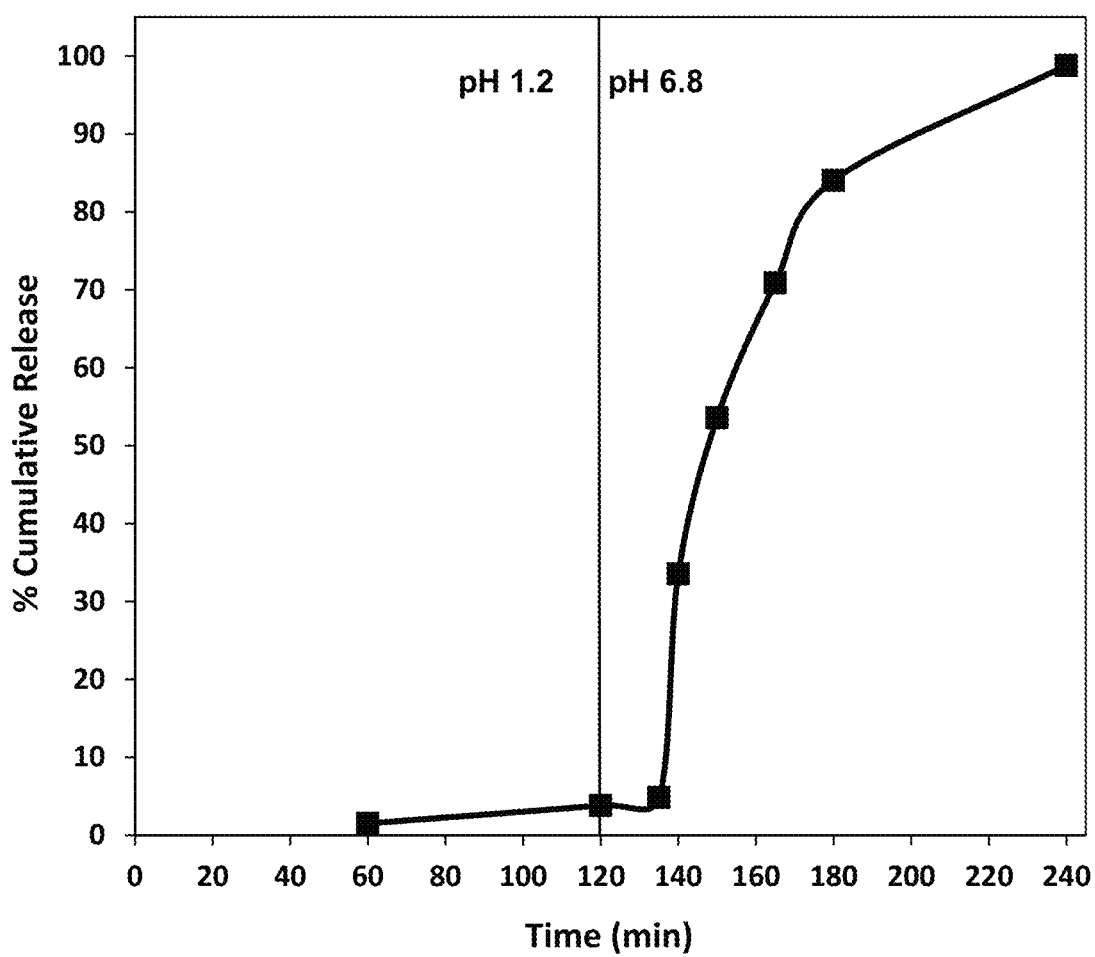
FIG. 12. Two-stage dissolution of 120 mg DMF enteric soft capsule.

A batch of enteric soft capsules (0.038 inch shell thickness) comprising DMF particles having particle size distribution of PSD: d90≤90 μm was prepared with the matrix composition shown in Table 19 and analyzed in two stage (pH 1.2 and pH 6.8) dissolution experiments (FIG. 12). This example provides a lower dose of DMF (120 mg) compared with that shown in Table 6 (240 mg).

TABLE 19

| DMF Fill Composition | | |
|---|---|---|
| Ingredient | mg/capsule | % weight |
| Dimethyl fumarate PSD: d90 ≤90 μm | 120 | 28.2 |
| Capmul ® MCM | 228.5 | 53.8 |
| Cremophor ® RH 40 | 42.5 | 10.0 |
| Povidone K 30 | 12.75 | 3.0 |
| Lactic acid | 21.25 | 5.0 |
| TOTAL | 425 mg | 100% |

Example 13

A batch of enteric soft capsules (0.038 inch shell thickness) comprising monomethyl fumarate (MMF) particles having particle size distribution of PSD: d90≤90 μm was prepared with the matrix composition shown in Table 20. This example provides MMF (240 mg).

TABLE 20

| MMF Fill Composition | | |
|---|---|---|
| Ingredient | mg/capsule | % weight |
| Monomethyl fumarate PSD: d90 ≤90 μm | 240 | 28.2 |
| Capmul ® MCM | 457 | 53.8 |
| Cremophor ® RH 40 | 85 | 10.0 |
| Povidone K 30 | 25.5 | 3.0 |
| Lactic acid | 42.5 | 5.0 |
| TOTAL | 850 mg | 100% |

Example 14

A batch of enteric soft capsules (0.038 inch shell thickness) comprising monomethyl fumarate (MMF) particles having particle size distribution of PSD: d90≤90 μm can be prepared with the matrix composition shown in Table 21. This example provides MMF (480 mg).

TABLE 21

| MMF Fill Composition | | |
|---|---|---|
| Ingredient | mg/capsule | % weight |
| Monomethyl fumarate PSD: d90 ≤90 μm | 480 | 48-56.4 |
| Capmul ® MCM | 216-470 | 25.5-47 |
| Cremophor ® RH 40 | 7.3-120 | 0.85-12 |
| Povidone K 30 | 7.3-50 | 0.85-5 |
| Lactic acid | 21.7-50 | 2.55-5 |
| TOTAL | 850 mg-1000 mg | 100% |

Example 15

Enteric soft capsules comprising particles of dimethyl fumarate, monomethyl fumarate, or a combination thereof having particle size distribution of PSD: d90≤90 μm can be prepared with an 850 mg matrix in the compositions shown in Table 22. This example provides DMF or MMF in a QD formulation (~480 mg).

TABLE 22

| DMF/MMF 850 mg Fill Compositions | | | | | | |
|---|---|---|---|---|---|---|
| | Percent Weight | | | | | |
| Ingredient | EX1 | EX2 | EX3 | EX4 | EX5 | EX6 |
| Dimethyl fumarate or Monomethyl fumarate PSD: d90 ≤ 90 μm | 56.4 | 56.4 | 56.4 | 56.4 | 56.4 | 56.4 |
| Capmul ® MCM | 30.6 | 39.95 | 28.9 | 28.9 | 25.5 | 32.7 |
| Cremophor ® RH 40 | 8.5 | 0.85 | 8.5 | 8.5 | 10.2 | 6.1 |
| Povidone K 30 | 0.85 | 0.85 | 2.55 | 2.55 | 4.25 | 1.8 |
| Lactic acid | 4.25 | 2.55 | 4.25 | 4.25 | 4.25 | 3.0 |
| TOTAL | 100 | 100 | 100 | 100 | 100 | 100 |

Example 16

Enteric soft capsules comprising particles of dimethyl fumarate, monomethyl fumarate, or a combination thereof having particle size distribution of PSD: d90≤90 μm can be prepared with a 1000 mg matrix in the compositions shown in Table 23. This example provides DMF or MMF in a QD formulation (~480 mg).

TABLE 23

| DMF/MMF 1000 mg Fill Compositions | | | | | | |
|---|---|---|---|---|---|---|
| | Percent Weight | | | | | |
| Ingredient | EX1 | EX2 | EX3 | EX4 | EX5 | EX6 |
| Dimethyl fumarate or Monomethyl fumarate PSD: d90 ≤ 90 μm | 48 | 48 | 48 | 48 | 48 | 48 |
| Capmul ® MCM | 44 | 36 | 47 | 34 | 34 | 38.9 |
| Cremophor ® RH 40 | 2 | 10 | 1 | 10 | 10 | 7.2 |
| Povidone K 30 | 1 | 1 | 1 | 3 | 3 | 2.2 |
| Lactic acid | 5 | 5 | 3 | 5 | 5 | 3.6 |
| TOTAL | 100 | 100 | 100 | 100 | 100 | 100 |

Example 17

Stability of the Enteric Soft Capsules over Time

Figure 13:
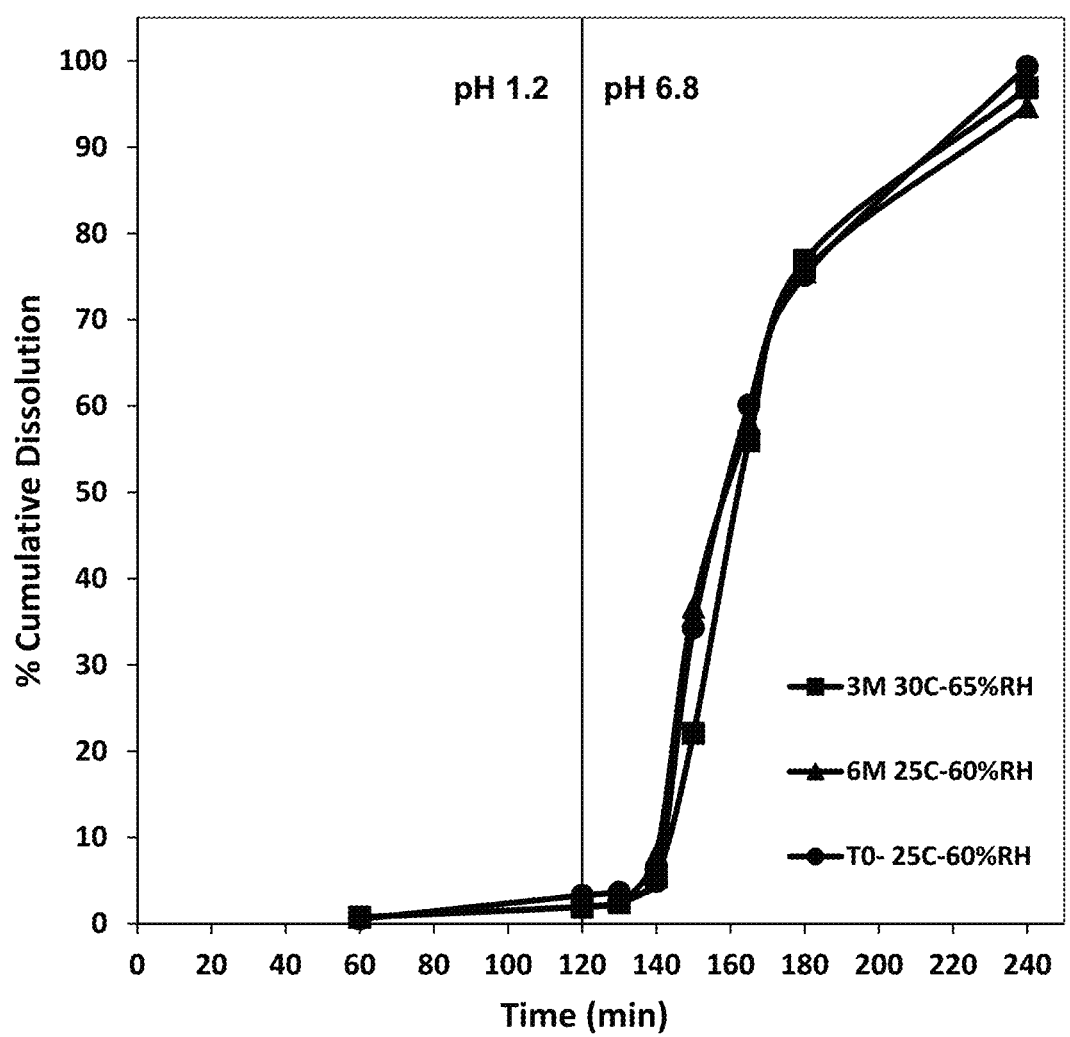
FIG. 13. DMF enteric soft capsule stability at $T_0$ and after 3- and 6-month conditions.

The temporal stability of the dimethyl fumarate enteric soft capsule pharmaceutical composition shown in Table 24 was assessed under three ICH conditions. A sample of DMF enteric soft capsules was subject to chemical analysis and two-stage dissolution shortly after manufacturing (T$_0$). Samples of DMF enteric soft capsules were subjected to Room Temperature Conditions (25° C., 60% relative humidity) for 1 month, 2, months, 3 months, and 6 months. Other samples of DMF enteric soft capsules were subjected to Intermediate Conditions (30° C., 65% relative humidity) for 1 month, 2 months, and 3 months. Additional samples of DMF enteric soft capsules were subjected to Accelerated Conditions (40° C. and 75% relative humidity) for 1 month and 2 months. After the designated incubation period, the capsules were chemically analyzed and evaluated in two-stage dissolution experiments at pH 1.2 and 6.8 as described herein if conditions permitted (i.e., non-leaking capsules). Two-stage dissolution results for DMS enteric soft capsules at T$_0$, and after 3- and 6-months at Room Temperature Conditions (25° C., 60% RH) are shown in FIG. 13.

TABLE 24

GMP DMF Fill Composition

| Ingredient | mg/capsule | % weight |
|---|---|---|
| Dimethyl fumarate PSD: d90 ≤90 μm | 240 | 32.0 |
| Capmul ® MCM | 375 | 50.0 |
| Cremophor ® RH 40 | 75 | 10.0 |
| Povidone K 30 | 22.5 | 3.0 |
| Lactic acid | 37.5 | 5.0 |
| TOTAL | 750 mg | 100% |

TABLE 25

GMP DMF Stability

| | Initial | 25° C., 60% Relative Humidity | | | |
|---|---|---|---|---|---|
| | T$_0$ | 1 M | 2 M | 3 M | 6 M |
| Assay | 101.2% | 101.0% | 102.4% | 101.25 | 98.8% |
| Degradation Products | | | | | |
| Monomethyl Fumarate | 0.14% | 0.13% | 0.14% | 0.16% | 0.18% |
| RRT 0.74 | ND | ND | 0.07% | 0.09% | 0.18% |
| RRT 1.61 | 0.05% | ND | ND | ND | ND |
| RRT 2.18 | ND | ND | ND | <0.05% | 0.09% |
| Total Degradation Products | 0.19% | 0.13% | 0.21% | 0.25% | 0.45% |

| | 30° C., 65% Relative Humidity | | | 40° C., 75% Rel. Humid. | |
|---|---|---|---|---|---|
| | 1 M | 2 M | 3 M | 1 M | 2 M |
| Assay | 100.1% | 99.4% | 99.5% | 99.3 | 113.1* |
| Degradation Products | | | | | |
| Monomethyl Fumarate | 0.14% | 0.17% | 0.22% | 0.22% | 0.26% |
| RRT 0.74 | 0.14% | 0.22% | 0.28% | 0.3% | 0.46% |
| RRT 1.61 | 0.06% | 0.11% | 0.14% | 0.15% | 0.35% |
| RRT 2.18 | 0.34% | 0.5% | 0.64% | 0.67% | 1.07% |
| Total Degradation Products | 0.14% | 0.17% | 0.22% | 0.22% | 0.26% |

*Data was collected on fill extracted from leaking capsules.

Note:
Leaking capsules were observed at the 2- and 3-month time points for the accelerated condition (40° C., 75% RH). This was expected for the enteric soft gelatin capsules. The intermediate condition (30° C., 65% RH) and long-term condition (25° C., 60% RH) will be assessed at the 12-month and 24-month time points to assess chemical stability.

What is claimed is:

1. An oral immediate release pharmaceutical composition comprising a single phase non-aqueous liquid vehicle comprising a suspension of a fumarate esters or a salt thereof having the formula:

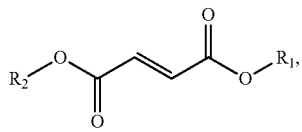

wherein R$_1$ and R$_2$, may be the same or different, and independently represent hydrogen or methyl.

2. The composition of claim 1, wherein R$_1$ is hydrogen.
3. The composition of claim 1, wherein R$_1$ is methyl.
4. The composition of claim 1, wherein R$_2$ is methyl.
5. The composition of claim 1, wherein R$_1$ is hydrogen and R$_2$ is methyl.
6. The composition of claim 1, wherein R$_1$ is methyl and R$_2$ is methyl.
7. The composition of claim 1, wherein the fumarate ester is:

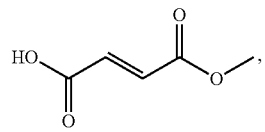

or a salt thereof.

8. The composition of claim 1, wherein the fumarate ester is:

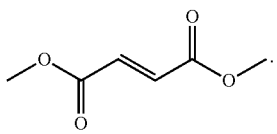

9. The composition of claim 1, wherein the liquid vehicle comprises mono- and di-glycerides, polyvinylpyrrolidone, and polyoxyl 40 hydrogenated castor oil.
10. The composition of claim 1, wherein the liquid vehicle comprises lactic acid.
11. The composition of claim 1, wherein the composition comprises:
    about 25% to about 50% by weight of the composition of the one or more fumarate esters or salts thereof;

about 40% to about 54% by weight of the composition of mono- and di-glycerides;

about 1% to about 10% by weight of the composition of polyvinylpyrrolidone;

about 2% to about 10% by weight of the composition of polyoxyl 40 hydrogenated castor oil; and about 5% b weight of the composition of lactic acid.

12. The composition of claim 1, wherein the composition is encapsulated in a capsule.

13. The composition of claim 1, wherein the composition is encapsulated in an enteric soft capsule.

14. The composition of claim 13, wherein the enteric soft capsule provides delayed release of the fumarate ester.

15. The composition of claim 1, wherein the fumarate ester is in the form of milled or micronized particles.

16. The composition of claim 11, wherein the composition is stable for at least 1 year at 25° C.

* * * * *